(12) United States Patent
Hettmann et al.

(10) Patent No.: US 8,933,202 B2
(45) Date of Patent: Jan. 13, 2015

(54) AXL ANTIBODIES

(75) Inventors: Thore Hettmann, München (DE); Jens Niewöhner, München (DE); Jens Ruhe, Martinsried (DE); Peter Wirtz, Gauting (DE); Kerstin Selle, Pentenried (DE); Esther Zwick-Wallasch, Gauting (DE); Mike Rothe, Krailling (DE)

(73) Assignee: U3 Pharma GmbH, Martinsried (DE)

( * ) Notice: Subject to any disclaimer, the term of this patent is extended or adjusted under 35 U.S.C. 154(b) by 415 days.

(21) Appl. No.: 12/742,546

(22) PCT Filed: Nov. 12, 2008

(86) PCT No.: PCT/EP2008/009548
§ 371 (c)(1),
(2), (4) Date: Jun. 25, 2010

(87) PCT Pub. No.: WO2009/062690
PCT Pub. Date: May 22, 2009

(65) Prior Publication Data
US 2010/0330095 A1    Dec. 30, 2010

(30) Foreign Application Priority Data

Nov. 12, 2007    (EP) .................................... 07021931

(51) Int. Cl.
| | | |
|---|---|---|
| *C07K 16/40* | (2006.01) | |
| *C07K 16/00* | (2006.01) | |
| *A61K 39/395* | (2006.01) | |
| *C07K 16/28* | (2006.01) | |
| *A61K 31/282* | (2006.01) | |
| *A61K 31/704* | (2006.01) | |
| *A61K 45/06* | (2006.01) | |
| *A61K 39/00* | (2006.01) | |

(52) U.S. Cl.
CPC ........... *C07K 16/2863* (2013.01); *A61K 31/282* (2013.01); *A61K 31/704* (2013.01); *A61K 39/3955* (2013.01); *A61K 45/06* (2013.01); *A61K 2039/505* (2013.01); *C07K 2316/96* (2013.01); *C07K 2317/24* (2013.01); *C07K 2317/56* (2013.01); *C07K 2317/565* (2013.01); *C07K 2317/92* (2013.01)
USPC ................ 530/388.26; 530/388.1; 424/146.1; 424/141.1

(58) Field of Classification Search
CPC .............. A61K 2300/00; A61K 38/00; A61K 2039/505; C12Q 1/6886; C07D 471/04
See application file for complete search history.

(56) References Cited

U.S. PATENT DOCUMENTS

| 4,931,385 A | 6/1990 | Block et al. |
|---|---|---|
| 5,468,634 A | 11/1995 | Liu |
| 8,415,361 B2 | 4/2013 | Lemke et al. |
| 2005/0186571 A1* | 8/2005 | Ullrich et al. ..................... 435/6 |
| 2007/0065444 A1 | 3/2007 | North et al. |
| 2009/0087431 A1* | 4/2009 | Yaworsky et al. ......... 424/133.1 |
| 2010/0330095 A1 | 12/2010 | Hettmann et al. |

FOREIGN PATENT DOCUMENTS

| EP | 0 378 175 A | 7/1990 |
|---|---|---|
| EP | 1 382 969 A1 | 1/2004 |
| GB | 2404660 A | 2/2005 |
| WO | 97/34636 A | 9/1997 |
| WO | 00/75333 A | 12/2000 |
| WO | 2005/047327 A | 5/2005 |
| WO | 2006037604 A1 | 4/2006 |
| WO | 2006/096461 A | 9/2006 |
| WO | 2006/104989 A | 10/2006 |
| WO | 2006/131013 A | 12/2006 |
| WO | 2009062690 A1 | 5/2009 |

OTHER PUBLICATIONS

Rudikoff et al. (Proc Natl Acad Sci USA 1982 vol. 79 p. 1979).*
MacCallum et al. J. Mol. Biol. (1996) 262, 732-745.*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
McGuire et al. (Journal of Clinical Oncology 2005, 23:5862-5864).*
The Merck Manuals Online Medical Library, [online]. Whitehouse Station, NJ: Merck Research Laboratories, 2006-2007. [retrieved on Nov. 19, 2007]. Retrieved from the Internet: < URL: http://www.merckmanuals.com/professional/sec18/ch253/ch253e.html>. Breast Cancer. see pp. 1-8.*
Ax1 (/49M): sc-73719, Aug. 15, 2007, Santa Cruz Biotechnology, Inc., XP002513577, Retrieved from Internet: URL: http://datasheets.scbt.com/sc-73719.pd.
Holland et al., "Multiple roles for the receptor tyrosine kinase Axl in tumor formation", Cancer Research, vol. 065, No. 20, Oct. 2005, pp. 9294-9303.
Vajkoczy et al., "Dominant-negative inhibition of the Ax1 receptor tyrosine kinase suppresses brain tumor cell growth and invasion and prolongs survival.", Proceedings of the Natinal Academy of Sciences of the United States of America, Apr. 11, 2006, vol. 103, No. 15, Apr. 11, 2006, pp. 5799-5804.
Saito et al., "Capecitabine combined with monoclonal antibody therapy for breast cancer", Frontiers in Cancer Treatment, 2004, 16(2), pp. 133-136 (Abstract).
Suzuki, "Characteristics of anti-angiogenesis drugs and their efficacy on tumor growth inhibition", Frontiers in Cancer Treatment, 1999, 17(6), pp. 747-752 (Abstract).
Notice of Reasons for Rejection cited in Japanese Application No. 2010-53210 dated Aug. 27, 2013, 7 pages.

* cited by examiner

*Primary Examiner* — Sharon Wen
(74) *Attorney, Agent, or Firm* — Rothwell, Figg, Ernst & Manbeck, P.C.

(57) ABSTRACT

The present invention refers to antibodies, particularly to monoclonal antibodies, which bind to the extracellular domain of the AXL receptor tyrosine kinase and which at least partially inhibit AXL activity.

28 Claims, 20 Drawing Sheets

Rat1-Mock polyclonal

Rat1-Axl cl.2

NIH3T3-pLXSN-poly

72A1

MAB154

NIH3T3-Axl-cl.7

72A1

MAB154

A  NIH3T3-Axl cl.7

B  NCI-H292

A  NIH3T3-Axl cl.7

B  CaLu-1

11B7 (rIgG2a)

ch11B7 (hIgG2)

11D5 (rIgG2a)

ch11D5 (hIgG2)

A  11B7

B  11D5

A

Figure 1:
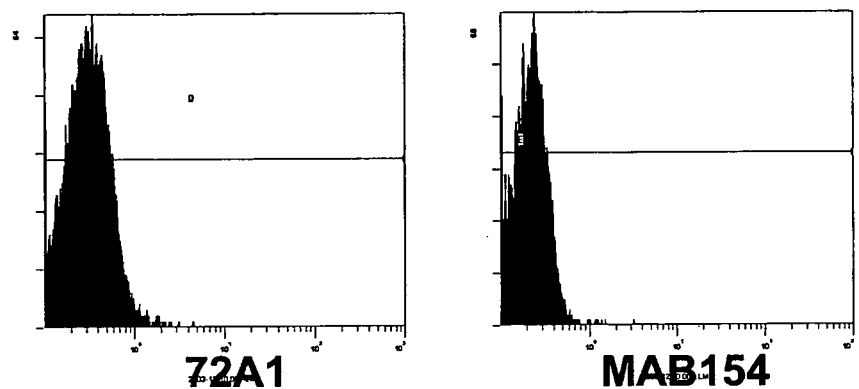
Figure 1:
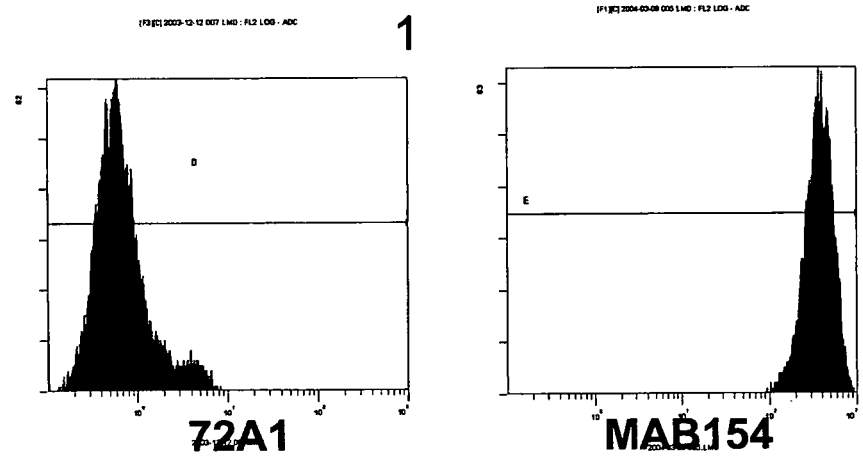

| | Intensity ≥ 1 | |
| --- | --- | --- |
| | Tumor | Adjacent |
| Breast | 3/3 | 0/3 |
| Colon | 3/11 | 0/11 |
| Lung | 2/9 | 0/9 |
| Kidney | 0/10 | 0/10 |
| Fol. Lymphoma | 0/12 | 0/3 |
| Skin/Melanoma | 1/13 | 0/12 |
| Ovary | 4/11 | 0/9 |
| Prostate | 0/11 | 0/9 |
| Pancreas | 2/9 | 0/11 |
| Esophagus | 4/10 | 0/10 |
| Barrett | 4/11 | 0/9 |
| Stomach | 6/10 | 0/7 |
| Bladder | 8/10 | 0/10 |
| Cervix | 7/9 | 0/9 |
| Liver | 3/9 | 0/7 |
| Thyroid | 5/9 | 0/11 |
| Head & Neck | 8/20 | 0/17 |

B

Breast cancer

Gastric signet ring cell carcinoma

A 11B7 (rIgG1)

antibody treatment

B ch11B7 (hIgG1)

antibody treatment

A  11B7 (rIgG1)

B  ch11B7 (hIgG1)

AXL ANTIBODIES

CROSS REFERENCE TO RELATED APPLICATION

This application is a 35 U.S.C. 371 National Phase Entry Application from PCT/EP2008/009548, filed Nov. 12, 2008, which claims the benefit of European Patent Application No. 07 021 931.6 filed on Nov. 12, 2007, the disclosure of which is incorporated herein in its entirety by reference.

The present invention refers to antibodies, particularly to monoclonal antibodies, which bind to the extracellular domain of the AXL receptor tyrosine kinase and which at least partially inhibit AXL activity.

BACKGROUND

The AXL (Ark, UFO, Tyro-7) receptor tyrosine kinase is a member of the Tyro-3 family of kinases with the other members being Mer (Eyk, Nyk, Tyro-12) and Sky (Rse, Tyro-3, Dtk, Etk, Brt, Tif). It is activated by binding of the heterophilic ligand Gas6, a 70-kDa protein homologous to the anticoagulation factor protein S. In contrast to other receptor tyrosine kinases, AXL tyrosine phosphorylation can also be induced by homophilic binding. AXL activation leads to signalling through PI-3-kinase/Akt (Franke et al., Oncogene 22: 8983-8998, 2003) and other major pathways like Ras/Erk and β-catenin/TCF (Goruppi et al., Mol. Cell. Biol. 21: 902-915, 2001).

AXL is weakly expressed in a range of normal tissues, including brain, heart, skeletal muscle, the organ capsules and connective tissues of several other organs, and in monocytes, but not lymphocytes. Akt phosphorylation induced by AXL has been described in survival of fibroblasts (Goruppi et al., Mol Cell Biol 17: 4442-4453 1997), endothelial cells (Hasanbasic et al., Am J Physiol Heart Circ Physiol, 2004), vascular smooth muscle cells (Melaragno et al., J. Mol. Cell. Cardiol. 37: 881-887, 2004) and neurons (Allen et al., Mol. Endocrinol. 13: 191-201 1999). Furthermore, AXL plays a role in cell-adhesion and chemotaxis. AXL knockouts display impaired platelet aggregate stabilization and thrombus formation as a result of reduced activation of the platelet integrin IIb3.

AXL overexpression has been demonstrated in various cancer types, e.g. breast (Meric et al., Clin. Cancer Res. 8: 361-367, 2002; Berclaz et al., Ann. Oncol. 12: 819-824, 2001), colon (Chen et al., In J. Cancer 83: 579-584, 1999; Craven et al., Int. J. Cancer 60: 791-797, 1995), prostate (Jacob et al., Cancer Detect. Prev. 23: 325-332, 1999), lung (Wimmel et al., Eur J Cancer 37: 2264-2274, 2001), gastric (Wu et al., Anticancer Res 22: 1071-1078, 2002), ovarian (Sun et al., Oncology 66: 450-457, 2004), endometrial (Sun et al., Ann. Oncol. 14: 898-906, 2003), renal (Chung et al., DNA Cell Biol. 22: 533-540, 2003), hepatocellular (Tsou et al., Genomics 50:331-340, 1998), thyroid (Ito et al., Thyroid 12:971-975, 2002; Ito et al., Thyroid 9: 563-567, 1999), and esophageal carcinoma (Nemoto et al., 1997), furthermore in CML (Janssen et al., A novel putative tyrosine kinase receptor with oncogenic potential. Oncogene, 6: 2113-2120, 1991; Braunger et al., Oncogene 14:2619-2631 1997; O'Bryan et al., Mol Cell Biol 11:5016-5031, 1991), AML (Rochlitz et al., Leukemia 13: 1352-1358, 1999), osteosarcoma (Nakano et al., J. Biol. Chem. 270:5702-5705, 2003) melanoma (van Ginkel et al., Cancer Res 64:128-134, 2004) and in head and neck squamous cell carcinoma (Green et al., Br J. Cancer. 2006 94:1446-5, 2006).

Moreover AXL has been identified as a metastasis-associated gene that is upregulated in aggressive breast cancer cell lines compared to non-invasive cells. In vitro, AXL activity was found to be required for migration and invasion, and this activity could be inhibited by antibody treatment (WO04008147). Similarly, abrogation of AXL activity in vivo, either via expression of a dominant negative version of AXL (Vajkoczy, P., et al., Proc. Natl. Acad. Science U.S.A. 103: 5799-5804. 2005) or by siRNA mediated downregulation of AXL (Holland et al., Cancer Res. 65: 9294-9303, 2005) prevented subcutaneous and orthotopic cell growth in murine xenograft experiments.

So far two antibodies that bind to AXL and posses biological activity have been described. One antibody is capable of reducing AXL mediated cell invasion (WO04008147) whereas the other antibody has been reported to reduce AXL/Ligand interaction. However both antibodies are polyclonal rendering them unsuitable for therapeutic administration.

Thus in light of the therapeutic potential of AXL there is a high need for monoclonal AXL antibodies, antibody fragments or derivatives thereof that effectively and specifically block AXL mediated signal transduction and which are suitable for therapeutic treatment.

Accordingly a first aspect of the present invention relates to a monoclonal antibody including a fragment or derivative thereof that binds to the extracellular domain of AXL, particularly of human AXL, and at least partially inhibits AXL activity.

Preferably the antibody of the present invention further possesses at least one or more of the following properties: the ability to reduce or block AXL-mediated signal transduction, the ability to reduce or block AXL phosphorylation, the ability to reduce or block cell proliferation, the ability to reduce or block angiogenesis, the ability to reduce or block cell migration, the ability to reduce or block tumor metastasis, the ability to reduce or block AXL mediated PI3K signaling and the ability to reduce or block AXL mediated anti-apoptosis, thereby increasing for example the sensitivity of a cell against treatment with an antineoplastic agent. Moreover the antibodies of the present invention may exhibit high specificity for AXL, particularly human AXL and do not significantly recognize other Tyro-3 family members, e.g. MER and/or SKY and/or mammalian non-primate AXL, such as murine AXL. Antibody specificity may be determined by measurements of cross-reactivity as described in the Examples.

The term "activity" refers to the biological function of AXL, which influences the phenotype of a cell, in particular but not limited to cancer phenotypes such as evasion of apoptosis, self sufficiency in growth signals, cell proliferation, tissue invasion and/or metastasis, insensitivity to anti-growth signals (anti-apoptosis) and/or sustained angiogenesis.

The term "AXL mediated signal transduction" means the activation of second messenger pathways triggered by direct or indirect interaction of AXL with second messenger molecules.

The term "AXL phosphorylation" refers to the phosphorylation of amino acid residues, preferably tyrosine residues, either by a second AXL protein (transphosphorylation) or by another protein having protein kinase activity.

The term "cell proliferation" refers to all AXL-involving processes underlying the reproduction of human cells, in particular but not limited to human cancer cells. They contribute to or result in the replication of cellular DNA, separation of the duplicated DNA into two equally sized groups of chromosomes, and the physical division (called cytokinesis) of entire cells, and shall be stimulated or mediated by non-catalytic or catalytic activities of AXL, preferably including AXL phosphorylation and/or AXL-mediated signal transduction.

The term "angiogenesis" refers to all AXL-involving processes that contribute to the growth of new blood vessels from pre-existing vessels, in particular but not limited to new tumor supplying blood vessels. These processes include multiple cellular events such as proliferation, survival, migration and sprouting of vascular endothelial cells, attraction and migration of pericytes as well as basal membrane formation for vessel stabilization, vessel perfusion, or secretion of angiogenic factors by stromal or neoplastic cells, and shall be stimulated or mediated by non-catalytic or catalytic activities of AXL, preferably including AXL phosphorylation and/or AXL-mediated signal transduction.

The term "metastasis" refers to all AXL-involving processes that support cancer cells to disperse from a primary tumor, penetrate into lymphatic and/or blood vessels, circulate through the bloodstream, and grow in a distant focus (metastasis) in normal tissues elsewhere in the body. In particular, it refers to cellular events of tumor cells such as proliferation, migration, anchorage independence, evasion of apoptosis, or secretion of angiogenic factors, that underly metastasis and are stimulated or mediated by non-catalytic or catalytic activities of AXL, preferably including AXL phosphorylation and/or AXL-mediated signal transduction.

The term "AXL mediated anti-apoptosis" refers to all AXL-involving processes that prevent human cells, preferably but not limited to human cancer cells from programmed cell death (apoptosis). In particular, it refers to processes that prevent human cells, preferably but not limited to human cancer cells from induction of apoptosis through growth factor withdrawal, hypoxia, exposure to chemotherapeutic agents or radiation, or initiation of the Fas/Apo-1 receptor-mediated signaling, and are stimulated or mediated by non-catalytic or catalytic activities of AXL, preferably including AXL phosphorylation and/or AXL-mediated signal transduction.

In addition, the present invention includes antibodies whose binding activities to AXL are $KD=10^{-5}$ M or lower, preferably $KD=10^{-7}$ M or lower, and most preferably $KD=10^{-9}$ M or lower. Whether the binding activity of an antibody of the present invention to AXL is $KD=10^{-5}$ M or lower can be determined by methods known to those skilled in the art. For example, the activity can be determined using surface plasmon resonance with Biacore, and/or by ELISA (enzyme-linked immunosorbent assays), EIA (enzyme immunoassays), RIA (radioimmunoassays), or fluorescent antibody techniques, e.g. FACS.

In a second aspect, the antibody may have at least one antigen binding site, e.g. one or two antigen binding sites. Further, the antibody preferably comprises at least one heavy immunoglobulin chain and at least one light immunoglobulin chain. An immunoglobulin chain comprises a variable domain and optionally a constant domain. A variable domain may comprise complementary determining regions (CDRs), e.g. a CDR1, CDR2 and/or CDR3 region, and framework regions. The term "complementary determining region" (CDR) is well-defined in the art (see, for example, Harlow and Lane, "Antibodies, a Laboratory Manual", CSH Press, Cold Spring Harbour, 1988) and refers to the stretches of amino acids within the variable region of an antibody that primarily makes contact with the antigen.

A further aspect of the present invention relates to an antibody including a fragment or derivative thereof that binds to the extracellular domain of AXL which comprises at least one heavy chain amino acid sequence comprising at least one CDR selected from the group consisting of
(a) a CDRH1 as shown in SEQ ID NOs: 16, 22, 28, or a CDRH1 to sequence differing in 1 or 2 amino acids therefrom,
(b) a CDRH2 as shown in SEQ ID NOs: 17, 23, 29, or a CDRH2 sequence differing in 1 or 2 amino acids therefrom, and
(c) a CDRH3 as shown in SEQ ID NOs: 18, 24, 30, or a CDRH3 sequence differing in 1 or 2 amino acids therefrom, and/or at least:
one light chain amino acid sequence comprising at least one CDR selected from the group consisting of
(d) a CDRL1 as shown in SEQ ID NOs: 13, 19, 25, or a CDRL1 sequence differing in 1 or 2 amino acids therefrom,
(e) a CDRL2 as shown in SEQ ID NOs: 14, 20, 26, or a CDRL2 sequence differing in 1 or 2 amino acids therefrom, and
(f) a CDRL3 as shown in SEQ ID NOs: 15, 21, 27, or a CDRL3 sequence differing in 1 or 2 amino acids therefrom, or a monoclonal antibody recognizing the same epitope on the extracellular domain of AXL.

In a preferred embodiment, the antibody comprises a heavy chain comprising at least one CDR selected from the group consisting of
(a) a CDRH1 as shown in SEQ ID NO: 16, or a CDRH1 sequence differing in 1 or 2 amino acids therefrom,
(b) a CDRH2 as shown in SEQ ID NO: 17, or a CDRH2 sequence differing in 1 or 2 amino acids therefrom, and
(c) a CDRH3 as shown in SEQ ID NO: 18, or a CDRH3 sequence differing in 1 or 2 amino acids therefrom, and/or a light chain comprising at least one CDR selected from the group consisting of
(d) a CDRL1 as shown in SEQ ID NO: 13, or a CDRL1 sequence differing in 1 or 2 amino acids therefrom,
(e) a CDRL2 as shown in SEQ ID NO: 14, or a CDRL2 sequence differing in one or two amino acids therefrom, and
(f) a CDRL3 as shown in SEQ ID NO: 15, or a CDRL3 sequence differing in 1 or 2 amino acids therefrom,
or an monoclonal antibody recognizing the same epitope on the extracellular domain of AXL.

In a further preferred embodiment, the antibody comprises a heavy chain comprising at least one CDR selected from the group consisting of
(a) a CDRH1 as shown in SEQ ID NO: 22, or a CDRH1 sequence differing in 1 or 2 amino acids therefrom,
(b) a CDRH2 as shown in SEQ ID NO: 23, or a CDRH2 sequence differing in 1 or 2 amino acids therefrom, and
(c) a CDRH3 as shown in SEQ ID NO: 24, or a CDRH3 sequence differing in 1 or 2 amino acids therefrom, and/or a light chain comprising at least one CDR selected from the group consisting of
(d) a CDRL1 as shown in SEQ ID NO: 19, or a CDRL1 sequence differing in 1 or 2 amino acids therefrom,
(e) a CDRL2 as shown in SEQ ID NO: 20, or a CDRL2 sequence differing in one or two amino acids therefrom, and
(f) a CDRL3 as shown in SEQ ID NO: 21, or a CDRL3 sequence differing in 1 or 2 amino acids therefrom,
or an monoclonal antibody recognizing the same epitope on the extracellular domain of AXL.

In a yet further preferred embodiment, the antibody comprises a heavy chain comprising at least one CDR selected from the group consisting of
(a) a CDRH1 as shown in SEQ ID NO: 28, or a CDRH1 sequence differing in 1 or 2 amino acids therefrom,
(b) a CDRH2 as shown in SEQ ID NO: 29, or a CDRH2 sequence differing in 1 or 2 amino acids therefrom, and (c) a CDRH3 as shown in SEQ ID NO: 30, or a CDRH3 sequence differing in 1 or 2 amino acids therefrom, and/or a light chain comprising at least one CDR selected from the group consisting of (d) a CDRL1 as shown in SEQ ID NO: 25, or a CDRL1 sequence differing in 1 or 2 amino acids therefrom, (e) a CDRL2 as shown in SEQ ID NO: 26, or a CDRL2 sequence differing in one or two amino acids therefrom, and (f) a CDRL3 as shown in SEQ ID NO: 27, or a CDRL3 sequence differing in 1 or 2 amino acids therefrom, or an monoclonal antibody recognizing the same epitope on the extracellular domain of AXL.

In another embodiment, the present invention refers to an antibody comprising a heavy chain amino acid sequence selected from the group consisting of SEQ ID NOs: 8, 10, 12 or at least the variable domain thereof or an amino acid sequence having a sequence identity of at least 90% thereto and/or a light chain amino acid sequence selected from the group consisting of SEQ. ID NOs: 7, 9, 11 or at least the variable domain thereof or an amino acid sequence having a sequence identity of at least 90% thereto or to an antibody recognizing the same epitope on the extracellular domain of AXL.

As used herein, "sequence identity" between two polypeptide sequences, indicates the percentage of amino acids that are identical between the sequences. Preferred polypeptide sequences of the invention have a sequence identity of at least 90%.

In a particular preferred embodiment, the antibody is selected from the group consisting of 11B7, 11D5, 10D12 or an antibody recognizing the same epitope on the extracellular domain of AXL.

The antibody may be any antibody of natural and/or synthetic origin, e.g. an antibody of mammalian origin. Preferably, the constant domain—if present—is a human constant domain. The variable domain is preferably a mammalian variable domain, e.g. a humanized or a human variable domain. More preferably, the antibody is a chimeric, humanized or human antibody.

The antibody of the invention may be of the IgA-, IgD-, IgE, IgG- or IgM-type, preferably of the IgG- or IgM-type including, but not limited to, the IgG1-, IgG2-, IgG3-, IgG4-, IgM1- and IgM2-type. In most preferred embodiments, the antibody is of the human IgG1-, IgG2- or IgG4-type.

As discussed, supra, there are a number of isotypes of antibodies. It will be appreciated that antibodies that are generated need not initially possess such an isotype but, rather the antibody as generated can possess any isotype and that the antibody can be isotype-switched by using the molecularly cloned V region genes or cloned constant region genes or cDNAs in appropriate expression vectors using conventional molecular biological techniques that are well known in the art and then expressing the antibodies in host cells using techniques known in the art The term antibody includes "fragments" or "derivatives", which have at least one antigen binding site of the antibody. Antibody fragments include Fab fragments, Fab' fragments $F(ab')_2$ fragments as well as Fv fragments.

Derivatives of the antibody include single chain antibodies, nanobodies, and diabodies. Derivatives of the antibody shall also include scaffold proteins having an antibody-like binding activity that bind to AXL.

Within the context of the present invention, the term "scaffold protein", as used herein, means a polypeptide or protein with exposed surface areas in which amino acid insertions, substitutions or deletions are highly tolerable. Examples of scaffold proteins that can be used in accordance with the present invention are protein A from *Staphylococcus aureus*, the bilin binding protein from *Pieris brassicae* or other lipocalins, ankyrin repeat proteins, and human fibronectin (reviewed in Binz and Plückthun, Curr Opin Biotechnol, 16: 459-69, 2005). Engineering of a scaffold protein can be regarded as grafting or integrating an affinity function onto or into the structural framework of a stably folded protein. Affinity function means a protein binding affinity according to the present invention. A scaffold can be structurally separable from the amino acid sequences conferring binding specificity. In general, proteins appearing suitable for the development of such artificial affinity reagents may be obtained by rational, or most commonly, combinatorial protein engineering techniques such as panning against AXL, either purified protein or protein displayed on the cell surface, for binding agents in an artificial scaffold library displayed in vitro, skills which are known in the art (Skerra, J. Mol. Recog., Biochim Biophys Acta, 1482: 337-350, 2000; Binz and Plückthun, Curr Opin Biotechnol, 16: 459-69, 2005). In addition, a scaffold protein having an antibody like binding activity can be derived from an acceptor polypeptide containing the scaffold domain, which can be grafted with binding domains of a donor polypeptide to confer the binding specificity of the donor polypeptide onto the scaffold domain containing the acceptor polypeptide. The inserted binding domains may include, for example, at least one CDR of an anti-AXL antibody, preferably at least one selected from the group of SEQ ID NOs: 13-30. Insertion can be accomplished by various methods known to those skilled in the art including, for example, polypeptide synthesis, nucleic acid synthesis of an encoding amino acid as well by various forms of recombinant methods well known to those skilled in the art.

As has been indicated above, the specificity of the antibody, antibody fragment, or a derivative thereof lies in the amino acid sequence of the CDR. The variable domain (the heavy chain VH and light chain VL) of an antibody preferably comprises three complementary determining regions sometimes called hypervariable regions, flanked by four relatively conserved framework regions or "FRs". Often, the specificity of an antibody is determined or largely determined by a CDR, such as a CDR of the VH chain or a plurality of CDRs. The person skilled in the art will readily appreciate that the variable domain of the antibody, antibody fragment or derivative thereof having the above-described CDRs can be used for the construction of antibodies of further improved specificity and biological function. Insofar, the present invention encompasses antibodies, antibody fragments or derivatives thereof comprising at least one CDR of the above-described variable domains and which advantageously have substantially the same, similar or improved binding properties as the antibody described in the appended examples. Starting from an antibody that comprises at least one CDR as recited in the attached sequence listing and required by the embodiments of the invention, the skilled artisan can combine further CDRs from the originally identified monoclonal antibodies or different antibodies for an enhanced specificity and/or affinity. CDR grafting is well-known in the art and can also be used to fine-tune the specific affinity and other properties of the antibody, fragment or derivative thereof of the invention, as long as the original specificity is retained. It is advantageous that the antibody, fragment or derivative comprises at least two, more preferred at least three, even more preferred at least four or at least five and particularly preferred all six CDRs of the original donor antibody. In further alternatives of the invention, CDRs from different originally identified monoclonal antibodies may be combined in a new antibody entity. In these cases, it is preferred that the three CDRs of the heavy chain originate from the same antibody whereas the three CDRs of the light chain all originate from a different (but all from the same) antibody. The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning A Laboratory Manual, Cold Spring Harbor Laboratory (1989) N.Y.

The antibodies, antibody fragments or derivative thereof are optionally deimmunized for therapeutic purposes. A deimmunized antibody is a protein devoid of or reduced for epitopes that can be recognized by T helper lymphozytes. An example how to identify said epitopes is shown in Tangri et al., (J. Immunol. 174: 3187-96, 2005). The manufacture of deimmunized antibody fragments or derivative thereof may be carried out as described in U.S. Pat. Nos. 6,054,297, 5,886,152 and 5,877,293.

In one embodiment the antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)). The production of chimeric antibodies is described, for example, in WO 89/09622.

Preferably, the present invention refers to a chimerized antibody comprising a heavy chain amino acid sequence selected from the group consisting of SEQ ID NOs: 38, 39, 41, 42 or at least the variable domain thereof or an amino acid sequence having a sequence identity of at least 90% thereto and/or a light chain amino acid sequence selected from the group consisting of SEQ. ID NOs: 37, 40 or at least the variable domain thereof or an amino acid sequence having a sequence identity of at least 90% thereto or to an antibody recognizing the same epitope on the extracellular domain of AXL.

In a further embodiment the antibodies of the present invention are humanized or fully human antibodies. Humanized forms of the antibodies may be generated according to the methods known in the art such as chimerization or CDR grafting. Alternative methods for the production of humanized antibodies are well known in the art and are described in, e.g., EP-A1 0 239 400 and WO90/07861. Generally, a humanized antibody has one or more amino acid residues introduced into it from a source which is non-human. These non-human amino acid residues are often referred to as "import" residues, which are typically taken from an "import" variable domain. Humanization can be for example performed following the method of Winter and co-workers (Jones et al., Nature, 321: 522-525 (1986); Riechmann et al., Nature, 332:323-327 (1988); Verhoeyen et al., Science, 239:1534-1536 (1988)), by substituting CDRs or CDR sequences of non human origin for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in non human antibodies.

Preferably, the present invention refers to a humanized antibody comprising a heavy chain amino acid sequence selected from the group consisting of SEQ ID NOs: 44, 46 or at least the variable domain thereof or an amino acid sequence having a sequence identity of at least 90% thereto and/or a light chain amino acid sequence selected from the group consisting of SEQ. ID NOs: 43, 45 or at least the variable domain thereof or an amino acid sequence having a sequence identity of at least 90% thereto or to an antibody recognizing the same epitope on the extracellular domain of AXL.

One method for generating fully human antibodies is through the use of XenoMouse® strains of mice that have been engineered to contain up to but less than 1000 kb sized germline configured fragments of the human heavy chain locus and kappa light chain locus. See, Mendez et al., (Nature Genetics 15:146-156 1997), and Green and Jakobovits, (J. Exp. Med. 188:483-495, 1998). The XenoMouse® strains are available from AMGEN, Inc. (formerly ABGENIX, Fremont, Calif.).

The production of the XenoMouse® strains of mice is discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430, 938, filed Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, Ser. No. 08/759,620, filed Dec. 3, 1996, U.S. Publication 2003/0093820, filed Nov. 30, 2001 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See, also European Patent No., EP 0 463 151 B1, grant published Jun. 12, 1996, International Patent Application No., WO9402602, published Feb. 3, 1994, International Patent Application No., WO9634096, published Oct. 31, 1996, WO9824893, published Jun. 11, 1998, WO0076310, published Dec. 21, 2000. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more VH genes, one or more DH genes, one or more JH genes, a mu constant region, and usually a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg and Kay, U.S. Pat. Nos. 5,591,669 and 6,023,010 to Krimpenfort and Berns, U.S. Pat. Nos. 5,612,205, 5,721,367, and 5,789, 215 to Berns et al., and U.S. Pat. No. 5,643,763 to Choi and Dunn, and GenPharm International U.S. patent application Ser. No. 07/574,748, filed Aug. 29, 1990, Ser. No. 07/575, 962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See, also European Patent No. 0 546 073 B1, International Patent Application Nos. WO9203918, WO9222645, WO9222647, WO9222670, WO9312227, WO9400569, WO9425585, WO9614436, WO9713852, and WO9824884 and U.S. Pat. No. 5,981,175, the disclosures of which are hereby incorporated by reference in their entirety.

Kirin has also demonstrated the generation of human antibodies from mice in which, through microcell fusion, large pieces of chromosomes, or entire chromosomes, have been introduced. See, European Patent Application Nos. 773 288 and 843 961, the disclosures of which are hereby incorporated by reference. Additionally, KMTM mice, which are the result of cross-breeding of Kirin's Tc mice with Medarex's minilocus (Humab) mice have been generated. These mice possess the human IgH transchromosome of the Kirin mice and the kappa chain transgene of the Genpharm mice (Ishida et al., Cloning Stem Cells 4:91-102, 2002).

Human antibodies can also be derived by in vitro methods. Suitable examples include but are not limited to phage display (CAT, Morphosys, Dyax, Biosite/Medarex, Xoma, Symphogen, Alexion (formerly Proliferon), Affimed) ribosome display (CAT), yeast display, and the like.

For therapeutic purposes, the antibody may be conjugated with a therapeutic effector group, e.g. a radioactive group or a cytotoxic group.

For diagnostic purposes, the antibody may be labelled. Suitable labels include radioactive labels, fluorescent labels, or enzyme labels.

Further antibodies to be utilized in accordance with the present invention are so-called xenogenic antibodies. The general principle for the production of xenogenic antibodies such as human antibodies in mice is described in, e.g., WO9110741, WO 9402602, WO 9634096 and WO 9633735.

As discussed above, the antibody of the invention may exist in a variety of forms besides complete antibodies; including, for example, Fv, Fab' and F(ab')$_2$ as well as in single chains; see e.g. WO8809344.

If desired, the antibodies of the invention may be mutated in the variable domains of the heavy and/or light chains to alter a binding property of the antibody. For example, a mutation may be made in one or more of the CDR regions to increase or decrease the Kd of the antibody for AXL, or to alter the binding specificity of the antibody. Techniques in site directed mutagenesis are well-known in the art. See, e.g., Sambrook et al. and Ausubel et al., supra. Furthermore, mutations may be made at an amino acid residue that is known to be changed compared to germline in a variable region of an AXL antibody. In another aspect, mutations may be introduced into one or more of the framework regions. A mutation may be made in a framework region or constant domain to increase the half-life of the AXL antibody. See, e.g., WO0009560. A mutation in a framework region or constant domain may also be made to alter the immunogenicity of the antibody, to provide a site for covalent or non-covalent binding to another molecule, or to alter such properties as complement fixation. Mutations may be made in each of the framework regions, the constant domain and the variable regions in a single mutated antibody. Alternatively, mutations may be made in only one of the framework regions, the variable regions or the constant domain in a single mutated antibody.

In a further aspect, the antibody may have a constant domain with effector functions, whereby AXL expressing cells which have bound the antibody, antibody fragment or derivative thereof on the cell surface may be attacked by immune system functions. For example, the antibody may be capable of fixing complement and participating in complement-dependent cytotoxicity (CDC). Moreover, the antibody may be capable of binding to Fc receptors on effector cells, such as monocytes and natural killer (NK) cells, and participate in antibody-dependent cellular cytotoxicity (ADCC).

In yet a further aspect the antibodies of the invention are applicable for therapeutic treatment, preferably for treatment of hyperproliferative diseases, cardiovascular diseases, in particular artheroslerosis and thrombosis, diabetes related diseases, in particular glomerular hypertrophy or diabetic nephropathy, and particularly of disorders associated with, accompanied by or caused by AXL expression, overexpression or hyperactivity. The hyperproliferative diseases are preferably selected from disorders associated with, accompanied by or caused by AXL expression, overexpression or hyperactivity, such as cancer, e.g. breast cancer, colon cancer, lung cancer, kidney cancer, follicular lymphoma, myeloid leukemia, skin cancer/melanoma, glioblastoma, ovarian cancer, prostate cancer, pancreatic cancer, Barrett's esophagus and esophageal cancer, stomach cancer, bladder cancer, cervical cancer, liver cancer, thyroid cancer, and head and neck cancer, or hyperplastic and neoplastic diseases or other AXL expressing or overexpressing hyperproliferative diseases.

In another aspect the antibodies of the present invention can be used for the co-administration with an antineoplastic agent for the treatment of one of the above mentioned disorders.

Co-administration as used herein includes the administration of an antibody of the present invention with an antineoplastic agent, preferably an apoptosis inducing antineoplastic agent. The term co-administration further includes the administration of the antibody of the present invention and the antineoplastic agent, preferably an apoptosis inducing antineoplastic agent, in the form of a single composition or in the form of two or more distinct compositions. Co-administration includes the administration of an antibody of the present invention with an antineoplastic agent, preferably an apoptosis inducing antineoplastic agent simultaneously (i.e. at the same time) or sequentially, (i.e. at intervals).

The invention further relates to a nucleic acid molecule encoding the antibody, antibody fragment or derivative thereof of the invention. The nucleic acid molecule of the invention encoding the above-described antibody, antibody fragment or derivative thereof may be, e.g. DNA, cDNA, RNA or synthetically produced DNA or RNA or recombinantly produced chimeric nucleic acid molecule comprising any of those nucleic acid molecules either alone or in combination. The nucleic acid molecule may also be genomic DNA corresponding to the entire gene or a substantial portion thereof or to fragments and derivatives thereof. The nucleotide sequence may correspond to the naturally occurring nucleotide sequence or may contain single or multiple nucleotide substitutions, deletions or additions. In a particular preferred embodiment of the present invention, the nucleic acid molecule is a cDNA molecule.

Preferably, the invention relates to an isolated nucleic acid molecule selected from the group consisting of:
(a) a nucleic acid sequence encoding a polypeptide of SEQ ID NOs: 7-12, 13-30, 37-42, 43-46

(b) a nucleic acid sequence as shown in SEQ ID NOs: 1-6, 31-36
(c) a nucleic acid complementary to any of the sequences in (a) or (b); and
(d) a nucleic acid sequence capable of hybridizing to (a), (b) or (c) under stringent conditions.

The term "hybridizing under stringent conditions" means that two nucleic acid fragments hybridize with one another under standardized hybridization conditions as described for example in Sambrook et al., "Expression of cloned genes in *E. coli*" in Molecular Cloning: A laboratory manual (1989), Cold Spring Harbor Laboratory Press, New York, USA. Such conditions are for example hybridization in 6.0×SSC at about 45° C. followed by a washing step with 2.0×SSC at 50° C., preferably 2.0×SSC at 65° C., or 0.2×SSC at 50° C., preferably 0.2×SSC at 65° C.

The invention also relates to a vector comprising a nucleic acid molecule of the invention. Said vector may be, for example, a phage, plasmid, viral or retroviral vector. Retroviral vectors may be replication competent or replication defective. In the latter case, viral propagation generally will occur only in complementing host cells.

The nucleic acid molecules of the invention may be joined to a vector containing selectable markers for propagation in a host. Generally, a plasmid vector is introduced in a precipitate such as a calcium phosphate precipitate or rubidium chloride precipitate, or in a complex with a charged lipid or in carbon-based clusters, such as fullerens. Should the vector be a virus, it may be packaged in vitro using an appropriate packaging cell line prior to application to host cells.

Preferably, the vector of the invention is an expression vector wherein the nucleic acid molecule is operatively linked to one or more control sequences allowing the transcription and optionally expression in prokaryotic and/or eukaryotic host cells. Expression of said nucleic acid molecule comprises transcription of the nucleic acid molecule, preferably into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in *E. coli*, and examples for regulatory elements permitting expression in eukaryotic host cells are the AOXI or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pCDM8, pRc/CMV, pcDNA1, pcDNA3 (Invitrogen) or pSPORTI (GIBCO BRL). Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (2001, Third Edition) N.Y. and Ausubel, Current Protocols in Molecular Biology, Green Publishing Associates and Wiley Interscience, N.Y. (1994). Alternatively, the nucleic acid molecules of the invention can be reconstituted into liposomes for delivery to target cells.

The invention further relates to a host comprising the vector of the invention. Said host may be a prokaryotic or eukaryotic cell or a non-human transgenic animal. The polynucleotide or vector of the invention which is present in the host may either be integrated into the genome of the host or it may be maintained extrachromosomally. In this respect, it is also to be understood that the nucleic acid molecule of the invention can be used for "gene targeting" and/or "gene replacement", for restoring a mutant gene or for creating a mutant gene via homologous recombination; see for example Mouellic, Proc. Nat!. Acad. Sci. USA, 87 (1990), 4712-4716; Joyner, Gene Targeting, A Practical Approach, Oxford University Press.

The host can be any prokaryotic or eukaryotic cell, such as a bacterial, insect, fungal, plant, animal, mammalian or, preferably, human cell. Preferred fungal cells are, for example, those of the genus *Saccharomyces*, in particular those of the species *S. cerevisiae*. The term "prokaryotic" is meant to include all bacteria which can be transformed or transfected with a polynucleotide for the expression of a variant polypeptide of the invention. Prokaryotic hosts may include gram negative as well as gram positive bacteria such as, for example, *E. coli, S. typhimurium, Serratia marcescens* and *Bacillus subtilis*. A polynucleotide coding for a mutant form of variant polypeptides of the invention can be used to transform or transfect the host using any of the techniques commonly known to those of ordinary skill in the art. Methods for preparing fused, operably linked genes and expressing them in bacteria or animal cells are well-known in the art (Sambrook, Molecular Cloning A Laboratory Manual, Cold Spring Harbor Laboratory (2001, Third Edition). The genetic constructs and methods described therein can be utilized for expression of variant antibodies, antibody fragments or derivatives thereof of the invention in, e.g., prokaryotic hosts. In general, expression vectors containing promoter sequences which facilitate the efficient transcription of the inserted nucleic acid molecule are used in connection with the host. The expression vector typically contains an origin of replication, a promoter, and a terminator, as well as specific genes which are capable of providing phenotypic selection of the transformed cells. The transformed prokaryotic hosts can be grown in fermentors and cultured according to techniques known in the art to achieve optimal cell growth. The antibodies, antibody fragments or derivatives thereof of the invention can then be isolated from the growth medium, cellular lysates, or cellular membrane fractions. The isolation and purification of the microbially or otherwise expressed antibodies, antibody fragments or derivatives thereof of the invention may be by any conventional means such as, for example, preparative chromatographic separations and immunological separations such as those involving the use of monoclonal or polyclonal antibodies.

In a preferred embodiment of the invention, the host is a bacterium, fungal, plant, amphibian or animal cell. Preferred animal cells include but are not limited to Chinese hamster ovary (CHO) cells, baby hamster kidney (BHK) cells, monkey kidney cells (COS), 3T3 cells, NSO cells and a number of other cell lines including human cells, for example Per.C6. In another preferred embodiment, said animal cell is an insect cell. Preferred insect cells include but are not limited to cells of the SF9 cell lines In a more preferred embodiment of the invention, said host is a human cell or human cell line. Said human cells include, but are not limited to Human embryonic kidney cells (HEK293, 293T, 293 freestyle). Furthermore, said human cell lines include, but are not limited to HeLa cells, human hepatocellular carcinoma cells (e.g., Hep G2), A549 cells.

The invention also provides transgenic non-human animals comprising one or more nucleic acid molecules of the invention that may be used to produce antibodies of the invention. Antibodies can be produced in and recovered from tissue or body fluids, such as milk, blood or urine, of goats, cows, horses, pigs, rats, mice, rabbits, hamsters or other mammals. See, e.g., U.S. Pat. Nos. 5,827,690; 5,756,687; 5,750,172; and 5,741,957. As described above, non-human transgenic animals that comprise human immunoglobulin loci can be produced by immunizing with AXL or a portion thereof.

The invention additionally relates to a method for the preparation of an antibody, comprising culturing the host of the invention under conditions that allow synthesis of said antibody and recovering said antibody from said culture.

The transformed hosts can be grown in fermentors and cultured according to techniques known in the art to achieve optimal cell growth. Once expressed, the whole antibodies, their dimers, individual light and heavy chains, or other immunoglobulin forms of the present invention, can be purified according to standard procedures of the art, including ammonium sulfate precipitation, affinity columns, column chromatography, gel electrophoresis and the like; see, Scopes, "Protein Purification", Springer-Verlag, N.Y. (1982). The antibody or its corresponding immunoglobulin chain(s) of the invention can then be isolated from the growth medium, cellular lysates, or cellular membrane fractions. The isolation and purification of the, e.g., microbially expressed antibodies or immunoglobulin chains of the invention may be by any conventional means such as, for example, preparative chromatographic separations and immunological separations such as those involving the use of monoclonal or polyclonal antibodies directed, e.g., against the constant region of the antibody of the invention.

It will be apparent to those skilled in the art that the antibodies of the invention can be further coupled to other moieties for, e.g., drug targeting and imaging applications. Such coupling may be conducted chemically after expression of the antibody or antigen to site of attachment or the coupling product may be engineered into the antibody or antigen of the invention at the DNA level. The DNAs are then expressed in a suitable host system, and. the expressed proteins are collected and renatured, if necessary.

In a preferred embodiment of the present invention, the antibody is coupled to an effector, such as a radioisotope or a toxic chemotherapeutic agent. Preferably, these antibody conjugates are useful in targeting cells, e.g. cancer cells, expressing AXL, for elimination. The linking of antibodies/ antibody fragments of the invention to radioisotopes e.g. provides advantages to tumor treatments. Unlike chemotherapy and other forms of cancer treatment, radioimmunotherapy or the administration of a radioisotope-antibody combination directly targets the cancer cells with minimal damage to surrounding normal, healthy tissue. Preferred radioisotopes include e.g. $^{3}H$, $^{14}C$, $^{15}N$, $^{35}S$, $^{90}Y$, $^{99}Tc$, $^{111}In$, $^{125}I$, $^{131}I$.

Furthermore, the antibodies of the invention can be used to treat cancer when being conjugated with toxic chemotherapeutic drugs such as geldanamycin (Mandler et al., J. Natl. Cancer Inst., 92(19), 1549-51 (2000>> and maytansin, for example, the maytansinoid drug, DM1 (Liu et al., Proc. Natl. Acad. Sci. U.S.A. 93:8618-8623 (1996) and auristatin-E or monomethylauristatin-E (Doronina et al., Nat. Biotechnol. 21:778-784 (2003) or calicheamicit). Different linkers that release the drugs under acidic or reducing conditions or upon exposure to specific proteases are employed with this technology. The antibodies of the invention may be conjugated as described in the art.

The invention further relates to a pharmaceutical composition comprising the antibody, the nucleic acid molecule, the vector, the host of the invention or an antibody obtained by the method of the invention.

The term "composition" as employed herein comprises at least one compound of the invention. Preferably, such a composition is a pharmaceutical or a diagnostic composition.

It is preferred that said pharmaceutical composition comprises a pharmaceutically acceptable carrier and/or diluent. The herein disclosed pharmaceutical composition may be partially useful for the treatment of disorders associated with, accompanied by or caused by AXL expression, overexpression or hyperactivity, e.g. hyperproliferative diseases, cardiovascular diseases, in particular artherosclerosis and thrombosis, diabetes related diseases, in particular glomerular hypertrophy or diabetic nephropathy. Said disorders comprise, but are not limited to cancer, e.g. breast cancer, colon cancer, lung cancer, kidney cancer, follicular lymphoma, myeloid leukemia, skin cancer/melanoma, glioblastoma, ovarian cancer, prostate cancer, pancreatic cancer, Barrett's esophagus and esophageal cancer, stomach cancer, bladder cancer, cervical cancer, liver cancer, thyroid cancer, and head and neck cancer, or other hyperplastic or neoplastic diseases or other AXL expressing or overexpressing diseases.

The term "hyperactivity" herein refers to uncontrolled AXL signaling which may be caused by a lack and/or dysfunction of negative regulation. By way of example negative regulation comprises protein dephosphorylation, degradation and/or endocytosis. Moreover uncontrolled AXL signaling may be the result of genetic alterations, either somatic or germline, which result in changes of the AXL amino acid sequence.

Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. The compositions of the invention may also be administered directly to the target site, e.g., by biolistic delivery to an external or internal target site, like the brain. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Proteinaceous pharmaceutically active matter may be present in amounts between 1 µg and 100 mg/kg body weight per dose; however, doses below or above this exemplary range are envisioned, especially considering the aforementioned factors. If the regimen is a continuous infusion, it should also be in the range of 1 pg to 100 mg per kilogram of body weight per minute.

Progress can be monitored by periodic assessment. The compositions of the invention may be administered locally or systemically. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents depending on the intended use of the pharmaceutical composition. It is particularly preferred that the pharmaceutical composition comprises further active agents like, e.g. an additional antineoplastic agent, small molecule inhibitor, anti-tumor agent or chemotherapeutic agent.

The invention also relates to a pharmaceutical composition comprising an anti-AXL-antibody, which is preferably the antibody of the invention in combination with at least one further antineoplastic agent. Said combination is effective, for example, in inhibiting abnormal cell growth.

Many antineoplastic agents are presently known in the art. In general the term includes all agents that are capable of prevention, alleviation and/or treatment of hyperproliferative disorders. In one embodiment, the antineoplastic agent is selected from the group of therapeutic proteins including but not limited to antibodies or immunomodulatory proteins. In another embodiment the antineoplastic agent is selected from the group of small molecule inhibitors or chemotherapeutic agents consisting of mitotic inhibitors, kinase inhibitors, alkylating agents, anti-metabolites, intercalating antibiotics, growth factor inhibitors, cell cycle inhibitors, enzymes, topoisomerase inhibitors, histone deacetylase inhibitors, anti-survival agents, biological response modifiers, anti-hormones, e.g. anti-androgens, and antiangiogenesis agents.

Specific examples of antineoplastic agents which can be used in combination with the antibodies provided herein include, for example, gefitinib, lapatinib, sunitinib, pemetrexed, bevacisumab, cetuximab, imatinib, trastuzumab, alemtuzumab, rituximab, erlotinib, bortezomib and the like. Other specific antineoplastic agents to be used in the compositions as described and claimed herein include for example, chemotherapeutic agents such as capecitabine, daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin and diethylstilbestrol (DES). See, generally, The Merck Manual of Diagnosis and Therapy, 15th Ed. 1987, pp. 1206-1228, Berkow et al., eds., Rahway, N.J. In particular preferred are such antineoplastic agents that induce apoptosis.

When used with the described AXL antibodies, such antineoplastic agents may be used individually (e.g., 5-FU and an antibody), sequentially (e.g., 5-FU and an antibody for a period of time followed by MTX and an antibody), or in combination with one or more other such antineoplastic agents (e.g., 5-FU, MTX and an antibody, or 5-FU, radiotherapy and an antibody).

The term antineoplastic agent may also include therapeutic procedures, as for example irradiation or radiotherapy.

The pharmaceutical composition of the invention can be used in human medicine and can be used also for veterinary purposes.

Additionally, the invention relates to the use of the antibody of the invention, the nucleic acid molecule, the vector, the host of the invention or an antibody obtained by the method of the invention for the preparation of a pharmaceutical composition for diagnosis, prevention or treatment of hyperproliferative diseases, cardiovascular diseases, in particular artherosclerosis and thrombosis, diabetes related diseases, in particular glomerular hypertrophy or diabetic nephropathy, and particularly of disorders associated with, accompanied by or caused by AXL expression, overexpression or hyperactivity.

A hyperproliferative disease as mentioned above includes any neoplasia, i.e. any abnormal and/or uncontrolled new growth of tissue. The term "uncontrolled new growth of tissue" as used herein may depend upon a dysfunction and/or loss of growth regulation. A hyperproliferative disease includes tumor diseases and/or cancer, such as metastatic or invasive cancers.

In a preferred embodiment of the use of the invention, said hyperproliferative disease is in particular breast cancer, colon cancer, lung cancer, kidney cancer, follicular lymphoma, myeloid leukemia, skin cancer/melanoma, glioblastoma, ovarian cancer, prostate cancer, pancreatic cancer, Barrett's esophagus and esophageal cancer, stomach cancer, bladder cancer, cervical cancer, liver cancer, thyroid cancer, and head and neck cancer, or hyperplastic or neoplastic diseases or other AXL expressing or overexpressing hyperproliferative diseases.

In yet another embodiment the present invention refers to the use of an anti-AXL-antibody, preferably the antibody of the present invention for the manufacture of a medicament for the co-administration with an antineoplastic agent for the treatment of one of the above mentioned disorders.

According to a further preferred embodiment the present invention is directed to the use of an anti-AXL antibody for the manufacture of a pharmaceutical composition for the treatment of drug resistant cancer. In a particularly preferred embodiment, the anti-AXL antibody is a monoclonal antibody as defined in claims 1-22.

Further the present invention relates to a diagnostic composition comprising the antibody of the invention, the nucleic acid molecule, the vector, the host of the invention or an antibody obtained by the method of the invention and optionally a pharmaceutically acceptable carrier.

The diagnostic composition of the invention is useful in the detection of an undesired expression, overexpression or hyperactivity of the mammalian AXL in different cells, tissues or another suitable sample, comprising contacting a sample with an antibody of the invention, and detecting the presence of AXL in the sample. Accordingly, the diagnostic composition of the invention may be used for assessing the onset or the disease status of a hyperproliferative disease.

Furthermore, malignant cells, such as cancer cells expressing AXL, can be targeted with the antibody of the invention. The cells which have bound the antibody of the invention might thus be attacked by immune system functions such as the complement system or by cell-mediated cytotoxicity, thereby reducing the number of or eradicating cancer cells. These considerations equally apply to the treatment of metastases and re-current tumors.

In another aspect of the present invention, the antibody of the invention is coupled to a labelling group. Such antibodies are particularly suitable for diagnostic applications. As used herein, the term "labelling group" refers to a detectable marker, e.g. a radiolabelled amino acid or biotinyl moieties that can be detected by marked avidin. Various methods for labelling polypeptides and glycoproteins, such as antibodies, are known in the art and may be used in performing the present invention. Examples of suitable labelling groups include, but are not limited to, the following: radioisotopes or radionuclides ($^3$H, $^{14}$C, $^{15}$N, $^{35}$S, $^{90}$Y, $^{99}$Tc, $^{111}$In, $^{125}$I, $^{131}$I) fluorescent groups (e.g. FITC, rhodamine, lanthanide phosphors), enzymatic groups (e.g. horseradish peroxidase, β-galactosidase, luciferase, alkaline phosphatase), chemiluminescent groups, biotinyl groups, or predetermined polypeptide epitopes recognized by a secondary reporter (e.g. leucine zipper pair sequences, binding sites for secondary antibodies, metal binding domains, epitope tags).

In certain aspects, it may be desirable, that the labelling groups are attached by spacer arms of various lengths to reduce potential steric hindrance.

In another embodiment the present invention relates to a method of assessing for the presence of AXL expressing cells comprising contacting the antibody of the invention with cells or a tissue suspected of carrying AXL on their/its surface. Suitable methods for detection of AXL expression in a sample may be an Enzyme-Linked Immunosorbent Assay (ELISA) or Immunohistochemistry (IHC).

An ELISA assay may be carried out in a microtiter plate format, wherein e.g. wells of a microtiter plate, are adsorbed with an AXL antibody. The wells are rinsed and treated with a blocking agent such as milk protein or albumin to prevent nonspecific adsorption of the analyte. Subsequently the wells are treated with a test sample. After rinsing away the test sample or standard, the wells are treated with a second AXL antibody that is labelled, e.g. by conjugation with biotin. After washing away excess secondary antibody, the label is detected, e.g. with avidin-conjugated horseradish peroxidase (HRP) and a suitable chromogenic substrate. The concentration of the AXL antigen in the test samples is determined by comparison with a standard curve developed from standard samples.

For IHC, paraffin-embedded tissues may be used, wherein the tissues are, e.g. first deparaffinized in xylene and then dehydrated, e.g. with ethanol and rinsed in distilled water. Antigenic epitopes masked by formalin-fixation and paraffin-embedding may be exposed by epitope unmasking, enzymatic digestion or saponin. For epitope unmasking paraffin sections may be heated in a steamer, water bath or microwave oven for 20-40 min in an epitope retrieval solution as for example 2N HCl solution (pH 1.0). In the case of an enzyme digestion, tissue sections may be incubated at 37° C. for 10-30 minutes in different enzyme solutions such as proteinase K, trypsin, pronase, pepsin etc.

After rinsing away the epitope retrieval solution or excess enzyme, tissue sections are treated with a blocking buffer to prevent unspecific interactions. The primary AXL antibody is added at appropriate concentrations. Excess primary antibody is rinsed away and sections are incubated in peroxidase blocking solution for 10 min at room temperature. After another washing step, tissue sections are incubated with a secondary labelled antibody, e.g. labelled with a group that might serve as an anchor for an enzyme. Examples therefore are biotin labelled secondary antibodies that are recognized by streptavidin coupled horseradish peroxidase. Detection of the antibody/enzyme complex is achieved by incubating with a suitable chromogenic substrate.

In an additional embodiment the present invention relates to a method of blocking AXL function comprising contacting the antibody of the invention with cells or a tissue suspected of carrying AXL on their/its surface under conditions, wherein the antibody is capable of blocking AXL function. The contacting may be in vitro or in vivo.

The invention also relates to a method of treating a hyperproliferative disease, cardiovascular diseases, in particular artherosclerosis and thrombosis, diabetes related diseases, in particular glomerular hypertrophy or diabetic nephropathy, comprising, administering to a patient in need thereof a suitable dose of the antibody or antibody fragment or derivative thereof of the present invention. The hyperproliferative disease is preferably selected from disorders associated with, accompanied by or caused by AXL expression, overexpression or hyperactivity, such as cancer, e.g. breast cancer, colon cancer, lung cancer, kidney cancer, follicular lymphoma, myeloid leukemia, skin cancer/melanoma, glioblastoma, ovarian cancer, prostate cancer, pancreatic cancer, Barrett's esophagus and esophageal cancer, stomach cancer, bladder cancer, cervical cancer, liver cancer, thyroid cancer, and head and neck cancer, or hyperplastic and neoplastic diseases or other AXL expressing or overexpressing hyperproliferative diseases.

According to another preferred embodiment of the invention the cancer to be treated is a drug resistant cancer.

The invention further relates to a method of treating a disease wherein the antibody of the invention is administered to a mammal and wherein said disease is correlated directly or indirectly with the abnormal level of expression or activity of AXL.

Finally, the invention relates to a kit comprising an anti-AXL-antibody, preferably the antibody, antibody fragment or derivative thereof of the invention, the nucleic acid molecule encoding said components and/or the vector of the invention.

All embodiments covering the compounds disclosed herein can be used as single compounds or in combination for the preparation of a medicament.

FIGURE LEGENDS

FIG. 1. Flow cytometry analysis of cell surface AXL in RatI-Mock and RatI-AXL cl.2 fibroblasts. Polyclonal RatI-Mock and clonal RatI-AXL cl.2 cells, generated by infection of RatI fibroblasts with pLXSN and pLXSN-hAXL ecotrophic virus, respectively, were collected and stained with mouse control antibody 72A1 (left panel) or mouse anti-AXL MAB154 primary antibody (right panel) at 3 μg/ml and PE-conjugated anti-mouse secondary antibody. See text for details. Staining of RatI-AXL cl.2 cells results in a shift by three orders of magnitude and demonstrates AXL overexpression on the surface of these cells.

Figure 2:
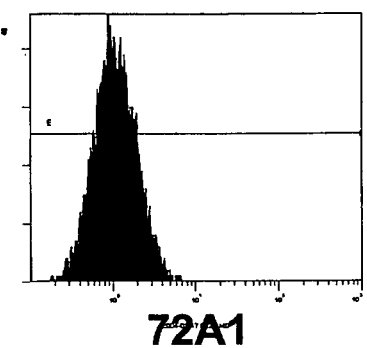
Figure 2:
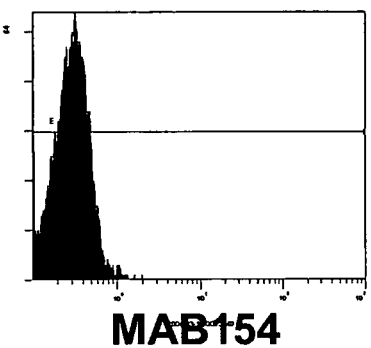
Figure 2:
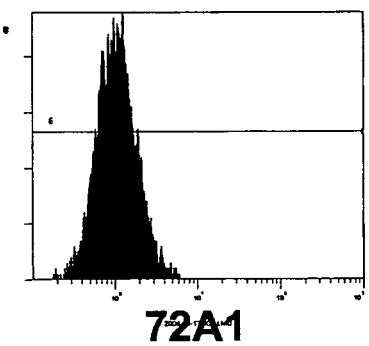
Figure 2:
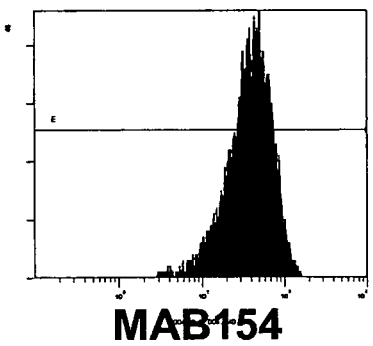

FIG. 2. Flow cytometry analysis of cell surface AXL in NIH3T3-Mock and NIH3T3-AXL cl.7 fibroblasts. Polyclonal NIH3T3-Mock and clonal NIH3T3-AXL cl.7 cells, generated by infection of NIH3T3 fibroblasts with pLXSN and pLXSN-AXL ecotrophic virus, respectively, were collected and stained with mouse control antibody 72A1 (left panel) or mouse anti-AXL MAB154 primary antibody (right panel) at 3 μg/ml and PE-conjugated anti-mouse secondary antibody. See text for details. Staining of NIH3T3-AXL cl.7 cells results in a shift by two orders of magnitude and demonstrates AXL overexpression on the surface of these cells.

Figure 3:
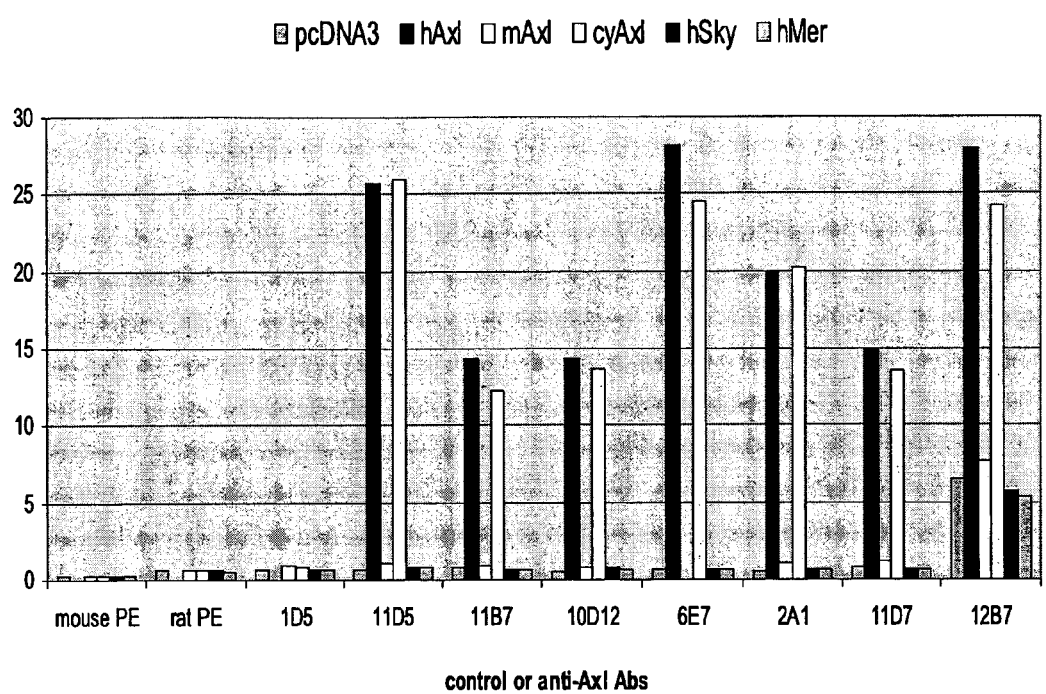

FIG. 3. Flow cytometry analysis of cross-reactivity of rat-anti AXL antibodies with mouse and cynomolgus monkey AXL as well as human Mer and Sky. HEK293T fibroblasts were transiently transfected with pcDNA3, pcDNA3-hAXL, pcDNA3 mAXL, pcDNA3-cyAXL, pcDNA3-hMer, or pcDNA3-hSky. Cells were collected and stained with 10 µg/ml anti-AXL 1 D5, 11D5, 11B7, 10D12, 6E7, 2A1, 11D7 or 12B7 primary antibody and/or PE-conjugated donkey anti-rat secondary antibody, or PE-conjugated donkey anti-mouse secondary antibody only for control. See text for details. Except 12B7 which shows moderate cross-reactivity with mouse AXL as well as human Mer and Sky, non of the anti-AXL antibodies cross-reacted with these molecules. In contrast, all tested anti-AXL antibodies cross-reacted with cynomolgus monkey AXL.

Figure 4:
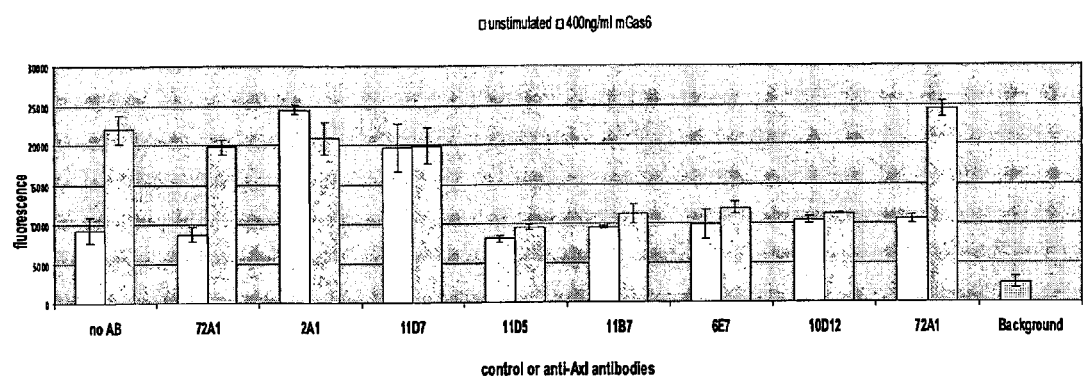
Figure 4:
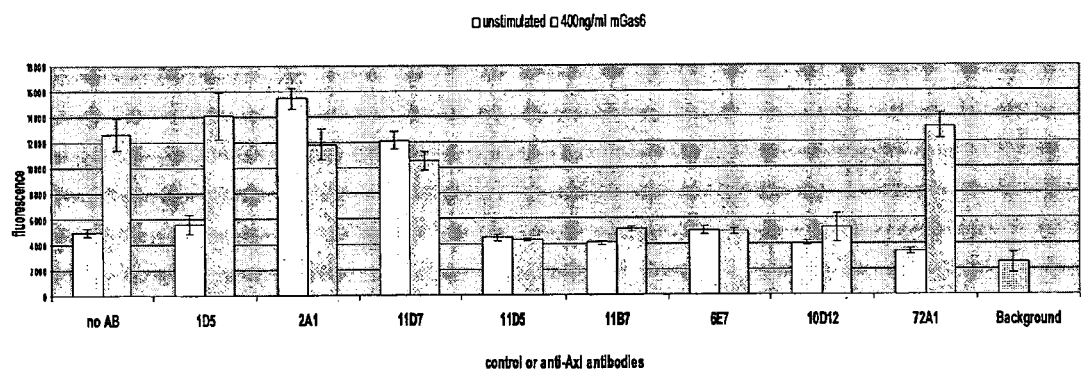

FIG. 4. ELISA experiments to investigate the effects of rat anti-AXL antibodies on AXL receptor phosphorylation. NIH3T3-AXL cl.7 fibroblasts (A) and NCI-H292 lung cancer cells (B) were starved, pre-incubated with 10 µg/ml of mouse control antibody 72A1 as well as the rat anti-AXL antibodies 2A1, 11D7, 11D5, 11B7, 6E7, or 10D12, treated with or without 400 ng/ml mGas6, and lysed. Lysates were transferred to anti-phospho-tyrosine antibody 4G10-coated Maxi-Sorp 96 well plates, which then were washed and incubated with 0.5 µg/ml biotinylated rat anti-AXL antibody 12B7, AP-conjugated streptavidin and AttoPhos substrate solution in order to collect fluorescence intensities. See text for details. The rat anti-AXL antibodies 11B7, 11D5, 6E7, and 10D12 were able to block or reduce ligand-mediated AXL activation as indicated by decreased phosphorylation, and are thus considered antagonistic anti-AXL antibodies. In contrast, the rat anti-AXL antibodies 2A1 and 11D7 stimulate basal AXL activation as indicated by increased phosphorylation, do not significantly reduce ligand-mediated AXL activation, and are therefore considered agonistic anti-AXL antibodies.

Figure 5:
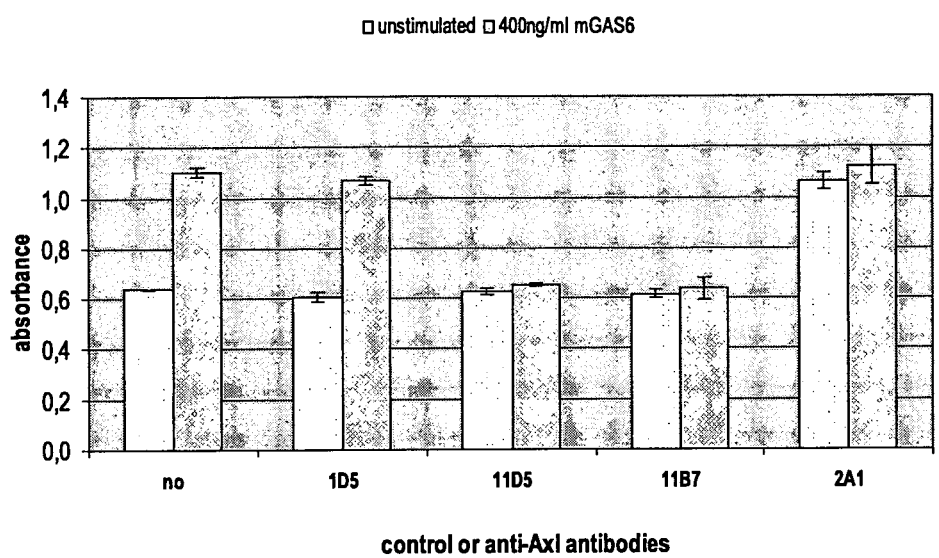

FIG. 5. ELISA experiments to investigate the effects of rat anti-AXL antibodies on p42/p44 MAP-Kinase phosphorylation. CaSki cervical cancer cells were starved, pre-incubated with 10 µg/ml of the isotypic control antibody 1D5 as well as the rat anti-AXL antibodies 11D5, 11B7, or 2A1, treated with or without 400 ng/ml mGas6, and fixed with formaldehyde. Cells were washed, quenched and incubated with anti-phospho-p44/p42 MAP Kinase (Thr202/Tyr204) primary antibody, HRP-conjugated anti-rabbit secondary antibody and Tetramethylbenzidine solution in order to measure absorbance intensities. See text for details. The rat anti-AXL antibodies 11B7 and 11D5 were able to reduce ligand-mediated p42/p44 MAP-Kinase activation as indicated by decreased phosphorylation, and are thus considered antagonistic anti-AXL antibodies. In contrast, the rat anti-AXL antibody 2A1 stimulates basal p42/p44 MAP-Kinase activation as indicated by increased phosphorylation, does not reduce ligand-mediated p42/p44 MAP-Kinase activation, and is therefore considered an agonistic anti-AXL antibody.

Figure 6:
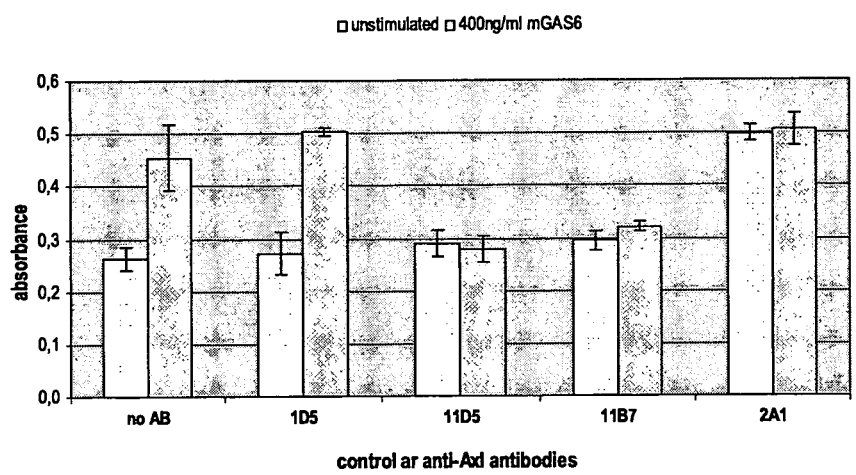
Figure 6:
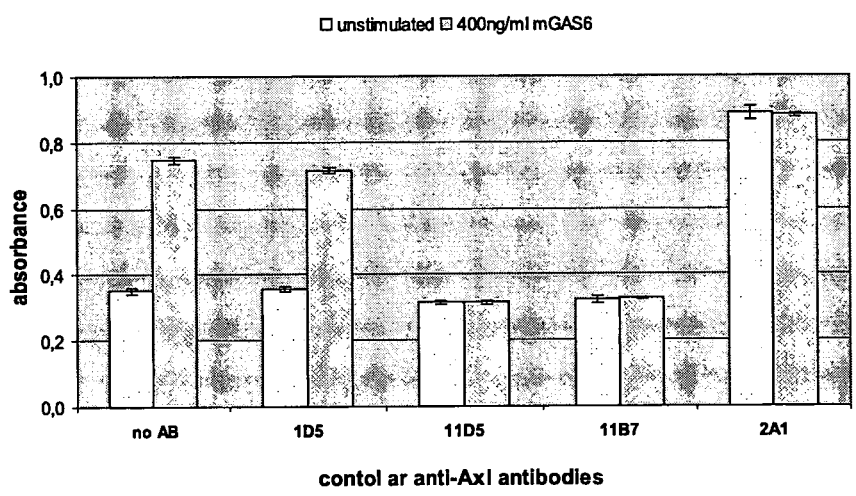

FIG. 6. ELISA experiments to investigate the effects of rat anti-AXL antibodies on Akt-Kinase phosphorylation. NIH3T3-AXL cl.7 fibroblasts (A) and CaLu-1 lung cancer cells (B) were starved, pre-incubated with 10 µg/ml of the isotypic control antibody 1 D5 as well as the rat anti-AXL antibodies 11D5, 11B7, or 2A1, treated with or without 400 ng/ml mGas6, and fixed with formaldehyde. Cells were washed, quenched and incubated with anti-phospho-Akt (Ser473) primary antibody, HRP-conjugated anti-rabbit secondary antibody and Tetramethylbenzidine solution in order to measure absorbance intensities. See text for details. The rat anti-AXL antibodies 11B7 and 11D5 were able to block or reduce ligand-mediated Akt-Kinase activation as indicated by decreased phosphorylation, and are thus considered antagonistic anti-AXL antibodies. In contrast, the rat anti-AXL antibody 2A1 stimulates basal Akt-Kinase activation as indicated by increased phosphorylation, does not reduce ligand-mediated Akt-Kinase activation, and is therefore considered an agonistic anti-AXL antibody.

Figure 7:
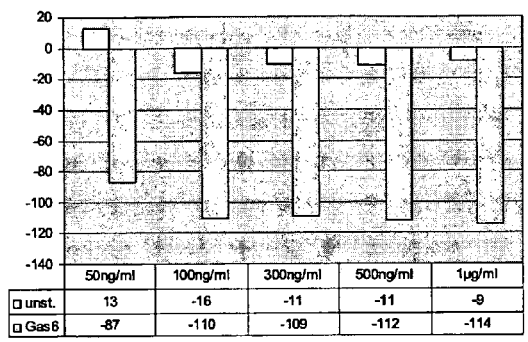
Figure 7:
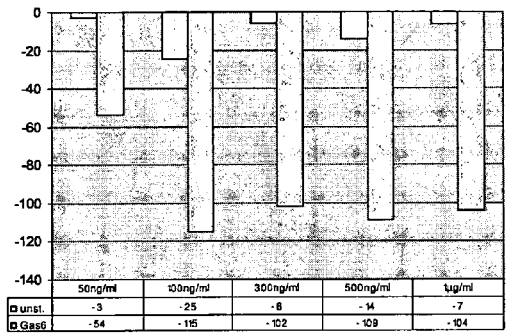
Figure 7:
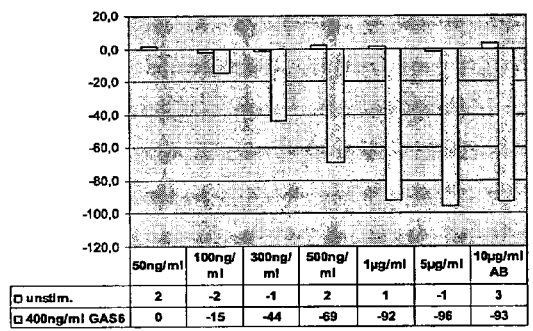
Figure 7:
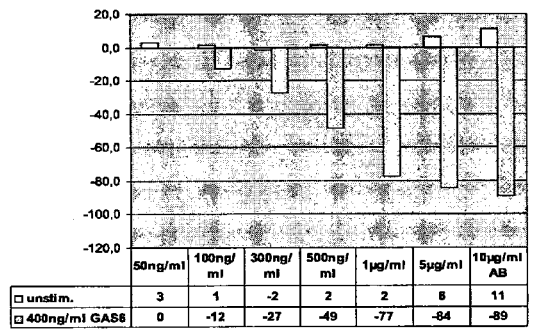

FIG. 7. ELISA experiments to compare the effects of rat and chimeric anti-AXL antibodies on Akt-Kinase phosphorylation. NIH3T3-AXL cl.7 fibroblasts were starved, pre-incubated with 50 ng/ml, 100 ng/ml, 300 ng/ml, 500 ng/ml, and 1 µg/ml of rat anti-AXL antibody 11B7 or chimeric anti-AXL 2.5 antibody ch11B7, as well as 50 ng/ml, 100 ng/ml, 300 ng/ml, 500 ng/ml, 1 µg/ml, 5 µg/ml, and 10 µg/ml of rat anti-AXL antibody 11D5 or chimeric anti-AXL antibody ch11D5, treated with or without 400 ng/ml mGas6, and fixed with formaldehyde. Cells were washed, quenched and incubated with anti-phospho-Akt (Ser473) primary antibody, HRP-conjugated anti-rabbit secondary antibody and Tetramethylbenzidine solution in order to measure absorbance intensities. See text for details. Rat anti-AXL antibody 11B7 and chimeric anti-AXL antibody ch11B7 as well as rat anti-AXL antibody 11D5 or chimeric anti-AXL antibody ch11D5 were able to inhibit ligand-mediated Akt-Kinase activation to similar extent as indicated by decreased phosphorylation. Thus, as compared to their respective rat counterparts, the chimeric anti-AXL antibodies ch11B7 and ch11D5 maintained activity.

Figure 8:
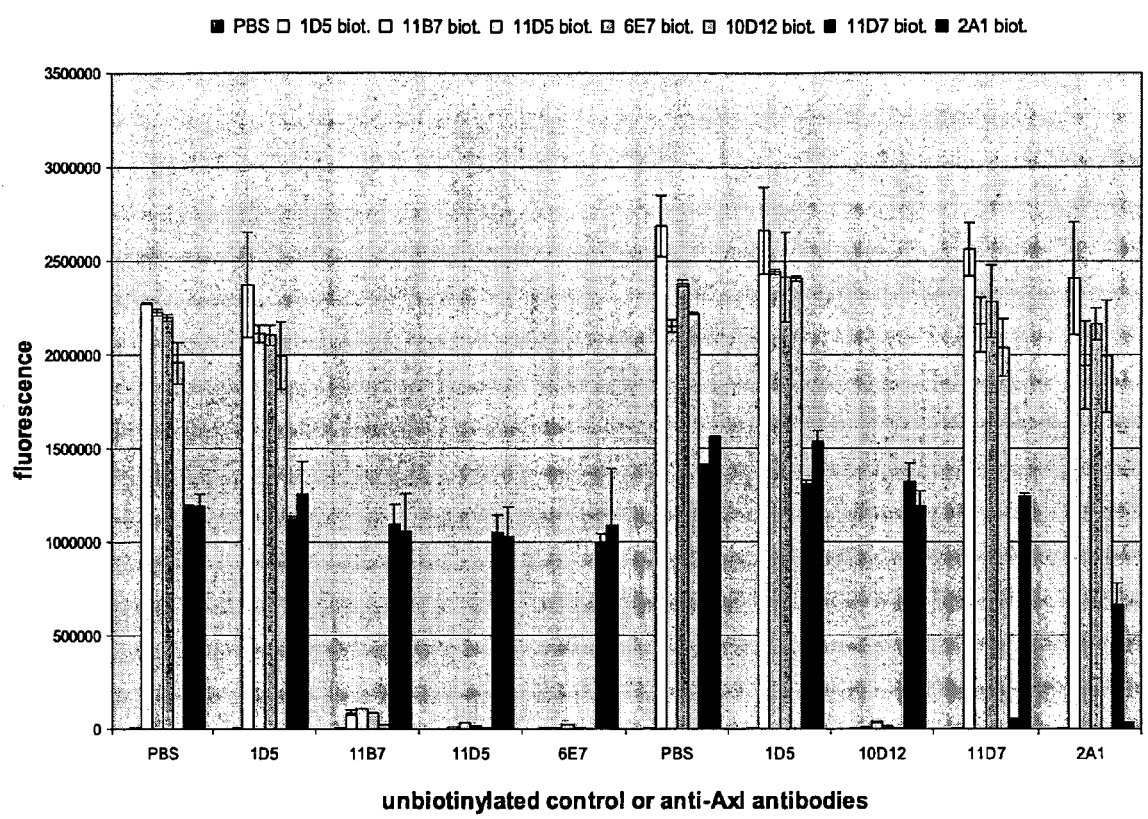

FIG. 8. Competition ELISA experiments to investigate binding properties of rat anti-AXL antibodies. 96 well Maxi-Sorp plates were coated with 1 µg/ml human AXL-ECD and pre-incubated with 10 µg/ml of unbiotinylated isotypic control antibody 1D5 or rat anti-AXL antibodies 11B7, 11D5, 6E7, 10D12, 11D7, or 2A1. After incubation with 0.5 µg/ml biotinylated isotypic control antibody 1D5 or biotinylated rat anti-AXL antibodies 11B7, 11D5, 6E7, 10D12, 11D7, or 2A1, and addition of AP-conjugated Streptavidin and AttoPhos substrate solution, fluorescence was collected to measure bound biotinylated antibodies. See text for details. The control antibody 1D5 did not bind to AXL-ECD. The antagonistic anti-AXL antibodies 11B7, 11D5, 6E7, and 10D12 competed with each other for the same or structurally adjacent epitopes. The agonistic antibodies 11D7 and 2A1 recognize different epitopes and do not compete with the antagonistic antibodies for binding to the AXL-ECD.

Figure 9:
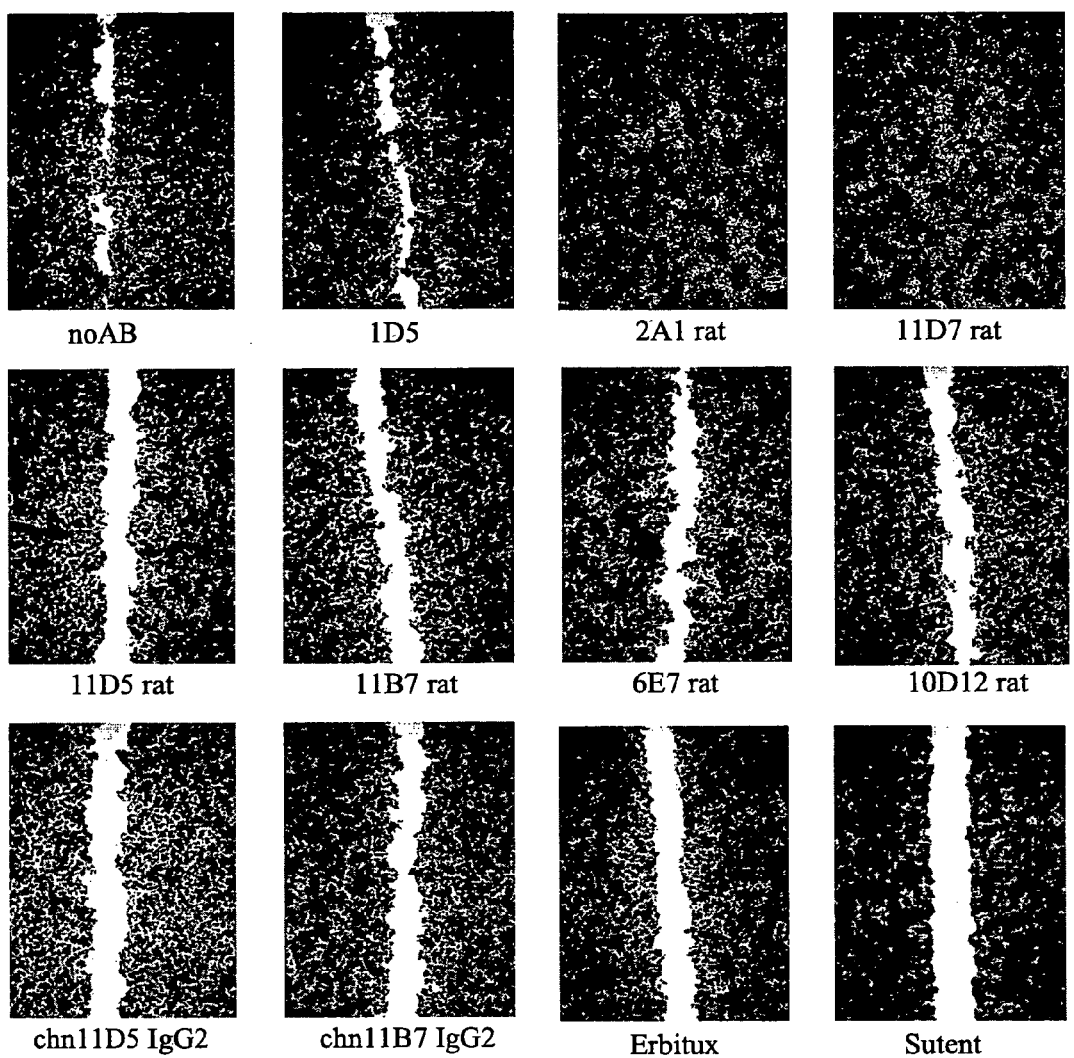

FIG. 9. Wound healing/scratch assay to investigate the effects of rat and chimeric anti-AXL antibodies on cell migration and proliferation. After grown to confluency, NCI-H292 lung cancer cells were starved and wounded with a pipette tip. In the presence of 10 µg/ml of the isotypic control antibody 1D5, the antagonistic rat anti-AXL antibodies 11D5, 11B7, 6E7, or 10D12, the chimeric anti-AXL antibodies chn11D5 IgG2 and chn11B7 IgG2, the agonistic rat anti-AXL antibodies 2A1 and 11D7, as well as 10 µg/ml of Erbitux or 5 µM Sutent, cells were permitted to re-populate the area of clearing, After 24 h, cells were fixed and stained, and photos of the wounds were taken. See text for details. Compared to the isotypic control antibody 1D5, the antagonistic rat anti-AXL antibodies 11D5, 11B7, 6E7, and 10D12, as well as the chimeric anti-AXL antibodies chn11D5 IgG2 and chn11B7 IgG2 reduced the re-population of the cleared area, whereas the agonistic rat anti-AXL antibodies 2A1 and 11D7 led to complete wound closure.

Figure 10:
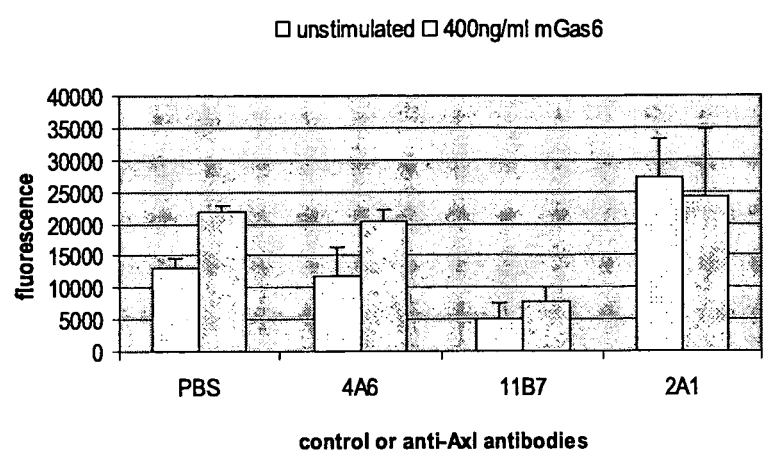

FIG. 10. Boyden chamber/transwell assay to investigate the effects of rat anti-AXL antibodies on directed cell migration. Serum starved NIH3T3-AXL cl.7 fibroblasts were pre-incubated with 10 µg/ml of the rat anti-AXL antibodies 4A6, 11B7 or 2A1, plated on top of collagen 1-coated FluoreBlock inserts and exposed to serum-free medium with or without Gas6 in the lower compartment. After 7 h, transmigrated cells were stained with calcein-AM, and fluorescence of each well was measured. See text for details. The antagonistic anti-AXL antibody 11B7 reduced both basal and Gas6-induced migration of NIH3T3-AXL cl.7 fibroblasts, whereas the agonistic rat anti-AXL antibody 2A1 increased ligand-induced and, in particular, basal migration of NIH3T3-AXL cl.7 cells. The antibody 4A6 did not affect directed cell migration.

Figure 11:
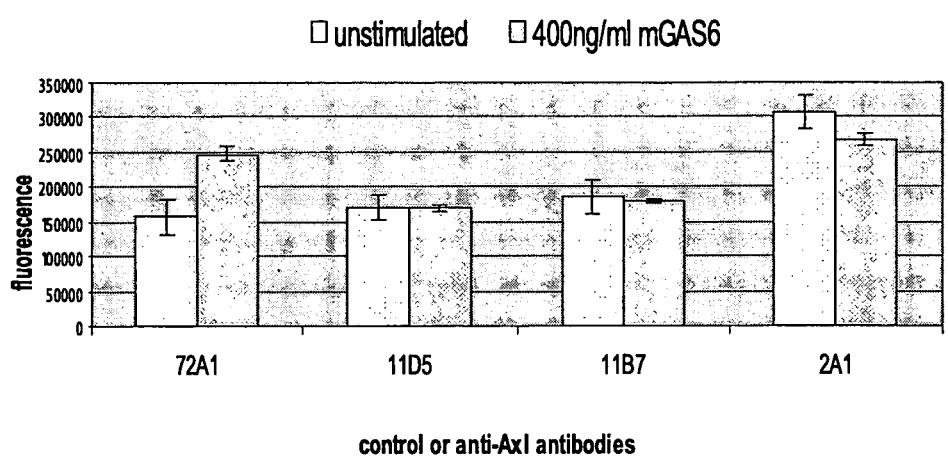

FIG. 11. AlamarBlue™ assay to investigate the effects of rat anti-AXL antibodies on Gas6-induced cell proliferation. Serum starved NIH3T3-AXL cl.7 fibroblasts were pre-incubated with 20 μg/ml of the mouse control antibody 72A1, the rat antagonistic anti-AXL antibodies 11D5 and 11B7, as well as the agonistic anti-AXL antibody 2A1, and grown in the absence or presence of 400 ng/ml Gas6. After 4 days, AlamarBlue™ was added to the cells and absorbance was measured. See text for details. The antagonistic anti-AXL antibodies 11D5 and 11B7 inhibited Gas6-induced proliferation of NIH3T3-AXL cl.7 fibroblasts, whereas the agonistic rat anti-AXL antibody 2A1 increased ligand-induced and, in particular, basal proliferation of NIH3T3-AXL cl.7 cells.

Figure 12:
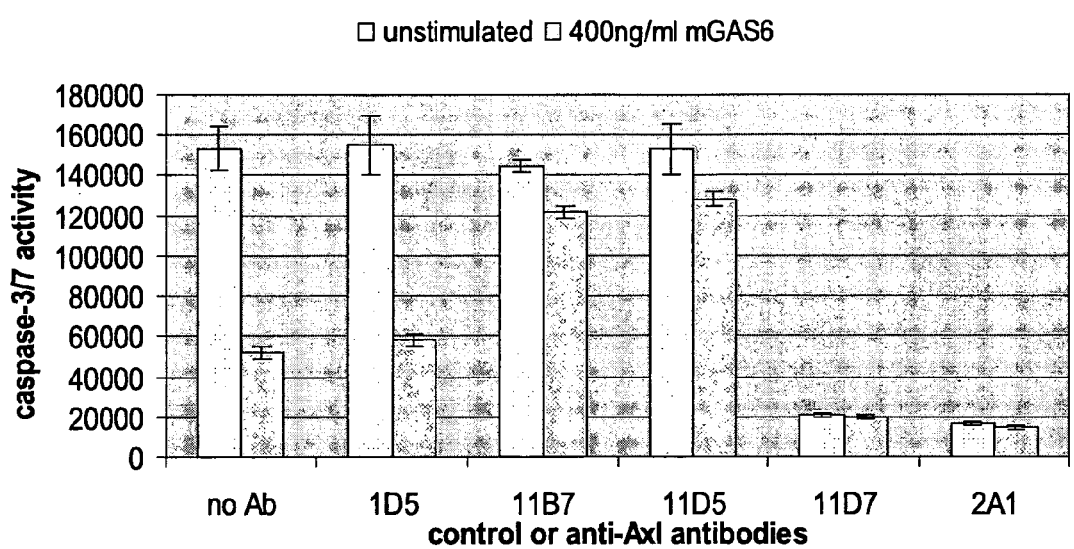

FIG. 12. Caspase-3/7 assay to investigate the effects of rat anti-AXL antibodies on Gas6-mediated anti-apoptosis. Serum-starved NIH3T3-AXL cl.7 fibroblasts were pre-incubated with 10 μg/ml of the isotypic control antibody 1D5, the antagonistic rat anti-AXL antibodies 11B7 and 11D5, or the agonistic rat anti-AXL antibodies 11D7 and 2A1, and treated with or without Gas6. Apo-ONE substrate solution was added and flourescence was collected to measure caspase-3/7 activity. See text for details. Compared to the isotypic control antibody, the antagonistic rat anti-AXL antibodies 11B7 and 11D5 reduced Gas6-mediated anti-apoptosis of serum-starved NIH3T3-AXL cl.7 fibroblasts, and thus induced apoptosis. In contrast, the agonistic rat anti-AXL antibodies 2A1 and 11D7 induced anti-apoptosis of serum-starved NIH3T3-AXL cl.7 cells regardless of the absence or presence of Gas6, and therefore inhibited apoptosis.

Figure 13:
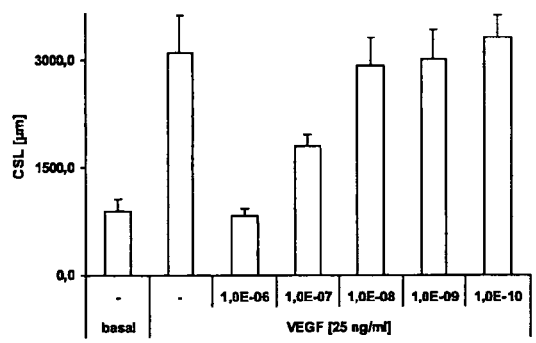
Figure 13:
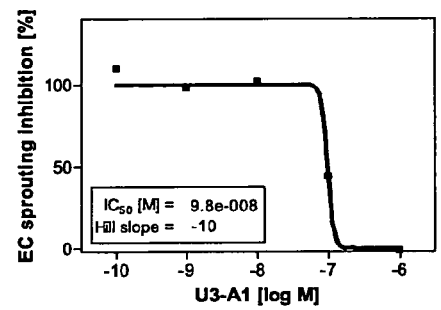
Figure 13:
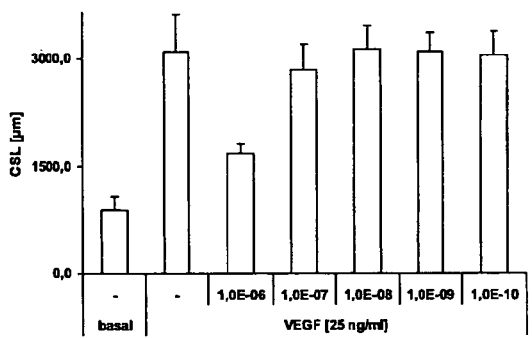
Figure 13:
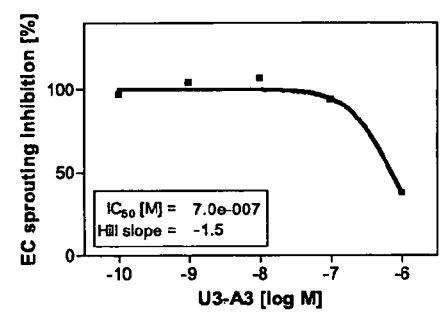

FIG. 13. Spheroid-based cellular angiogenesis assay to investigate the effects of rat anti-AXL antibodies on VEGF-A-induced endothelial cell sprouting. HUVEC spheroids were embedded in a 3D collagen gel, stimulated with 25 ng/ml VEGF-A and treated with indicated concentrations of the antagonistic rat anti-AXL antibodies 11B7 (A) and 11D5 (B) for 24 h. The mean±SEM of the cumulative sprout length of 10 randomly selected spheroids per data point was analyzed (left panel) and the relative inhibition by the antibody was determined (right panel). Fitting of $IC_{50}$ curves and calculation of $IC_{50}$ values was performed with GraphPad Prism 4.03. See text for details. The antagonistic rat anti-AXL antibodies 11B7 and 11D5 inhibited VEGF-A-stimulated HUVEC sprouting in the spheroid-based angiogenesis assay in a dose-dependent manner. Whereas treatment with the highest concentration of 11B7 reduced HUVEC sprouting to basal levels, inhibition with the highest concentration of 11D5 was not as effective (left panel). HUVEC sprouting was inhibited with $IC_{50}$ values of $9.8 \times 10^{-8}$ M and $7.0 \times 10^{-7}$ M for 11B7 and 11D5, respectively (right panel).

Figure 14:
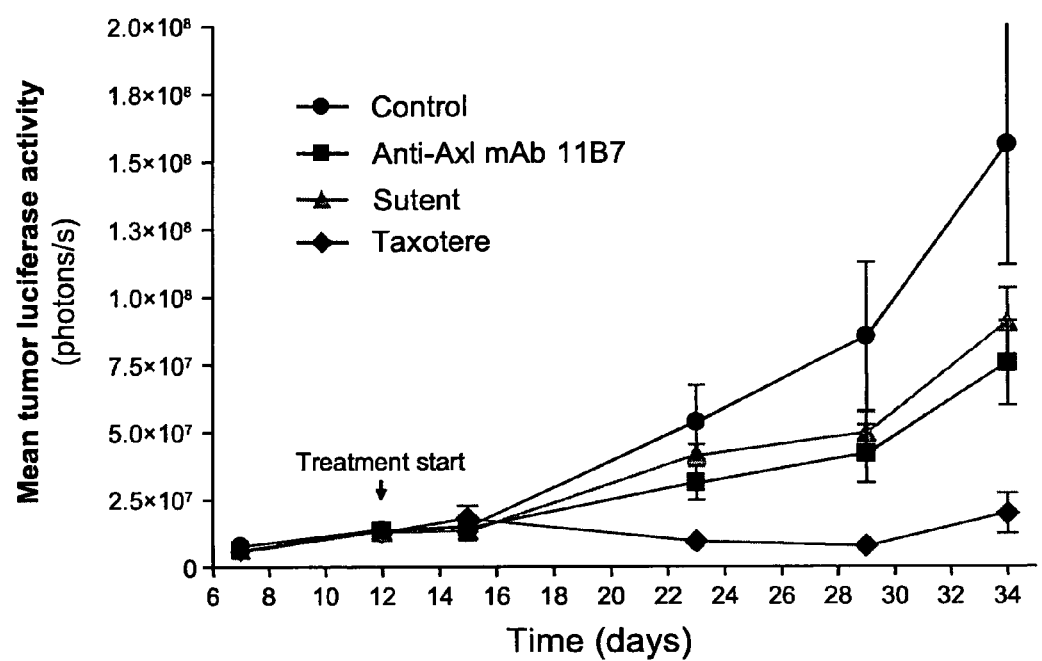

FIG. 14. Orthotopic xenograft model to investigate the effects of rat anti-AXL antibodies on human prostate carcinoma growth in nude mice. PC-3-LN prostate carcinoma cells were orthotopically implanted into the prostate of $NMRI^{-nu/nu}$ mice. Animals were randomized into 4 groups and received 25 mg/kg of the isotypic control antibody 1D5 or the antagonistic rat anti-AXL antibody 11B7, as well as 40 mg/kg Sutent or 12.5 mg/kg Taxotere. During the treatment period, the growth of orthotopically growing PC-3-LN tumors as well as peripheral metastases was monitored once weekly via in vivo bioluminescence imaging on day 15, day 23, day 29, and day 34. See text for details. Compared to the isotypic control antibody 1D5, the antagonistic rat anti-AXL antibody 11B7 reduced the overall growth of PC-3-LN prostate tumors in nude mice.

Figure 15:
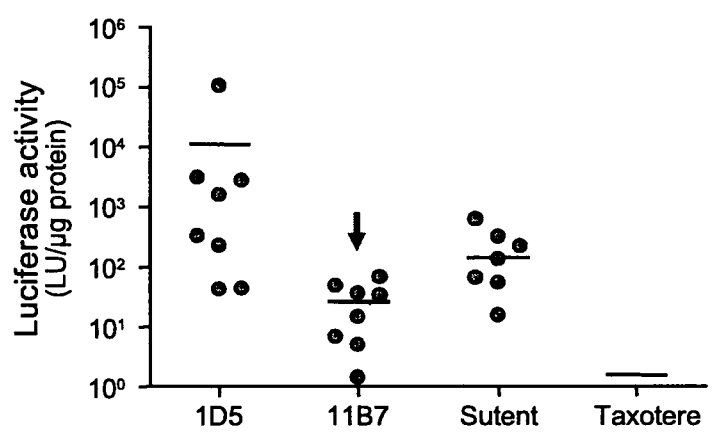

FIG. 15. Orthotopic xenograft model to investigate the effects of rat anti-AXL antibodies on human prostate carcinoma metastasis in nude mice. PC-3-LN prostate carcinoma cells were orthotopically implanted into the prostate of $NMRI^{-nu/nu}$ mice. Animals were randomized into 4 groups and received 25 mg/kg of the isotypic control antibody 1D5 or the antagonistic rat anti-AXL antibody 11B7, as well as 40 mg/kg Sutent or 12.5 mg/kg Taxotere. Post necropsy, selected organs (liver, spleen, lung, femur, and a part of the lumbar spine) were collected and analyzed for the presence of metastases via bioluminescence imaging. See text for details. Compared to the isotypic control antibody 1D5, the antagonistic rat anti-AXL antibody 11B7 of the invention reduced the occurrence of spleen metastases. Noteworthy, the anti-metastatic effect of 11B7 in this experiment was stronger than that of Sutent.

Figure 16:
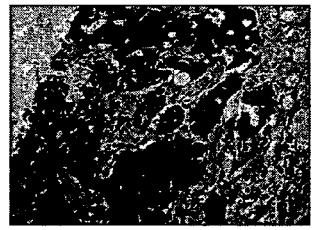
Figure 16:
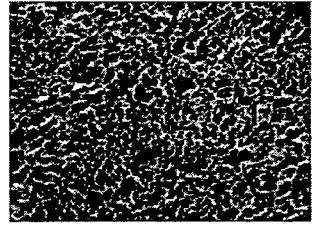

FIG. 16. Immunhistochemical analysis of AXL expression in different human malignancies. 17 human solid tumor types, each represented by pairs of tumor tissue and matching non-malignant tissue, were analyzed with regard to AXL expression by immunohistochemistry. See text for details. Results are summarized (A), whereby an intensity of 1 refers to weak staining in more than 25% of inspected cells. Examples of most intense staining as observed in mammary tumors and a signet ring cell carcinoma of the stomach are displayed (B).

Figure 17:
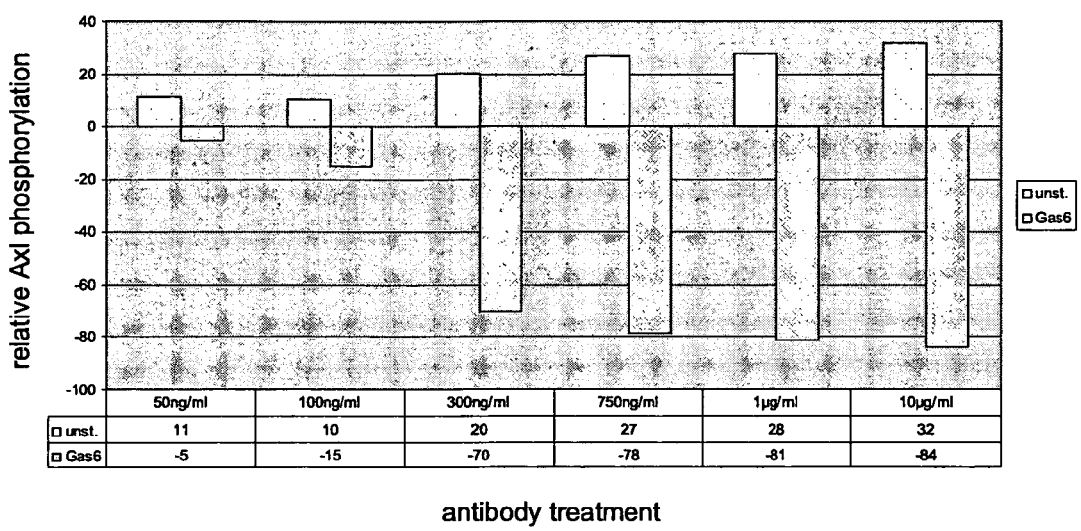
Figure 17:
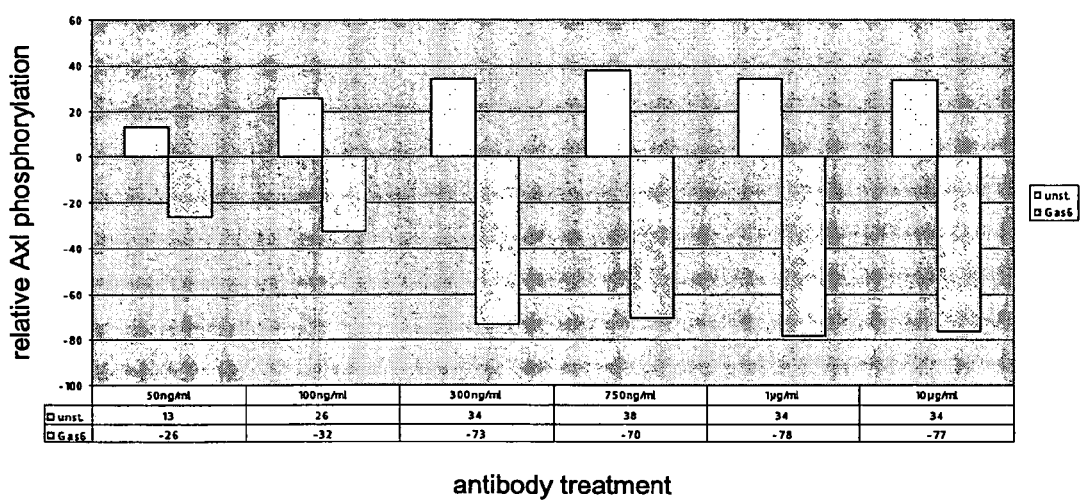

FIG. 17. ELISA experiments to compare the effects of rat and chimeric anti-Axl antibodies on Axl phosphorylation. CaSki cervical cancer cells were starved, pre-incubated with 50 ng/ml, 100 ng/ml, 300 ng/ml, 750 ng/ml, 1 μg/ml, and 10 μg/ml of rat anti-Axl antibody 11B7 (A) or chimeric anti-Axl antibody ch11B7 (B), treated with or without 400 ng/ml mGas6, and lysed. Lysates were transferred to anti-phosphotyrosine antibody 4G10-coated Maxi-Sorp 96 well plates. Afterwards, plates were washed and incubated with 0.5 μg/ml of biotinylated rat anti-Axl antibody 12B7, AP-conjugated streptavidin, and AttoPhos substrate solution in order to collect fluorescence intensities. See text for details. As demonstrated by concentration-dependent decrease of the relative Axl phosphorylation in the cervical cancer cell line CaSki, the rat anti-Axl antibody 11B7 (A) and the chimeric anti-Axl antibody ch11B7 (B) of the invention were able to block ligand-induced activation of the receptor tyrosine kinase Axl to similar extent.

Figure 18:
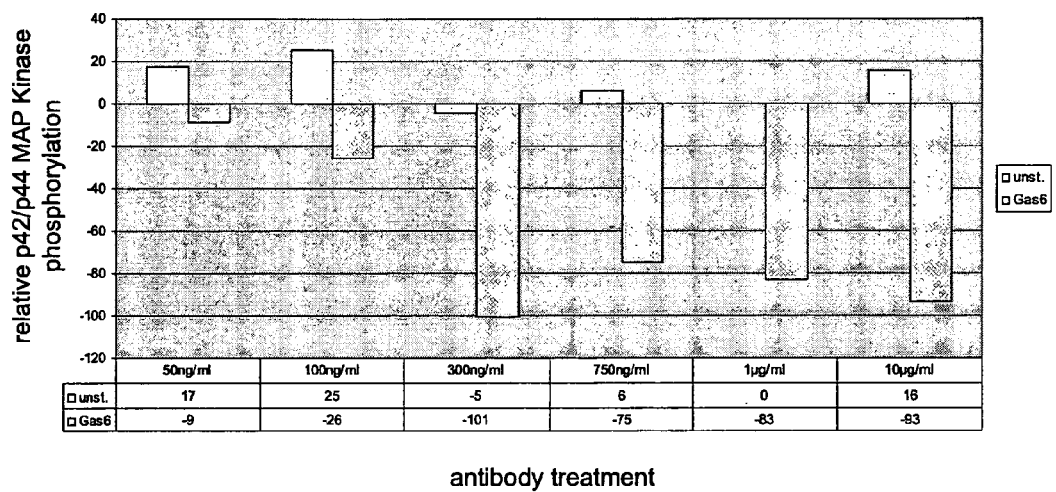
Figure 18:
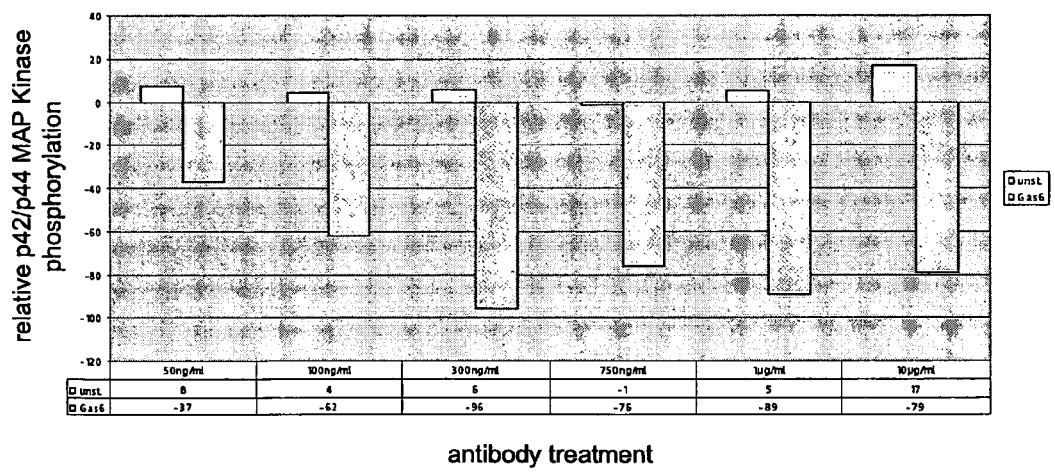

FIG. 18. ELISA experiments to compare the effects of rat and chimeric anti-Axl antibodies on Axl phosphorylation. CaSki cervical cancer cells were starved, pre-incubated with 50 ng/ml, 100 ng/ml, 300 ng/ml, 750 ng/ml, 1 μg/ml, and 10 μg/ml of rat anti-Axl antibody 11B7 (A) or chimeric anti-Axl antibody ch11B7 (B), treated with or without 400 ng/ml mGas6, and fixed with formaldehyde. Cells were washed, quenched and incubated with anti-phospho-p44/p42 MAP Kinase (Thr202/Tyr204) primary antibody, HRP-conjugated anti-rabbit secondary antibody and Tetramethylbenzidine solution in order to measure absorbance intensities. See text for details. The rat anti-Axl antibody 11B7 (A) and the chimeric anti-Axl antibody ch11B7 (B) of the invention were able to block Gash-induced activation of p42/p44 MAP-Kinase in CaSki cervical cancer cells to similar extent as indicated by concentration-dependent decrease of the relative p42/p44 MAP-Kinase phosphorylation.

Figure 19:
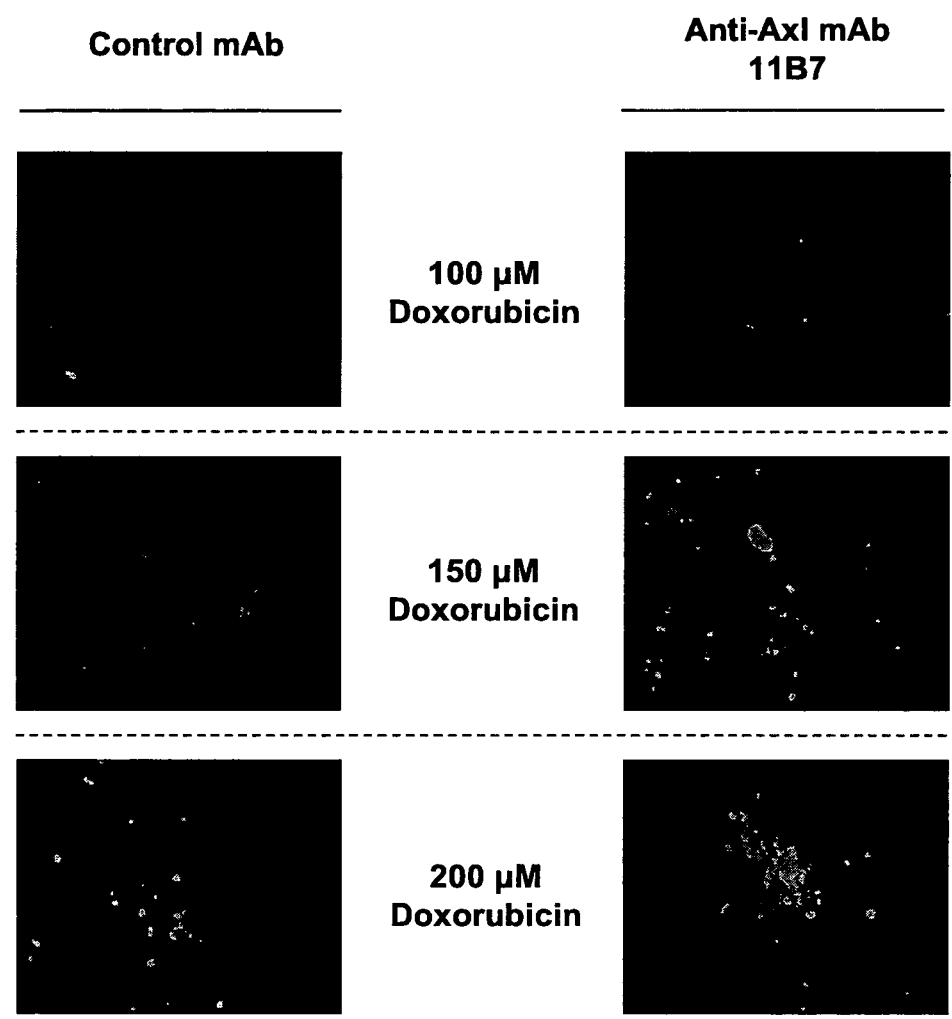

FIG. 19. TUNEL staining to investigate the combinatorial effect of rat anti-AXL antibodies and chemotherapeutic agents to overcome drug resistance in human ovarian cancer cells. Human NCI/ADR-RES ovarian cancer cells were pre-incubated with 10 µg/ml of control antibody or the antagonistic anti-Axl antibody 11B7 and co-incubated with doxorubicin at final concentrations of 100 µM, 150 µM, or 200 µM. Applying a commercially available kit, TUNEL staining was performed in order to visualize and determine apoptosis. See text for details. No TUNEL staining, and hence no apoptosis, was observed with NCI/ADR-RES ovarian cancer cells that were treated with 100 µM of doxorubicin, regardless of whether cells have been co-incubated with control antibody or the antagonistic anti-Axl antibody 11B7 (top). However, at a concentration of 150 µM of doxorubicin, only very week apoptosis could be detected in cells co-treated with control antibody, whereas co-incubation with the antagonistic anti-Axl antibody 11B7 resulted in a substantial induction of apoptosis (middle). Also in the presence of 200 µM of doxorubicin, co-incubation of cells with 11B7 significantly increased apoptosis rates as compared to cells being incubated with control IgG antibody (bottom), indicating that co-treatment of even multi drug-resistant tumor cells with both chemotherapeutic agents and antagonistic anti-Axl antibodies of the invention may be suitable to overcome drug resistance.

Figure 20:
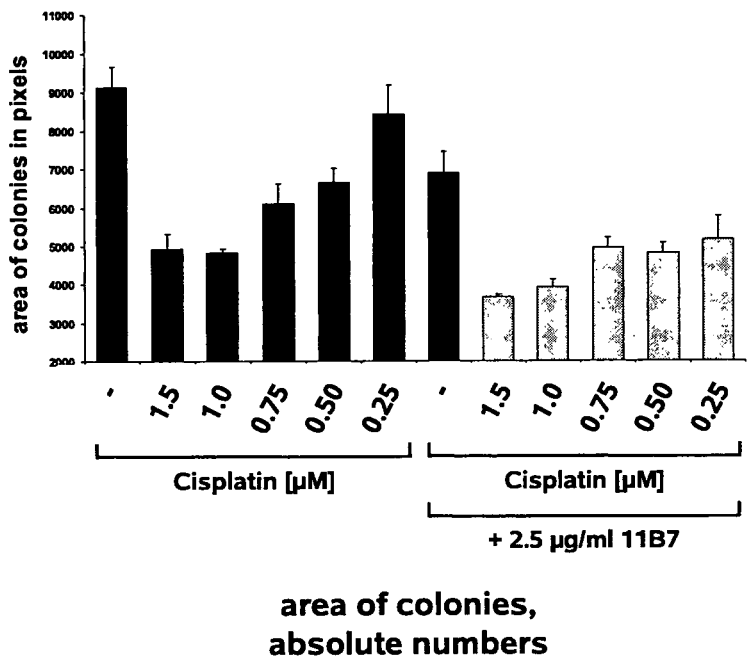
Figure 20:
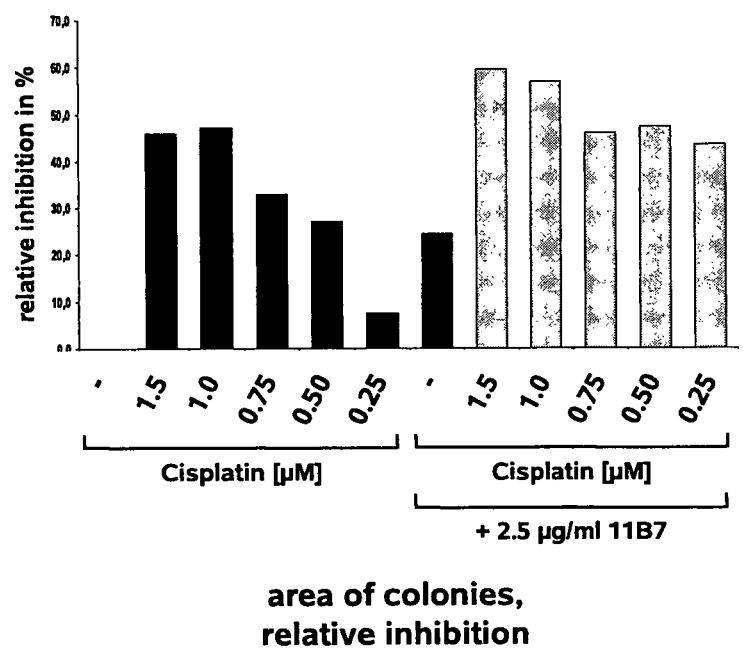

FIG. 20. Soft agar assay to investigate the combinatorial effect of rat anti-AXL antibodies and chemotherapeutic agents on anchorage-independent growth of human melanoma cells. Human C-8161 melanoma cells either remained untreated or were incubated with the rat antagonistic anti-AXL antibody 11B7 at a final concentration of 2.5 µg/ml. Combined with cisplatin at the indicated concentrations, agar-embedded cells were allowed to grow on top of a 0.7% bottom agar layer for 5 days. Stained with MTT, the area of colonies was then measured. See text for details. Absolute numbers reflecting the overall area of colonies (A) and the relative growth inhibition (B) calculated on the basis of these data are shown. As compared to untreated control cells, incubation with cisplatin led to colony growth retardation in a dose-dependent manner. In line with the inhibitory effect of 11B7 alone in the range of 30%, combination with the antagonistic anti-Axl antibody 11B7 resulted in a significantly potentiated inhibitory effect of cisplatin on soft agar growth of C-8161 melanoma cells, particularly at lower concentrations of cisplatin.

Further, the present invention shall be explained by the following examples and the accompanying drawing figures.

EXAMPLES

General Comment

The following examples, including the experiments conducted and results achieved, are provided for illustrative purposes only and are not to be construed as limiting upon the present invention.

Example 1

Generation of AXL Overexpressing RatI Fibroblasts as Immunogen and AXL Overexpressing NIH3T3 Fibroblasts as Experimental Model System The full length coding sequence for the human receptor tyrosine kinase AXL transcript variant 1 according to the National Center for Biotechnology Information (NCBI) reference sequence (NM_021913) was subcloned into pLXSN via flanking recognition elements for the restriction endonucleases EcoRI and BamHI, thereby resulting in the retroviral expression vector pLXSN-hAXL.

For the generation of antibodies that specifically bind to human receptor tyrosine kinase AXL, RatI fibroblasts stably overexpressing human AXL were generated by retroviral gene transfer. In brief, $3 \times 10^5$ Phoenix-E cells were seeded on 60 mm culture dishes and transfected with 2 µg/ml pLXSN vector or pLXSN-hAXL using the calcium phosphate method. After 24 h, medium was replaced by fresh medium in which Phoenix-E cells were incubated for 4 h. The supernatants of Phoenix-E cells releasing pLXSN or pLXSN-hAXL ecotrophic virus were harvested and used for the incubation of subconfluent RatI cells ($2 \times 10^5$ cells per 6 cm dish) for 3 h in the presence of Polybrene (4 mg/ml; Aldrich). Simultaneously, Phoenix-E cells were re-incubated with fresh medium, which after another 3 h was used for a second infection of the RatI fibroblasts in the presence of Polybrene (4 mg/ml; Aldrich). Likewise, a third infection cycle was performed. After changing the medium, selection of RatI cells with G418 was started. Usually, stable clones were picked after selection for 21 days.

A panel of stable clones was propagated and quantified for membrane-localized human AXL expression by FACS analysis. In detail, $1 \times 10^5$ cells were harvested with 10 mM EDTA in PBS, washed once with FACS buffer (PBS, 3% FCS, 0.4% azide) and seeded on a 96 well round bottom plate. The cells were spun for 3 min at 1,000 rpm to remove supernatant and were resuspended with mouse anti-AXL primary antibody MAB154 (R&D Systems, 3 µg/ml). Cell suspensions were incubated on ice for 1 h, washed twice with FACS buffer and resuspended in 100 µl/well of PE-conjugated donkey anti-mouse secondary antibody (Jackson) diluted 1:50 in FACS buffer. The cell suspensions were incubated on ice and in the dark for 30 min, washed twice with FACS buffer and analyzed using an Epics XL-MCL flow cytometer (Beckman Coulter).

FIG. 1 shows the FACS analysis of the polyclonal RatI-Mock population stably infected with pLXSN empty vector and RatI-AXL cl.2 stably infected with pLXSN-hAXL, and demonstrates AXL overexpression on the cell surface of this representative clone.

Additionally, in order to generate a suitable cellular model system for experimental purposes, NIH3T3 fibroblasts stably overexpressing AXL were generated in analogy to procedures described for RatI. In brief $3 \times 10^5$ Phoenix-E cells were seeded on 60 mm culture dishes and transfected with 2 µg/ml pLXSN vector or pLXSN-AXL cDNA using the calcium phosphate method. After 24 h, medium was replaced by fresh medium in which Phoenix-E cells were incubated for 4 h. The supernatants of Phoenix-E cells releasing pLXSN or pLXSN-hAXL ecotrophic virus were harvested and used for the incubation of subconfluent NIH3T3 cells ($2 \times 10^5$ cells per 6 cm dish) for 3 h in the presence of Polybrene (4 mg/ml; Aldrich). Simultaneously, Phoenix-E cells were re-incubated with fresh medium, which after another 3 h was used for a second infection of the NIH3T3 fibroblasts in the presence of Polybrene (4 mg/ml; Aldrich). Likewise, a third infection cycle was performed. After changing the medium, selection of NIH3T3 cells with G418 was started. Usually, stable clones were picked after selection for 21 days.

A panel of stable clones was propagated and quantified for membrane-localized AXL expression by FACS analysis. In detail, $1 \times 10^5$ cells were harvested with 10 mM EDTA in PBS, washed once with FACS buffer (PBS, 3% FCS, 0.4% azide) and seeded on a 96 well round bottom plate. The cells were spun for 3 min at 1000 rpm to remove supernatant and were resuspended with mouse anti-AXL primary antibody MAB154 (R&D Systems, 3 µg/ml). Cell suspensions were incubated on ice for 1 h, washed twice with FACS buffer and resuspended in 100 µl/well of PE-conjugated donkey anti-mouse secondary antibody (Jackson) diluted 1:50 in FACS buffer. The cell suspensions were incubated on ice and in the dark for 30 min, washed twice with FACS buffer and analyzed using an Epics XL-MCL flow cytometer (Beckman Coulter).

FIG. 2 shows the FACS analysis of the polyclonal NIH3T3-Mock population stably infected with pLXSN empty vector and NIH3T3-AXL cl.7 stably infected with pLXSN-hAXL, and demonstrates AXL overexpression on the cell surface of this representative clone.

Example 2

Generation of Rat Anti-AXL Monoclonal Antibodies

Monoclonal rat anti-AXL antibodies were raised by injection of approximately 10×10$^6$ frozen cells of RatI-AXL cl.2 both i.p. and subcutaneously into Lou/C or Long Evans rats. After an 8-week interval, a final boost was given i.p and subcutaneously 3 d before fusion. Fusion of the myeloma cell line P3X63-Ag8.653 with the rat immune spleen cells was performed according to standard procedures and yielded 105 hybridomas. After 2 weeks, first supernatants from hybridomas were collected and tested in a primary FACS screen for binding to NIH3T3-AXL cl.7 fibroblasts versus NIH3T3-Mock control cells. Clones positive for AXL binding were further cultivated. From 50 ml supernatant of these clones, antibodies were purified and re-analyzed for specific binding to AXL on NIH3T3-AXL cl.7 fibroblasts versus NIH3T3-Mock control cells. Purified antibodies specifically binding to NIH3T3-AXL cl. 7 fibroblasts but not NIH3T3-Mock control cells were furthermore tested in Akt-Kinase phosphorylation ELISAs, and ELISAs to determine the isotype were performed. For purification of rat antibodies, supernatants were spun for 20 minutes at 5,000 g and subsequently sterile filtered. 500 µl of protein G sepharose FF were added and incubated at 4° C. for at least 1 h on a spinning wheel. Sepharose was spun down, supernatant discarded and protein G matrix was washed twice with PBS prior to protein elution utilizing citrate buffer (100 mM) pH 2.1. Elution fractions were immediately rebuffered to neutral pH by adding 1M Tris pH 8.0 and dialyzed against PBS.

Of the oligoclonal antibodies tested, 91 specifically bound to NIH3T3-AXL cl. 7 fibroblasts but not NIH3T3-Mock control cells, 9 inhibited Gas6-induced Aid phosphorylation in the same cells, whereas 71 stimulated Aid phosphorylation. Four antagonistic antibodies (I11B7, I10D12, 16E7, and III11D5, in the following examples referred to as 11B7, 10D12, 6E7 and 11D5, respectively), two agonistic antibodies (I11D7 and III2A1; in the following examples referred to as 11D7 and 2A1) and one control antibody (III1D5; in the following examples referred to as 1D5) were kryoconserved and subcloned.

| Nr. | clone | subclass | FACS shift NIH3T3-pLXSN control | FACS shift NIH3T3-hAXL-CI8 |
|---|---|---|---|---|
| 1 | I 1B11 | 2a | 0.8 | 53.8 |
| 2 | I 1C8 | IgM/2a | 0.9 | 55.0 |
| 3 | I 2F3 | 2a | 0.8 | 52.4 |
| 4 | I 6E7 | 2a | 1.8 | 62.3 |
| 5 | I 7E6 | 2a | 0.8 | 47.1 |
| 6 | I 7G1 | G1 | 0.7 | 32.0 |
| 7 | I 7G11 | G1 | 3.5 | 8.8 |
| 8 | I 8E5 | G1 | 1 | 33.0 |
| 9 | I 9H3 | G1 | 0.5 | 40.4 |
| 10 | I 10A10 | IgM/2a | 0.5 | 32.6 |
| 11 | I 10D9 | 2a | 0.7 | 47.4 |
| 12 | I 10D12 | G1 | 0.5 | 37.5 |
| 13 | I 11B7 | IgM/G1/2c | 0.6 | 36.2 |
| 14 | I 11D7 | IgM/2a | 0.7 | 9.6 |
| 15 | I 12B7 | 2a/2c | 0.8 | 43.6 |
| 16 | II 2B8 | IgM/G1 | 0.6 | 2.5 |
| 17 | II 2D4 | 2a | 0.8 | 46.5 |
| 18 | II 6A5 | G1 | 0.6 | 13.1 |
| 19 | II 8A8 | 2a | 0.6 | 34.6 |
| 20 | III 1A10 | 2a | 1.4 | 54.5 |
| 21 | III 1B1 | 2a | 7.5 | 24.6 |
| 22 | III 1B3 | IgM/2a | 1.1 | 53.3 |
| 23 | III 1B6 | 2b | 1.1 | 15.3 |
| 24 | III 1B11 | 2b | 1.1 | 11.1 |
| 25 | III 1C3 | 2b | 1.0 | 24.2 |
| 26 | III 1C10 | — | 1.1 | 22.1 |
| 27 | III 1D2 | IgM/2b | 3.0 | 26.6 |
| 28 | III 11D5 | 2a | 1.5 | 8.9 |
| 29 | III 1D7 | 2b | 1.0 | 17.3 |
| 30 | III 1D11 | — | 1.1 | 10.9 |
| 31 | III 1D12 | 2b | 1.0 | 7.7 |
| 32 | III 1E7 | — | 1.1 | 81.4 |
| 33 | III 1E11 | G1/2a | 1.2 | 44.0 |
| 34 | III 1F2 | G1 | 1.2 | 42.2 |
| 35 | III 1F3 | 2b | 1.1 | 9.0 |
| 36 | III 1G2 | — | 1.0 | 30.5 |
| 37 | III 1G9 | 2a | 1.3 | 89.2 |
| 38 | III1G11 | — | 1.1 | 54.7 |
| 39 | III 1G12 | — | 1.1 | 59.4 |
| 40 | III 1H4 | IgM/2b | 1.0 | 20.0 |
| 41 | III 1H8 | 2a/2b | 1.0 | 10.1 |
| 42 | III 1H9 | 2b | 0.9 | 13.6 |
| 43 | III 2A1 | 2a | 1.0 | 36.0 |
| 44 | III 2A2 | 2b | 1.0 | 10.5 |
| 45 | III 2A4 | 2b | 1.2 | 11.8 |
| 46 | III 2B1 | 2b | 0.9 | 16.0 |
| 47 | III 2B6 | 2a/2b | 1.0 | 39.7 |
| 48 | III 2B8 | 2a | 1.0 | 53.3 |
| 49 | III 2B10 | 2b | 1.1 | 10.6 |
| 50 | III 2C12 | 2a/2b | 1.0 | 11.2 |
| 51 | III 2D1 | 2a/2b | 1.0 | 42.0 |
| 52 | III 2D3 | 2b | 0.9 | 17.8 |
| 53 | III 2D8 | 2a | 1.4 | 109.7 |
| 54 | III 2D12 | 2b | 1.8 | 16.0 |
| 55 | III 2E11 | 2b | 1.0 | 14.8 |
| 56 | III 2G4 | — | 1.0 | 8.5 |
| 57 | III 2H7 | — | 1.0 | 91.2 |
| 58 | III 3A1 | 2a | 1.5 | 82.5 |
| 59 | III 3A2 | 2b | 1.0 | 7.4 |
| 60 | III 3A3 | IgM/G1 | 2.0 | 49.6 |
| 61 | III 3B2 | — | 1.0 | 11.3 |
| 62 | III 3B3 | 2b | 0.8 | 12.4 |
| 63 | III 3B4 | IgM | 1.2 | 98.0 |
| 64 | III 3B5 | IgM/2b | 1.6 | 74.0 |
| 65 | III 3B7 | 2b | 1.8 | 13.4 |
| 66 | III 3B10 | 2a | 1.1 | 70.6 |
| 67 | III 3C3 | — | 1.3 | 45.7 |
| 68 | III 3C4 | — | 1.4 | 15.2 |
| 69 | III 3C10 | 2a | 15.2 | 83.3 |
| 70 | III 3C12 | 2b | 1.2 | 41.8 |
| 71 | III 3D2 | 2b | 0.9 | 11.8 |
| 72 | III 3D3 | 2a | 1.0 | 54.5 |
| 73 | III 3E1 | — | 1.2 | 49.7 |
| 74 | III 3E3 | 2a/2b | 1.3 | 16.0 |
| 75 | III 3E5 | 2a | 1.1 | 56.4 |
| 76 | III 3F1 | 2b | 1.0 | 9.8 |
| 77 | III 3G1 | 2a | 1.2 | 57.8 |
| 78 | III 3G3 | 2a | 1.1 | 45.7 |
| 79 | III 3G6 | 2a | 1.1 | 55.9 |

-continued

| Nr. | clone | subclass | FACS shift NIH3T3-pLXSN control | FACS shift NIH3T3-hAXL-CI8 |
|---|---|---|---|---|
| 80 | III 3H4 | 2b | 1.0 | 43.3 |
| 81 | III 3H5 | 2b | 1.2 | 11.8 |
| 82 | III 4A4 | IgM | 1.3 | 8.5 |
| 83 | III 4A5 | 2a | 1.9 | 32.8 |
| 84 | III 4A6 | 2a | 2.5 | 10.4 |
| 85 | III 4B1 | 2b | 1.9 | 10.2 |
| 86 | III 4B5 | 2b | 1.6 | 6.4 |
| 87 | III 4B6 | 2a | 1.9 | 56.8 |
| 88 | III 4B9 | IgM/2b/2c | 1.7 | 16.6 |
| 89 | III 4B11 | 2a | 1.2 | 58.1 |
| 90 | III 4C2 | — | 1.6 | 7.4 |
| 91 | III 4C8 | 2a | 12.8 | 21.3 |
| 92 | III 4D1 | — | 1.6 | 7.9 |
| 93 | III 4D9 | — | 1.1 | 31.2 |
| 94 | III 4D10 | 2a | 3.8 | 7.5 |
| 95 | III 4E11 | 2b | 1.5 | 7.6 |
| 96 | III 4F6 | — | 1.2 | 5.5 |
| 97 | III 4F8 | 2a | 1.2 | 51.3 |
| 98 | III 4F11 | IgM | 1.2 | 12.9 |
| 99 | III 4F12 | 2a | 1.1 | 52.6 |
| 100 | III 4G2 | 2a | 1.0 | 52.4 |
| 101 | III4G11 | IgM/2b | 1.1 | 8.9 |
| 102 | III 4H4 | 2b | 3.1 | 61.3 |
| 103 | III 4H5 | 2a | 2.7 | 20.0 |
| 104 | III 4H10 | IgM/2a | 1.3 | 49.2 |
| 105 | III 4H11 | IgM | 3.3 | 124.0 |

Example 3

Rat Anti-AXL Antibodies of the Invention do not Cross-React with Mouse AXL or Other Members of the Human AXL Family, Mer and Sky This example addressed cross-reactivity of rat anti-AXL antibodies of the invention with mouse and cynomolgus monkey AXL as well as with the other members of the human AXL family, human Mer and human Sky. Following subcloning of the mouse and monkey AXL coding sequence as well as human Mer and Sky into pcDNA3, each expression construct was transfected into HEK293T fibroblasts. The ability of rat anti-AXL antibodies of the invention to bind these proteins was tested by FACS analysis.

3A. Cloning of Mouse AXL

In the present study, the mouse AXL expression construct pcDNA3-mAXL was generated. The full length coding sequence of mouse AXL was polymerase chain reaction (PCR) amplified using mouse heart cDNA (Ambion) as template and appropriate primers according to the National Center for Biotechnology Information (NCBI) reference sequence (NM_009465) of mouse AXL. The full length sequence coding for mouse AXL was thereby covered by two overlapping PCR fragments, a 5'-fragment and 3'-fragment. The primers for amplification of these fragments were as follows:

Forward primer MOUSE1 for the 5'-fragment carrying an EcoRI recognition sequence:

(SEQ ID NO: 69)
5'- GCG AAT TCG CCA CCA TGG GCA GGG TCC CGC TGG CCT G- 3'

Reverse primer MOUSE2 for the 5'-fragment:

(SEQ ID NO: 70)
5'- CAG CCG AGG TAT AGG CTG TCA CAG ACA CAG TCA G- 3'

Forward primer MOUSE3 for the 3'-fragment:

(SEQ ID NO: 71)
5'- GCA CCC TGT TAG GGT ACC GGC TGG CAT ATC- 3'

Reverse primer MOUSE4 for the 3'-fragment carrying a NotI recognition sequence:

(SEQ ID NO: 72)
5'- ATA AGA ATG CGG CCG CTC AGG CTC CGT CCT CCT GCC CTG- 3'

The 5'-fragment was digested with EcoRI and BstEII, the 3'-fragment was digested with BstEII and NotI, and pcDNA3 was cleaved with EcoRI and NotI. A three factor ligation of the isolated and purified fragments was performed and transformed into DH5α bacterial cells. A single colony was picked and grown in the presence of ampicillin. Using a commercially available plasmid purification kit (Qiagen), the mouse AXL expression vector pcDNA3-mAXL was purified, and sequence verified for subsequent transient transfection into HEK293T cells.

3B. Cloning of Cynomolgus Monkey AXL

In the present study, the cynomolgus monkey AXL expression constructs pcDNA3-cyAXL was generated. The full length coding sequence of cynomolgus monkey AXL was PCR amplified using cDNA prepared from cynomolgus monkey brain tissue as template. Since the nucleotide sequence of cynomolgus monkey AXL was not available, respective primers were designed assuming significant homology to human AXL. The full length sequence coding for cynomolgus monkey AXL was thereby covered by two overlapping PCR fragments, a 5'-fragment and 3'-fragment. The primers for amplification of these fragments were as follows:

Forward primer CYNO1 for the 5'-fragment carrying an EcoRI recognition sequence:

(SEQ ID NO: 73)
5'-CGG AAT TCG CCA CCA TGG CGT GGC GGT GCC CCA G-3'

Reverse primer CYNO2 for the 5'-fragment:

(SEQ ID NO: 74)
5'-CTC TGA CCT CGT GCA GAT GGC AAT CTT CAT C-3'

Forward primer CYNO3 for the 3'-fragment:

(SEQ ID NO: 75)
5'-GTG GCC GCT GCC TGT GTC CTC ATC-3'

Reverse primer CYNO4 for the 3'-fragment carrying a NotI recognition sequence:

(SEQ ID NO: 76)
5'-ATA AGA ATG C GG CCG CTC AGG CAC CAT CCT CCT GCC CTG-3'

The 5'-fragment was digested with EcoRI and DraIII, the 3'-fragment was digested with DraIII and NotI, and pcDNA3 was cleaved with EcoRI and NotI. A three factor ligation of the isolated and purified fragments was performed and transformed into DH5α bacterial cells. A single colony was picked and grown in the presence of ampicillin. Using a commercially available plasmid purification kit (Qiagen), the cynomolgus monkey AXL expression vector pcDNA3-cyAXL was purified, and sequence verified for subsequent transient transfection into HEK293T cells. The nucleotide and amino acid sequences of cynomolgus monkey are as follows:

Nucleotide sequence: (SEQ ID NO: 83)

ATGGCGTGGCGGTGCCCCAGGATGGGCAGGGTCCCGCTGGCCTGGTG
CTTGGCGCTGTGCGGCTGGGTGTGCATGGCCCCCAGGGGCACACAGG
CTGAAGAAAGTCCTTTCGTGGGTAACCCAGGGAATATCACAGGTGCCC
GGGGACTCACGGGCACCCTTCGGTGTCAGCTCCAGGTTCAGGGAGAG
CCCCCCGAGGTACACTGGCTTCGGGACGGACAGATCCTGGAGCTCGC
GGACAGTACCCAGACCCAGGTGCCCCTGGGTGAAGATGAGCAGGATGA
CTGGATAGTGGTCAGCCAGCTCAGAATCGCCTCCCTACAGCTTTCCGAC
GCGGGACAGTACCAGTGTTTGGTGTTTCTGGGACATCAGAACTTCGTGT
CCCAGCCTGGCTACGTAGGGCTGGAGGGCTTACCTTACTTCCTGGAGG
AGCCTGAGGACAGGACTGTGGCCGCCAACACCCCCTTCAACCTGAGCT
GCCAAGCCCAGGGACCCCCAGAGCCCGTGGACCTACTCTGGCTCCAG
GATGCTGTCCCCCTGGCCACAGCTCCAGGTCATGGTCCCCAGCGCAAC
CTGCATGTTCCAGGGCTGAACAAGACATCCTCTTTCTCCTGCGAAGCCC
ATAACGCCAAGGGAGTCACCACATCCCGCACGGCCACCATCACAGTGC
TCCCCCAGCAGCCCCGTAACCTCCATCTGGTCTCCCGCCAACCCACGG
AGCTGGAGGTGGCTTGGACTCCAGGCCTGAGCGGCATCTACCCCCTGA
CCCACTGCACCCTGCAGGCTGTGCTGTCAGACGATGGGATGGGCATCC
AGGCGGGAGAACCAGACCCCCAGAGGAGCCCCTCACCTTGCAAGCAT
CTGTGCCCCCCCACCAGCTTCGGCTGGGCAGCCTCCATCCTCACACCC
CTTATCACATCCGTGTGGCATGCACCAGCAGCCAGGGCCCCTCATCCT
GGACACACTGGCTTCCTGTGGAGACGCCGGAGGGAGTGCCCCTGGGC
CCCCCTGAGAACATTAGTGCCACGCGGAATGGGAGCCAGGCCTTCGTG
CATTGGCAGGAGCCCCGGGCGCCCCTGCAGGGTACCCTGTTAGGGTA
CCGGCTGGCGTATCAAGGCCAGGACACCCCAGAGGTGCTAATGGACAT
AGGGCTAAGGCAAGAGGTGACCCTGGAGCTGCAGGGGGACGGGTCTG
TGTCCAATCTGACAGTGTGTGTGGCAGCCTACACTGCTGCTGGGGATG
GACCCTGGAGCCTCCCAGTACCCCTGGAGGCCTGGCGCCCAGGGCAA
GCACAGCCAGTCCACCAGCTGGTGAAGGAAACTTCAGCTCCTGCCTTC
TCGTGGCCCTGGTGGTATATACTGCTAGGAGCAGTCGTGGCCGCTGCC
TGTGTCCTCATCTTGGCTCTCTTCCTTGTCCACCGGCGAAAGAAGGAGA
CCCGTTATGGAGAAGTGTTCGAGCCAACAGTGGAAAGAGGTGAACTGG
TAGTCAGGTACCGCGTGCGCAAGTCCTACAGTCGCCGGACCACTGAAG
CTACCTTGAACAGCCTGGGCATCAGTGAAGAGCTGAAGGAGAAGCTGC

GGGATGTGATGGTGGACCGGCACAAGGTGGCCCTGGGGAAGACTCTG
GGAGAAGGAGAGTTTGGAGCCGTGATGGAAGGCCAGCTCAACCAGGA
CGACTCCATCCTCAAGGTGGCTGTGAAGACAATGAAGATTGCCATCTGC
ACAAGGTCAGAGCTGGAGGATTTCCTGAGTGAAGCAGTCTGCATGAAG
GAATTCGACCATCCCAATGTCATGAGGCTCATCGGTGTCTGTTTCCAGG
GTTCTGAACGAGAGAGCTTTCCAGCACCTGTGGTCATCTTACCTTTCAT
GAAGCATGGAGACCTACACAGCTTCCTCCTCTATTCCCGGCTTGGGGA
CCAGCCAGTGTACCTGCCCACTCAGATGCTAGTGAAGTTCATGGCGGA
CATCGCCAGTGGCATGGAATATCTGAGTACCAAGAGATTCATACACCGG
GACCTGGCGGCCAGGAACTGCATGCTGAATGAGAACATGTCCGTGTGT
GTGGCGGACTTCGGGCTCTCCAAGAAGATCTACAACGGGGACTACTAC
CGCCAGGGACGTATCGCCAAGATGCCAGTCAAGTGGATTGCCATTGAG
AGTCTAGCTGACCGTGTCTACACGAGCAAGAGTGATGTGTGGTCCTTC
GGGGTGACAATGTGGGAGATTGCCACAAGAGGCCAAACCCCATATCCA
GGCGTGGAGAACAGCGAGATTTATGACTATCTGCGCCAGGGAAATCGC
CTGAAGCAGCCTGCGGACTGTCTGGATGGACTGTATGCCTTGATGTCG
CGGTGCTGGGAGCTAAATCCCAGGACCGGCCAAGTTTTACAGAGCTG
CGGGAAGATTTGGAGAACACACTGAAGGCCTTGCCTCCTGCCCAGGAG
CCTGACGAAATCCTCTATGTCAACATGGATGAAGGTGGAGGTTATCCTG
AACCTCCCGGCGCTGCTGGAGGAGCTGACCCCCCAACCCAGCTAGACC
CTAAGGATTCCTGTAGCTGCCTCACTTCGGCTGAGGTCCATCCTGCTGG
ACGCTATGTCCTCTGCCCTTCCACAGCCCCTAGCCCCGCTCAGCCTGC
TGATAGGGGCTCCCCAGCAGCCCCAGGGCAGGAGGATGGTGCC

Amino acid sequence: (SEQ ID NO: 84)

MAWRCPRMGRVPLAWCLALCGWVCMAPRGTQAEESPFVGNPGNITGARG
LTGTLRCQLQVQGEPPEVHWLRDGQILELADSTQTQVPLGEDEQDDWIV
VSQLRIASLQLSDAGQYQCLVFLGHQNFVSQPGYVGLEGLPYFLEEPED
RTVAANTPFNLSCQAQGPPEPVDLLWLQDAVPLATAPGHGPQRNLHVPG
LNKTSSFSCEAHNAKGVTTSRTATITVLPQQPRNLHLVSRQPTELEVAW
TPGLSGIYPLTHCTLQAVLSDDGMGIQAGEPDPPEEPLTLQASVPPHQL
RLGSLHPHTPYHIRVACTSSQGPSSWTHWLPVETPEGVPLGPPENISAT
RNGSQAFVHWQEPRAPLQGTLLGYRLAYQGQDTPEVLMDIGLRQEVTLE
LQGDGSVSNLTVCVAAYTAAGDGPWSLPVPLEAWRPGQAQPVHQLVKET
SAPAFSWPWWYILLGAVVAAACVLILALFLVHRRKKETRYGEVFEPTVE
RGELVVRYRVRKSYSRRTTEATLNSLGISEELKEKLRDVMVDRHKVALG
KTLGEGEFGAVMEGQLNQDDSILKVAVKTMKIAICTRSELEDFLSEAVC
MKEFDHPNVMRLIGVCFQGSERESFPAPVVILPFMKHGDLHSFLLYSRL
GDQPVYLPTQMLVKFMADIASGMEYLSTKRFIHRDLAARNCMLNENMSV
CVADFGLSKKIYNGDYYRQGRIAKMPVKWIAIESLADRVYTSKSDVWSF

-continued
GVTMWEIATRGQTPYPGVENSEIYDYLRQGNRLKQPADCLDGLYALMSR

CWELNPQDRPSFTELREDLENTLKALPPAQEPDEILYVNMDEGGGYPEP

PGAAGGADPPTQLDPKDSCSCLTSAEVHPAGRYVLCPSTAPSPAQPADR

GSPAAPGQEDGA

3C. Cloning of Human Mer

In the present study, the human Mer expression construct pcDNA3-hMer was generated. The full length coding sequence of human Mer was obtained through cleavage of the vector pCMV6-XL4-human Mer (Origene #TC116132) with EcoRI and XbaI. After digestion of pcDNA3 with the same restriction endonucleases, both fragments were ligated to generate pcDNA3-hMer. In order to introduce a Kozak consensus sequence, the 5'-region of the human Mer coding sequence in pcDNA3-hMer was PCR amplified using appropriate primers according to the NCBI reference sequence (NM_006343) of human Mer. The primers for amplification of this fragment were as follows:

Forward primer MER1 carrying an EcoRI recognition sequence and the Kozak consensus sequence:

```
                                       (SEQ ID NO: 77)
5'-CGG AAT TCG CCA CCA TGG GGC CGG CCC CGC TGC

CGC-3'
```

Reverse primer MER2 for the 5'-fragment:

```
                                       (SEQ ID NO: 78)
5'-TCG GCT GCC ATT CTG GCC AAC TTC C-3'
```

The PCR product and pcDNA3-hMer were digested with EcoRI and EcoRV and ligated to generate pcDNA3-Kozak-hMer, in which the full length human Mer coding sequence is preceded by a Kozak consensus sequence. Transformed into DH5α bacterial cells, a single colony was picked and grown in the presence of ampicillin. Using a commercially available plasmid purification kit (Qiagen), the pcDNA3-Kozak-hMer expression vector was purified, and sequence verified for subsequent transient transfection into HEK293T cells.

3D. Cloning of Human Sky

In the present study, the human Sky expression construct pcDNA3-hSky was generated. The full length coding sequence of human Sky was PCR amplified using the vector pCMV6-XL4-human Sky (Origene #MG1044_A02) as template and appropriate primers according to the NCBI reference sequence (NM_006293) of human Sky. The primers for amplification were as follows:

Forward primer SKY1 carrying an EcoRI recognition sequence:

```
                                       (SEQ ID NO: 79)
5'-CGG AAT TCG CCA CCA TGG CGC TGA GGC GGA GC-3'
```

Reverse primer SKY2 carrying a XhoI recognition sequence:

```
                                       (SEQ ID NO: 80)
5'-GCC CTC GAG CTA ACA GCT ACT GTG TGG CAG TAG-3'
```

The PCR product and pcDNA3 were digested with EcoRI and XhoI and ligated to generate the pcDNA3-hSky expression vector. Transformed into DH5α bacterial cells, a single colony was picked and grown in the presence of ampicillin. Using a commercially available plasmid purification kit (Qiagen), the pcDNA3-hSky expression vector was purified, and sequence verified for subsequent transient transfection into HEK293T cells.

3E. Transfection and Expression of Mouse AXL, Cynomolgus Monkey AXL, Human Mer, and Human Sky For transient expression of mouse AXL, cynomolgus monkey AXL, human Mer or human Sky, HEK293T cells were transiently transfected with either pcDNA3 empty vector, pcDNA3-hAXL, pcDNA3 mAXL, pcDNA3-cyAXL, pcDNA3-hMer, or pcDNA3-hSky applying the calcium phosphate method. In brief, prior to transfection, $3\times10^6$ HEK293T cells in 16 ml medium were seeded on a 15 cm cell tissue culture dish and grown at 7% $CO_2$ and 37° C. for 30 h. 32 µg DNA of the respective expression construct or empty vector in 720 µl of ddH$_2$O were mixed with 2.5 M $CaCl_2$ and 2×BBS (pH 6.96) and kept at room temperature for 10 min. The solutions were gently added to the cell cultures and incubated at 3% $CO_2$ and 37° C. for 8 h. The medium then was replaced with fresh growth medium and cells were cultured at 7% $CO_2$ and 37° C. for 24 h.

3F. FACS Analysis to Test Rat Anti-AXL Antibodies for Cross-Reactivity

For FACS analysis, $2\times10^5$ cells were harvested with 10 mM EDTA in PBS, washed once with FACS buffer (PBS, 3% FCS, 0.4% azide) and seeded on a 96 well round bottom plate. To remove the supernatant, plates were spun for 3 min at 1000 rpm and cells were resuspended in 10 µg/ml isotypic control antibody 1D5 as well as anti-AXL 11D5, 11B7, 10D12, 6E7, 2A1, 11D7 and 12B7 primary antibody solutions (100 µl/well). After incubation on ice for 1 h, cells were washed twice with chilled FACS buffer and resuspended with PE-conjugated donkey anti-rat (Jackson) secondary antibody diluted 1:50 in FACS buffer (100 µl/well) or PE-conjugated donkey anti-mouse secondary antibody for control. Protected from light, cells were incubated on ice for 30 min, washed twice with FACS buffer and analyzed using an Epics XL-MCL flow cytometer (Beckman Coulter).

FIG. 3 shows representative results of this experiment. With exception of 12B7 which shows moderate cross-reactivity with mouse AXL as well as human Mer and Sky, non of the other anti-AXL antibodies of the invention cross-reacted with these molecules. In contrast, all of the tested rat anti-AXL antibodies of the invention cross-reacted with cynomolgus monkey AXL.

Example 4

Rat Anti-AXL Antibodies of the Invention Inhibit Ligand-Induced AXL Phosphorylation In Vitro ELISA experiments were performed in order to investigate whether the rat anti-AXL antibodies of the invention are able to block ligand Gash-mediated activation of AXL. Gas6-mediated AXL activation was detected by increased receptor tyrosine phosphorylation. In brief, on day 1, $3\times10^4$ cells per well were seeded in normal growth medium in flat-bottom 96 well plates. The next day, growth medium was replaced by serum-free medium to starve cells over night for 24 h. Also over night, black Maxi-Sorp 96 well plates (Nunc) were coated with mouse anti-phospho-tyrosine antibody 4G10 at 2 µg/ml PBS and 4° C. On day 3, the 4G10 antibody solution was removed and Maxi-Sorp wells were blocked with PBS, 0.5% BSA for at lest 4 h at room temperature. In parallel, cells were pre-incubated with 10 µg/ml of the mouse control antibody 72A1 as well as the rat anti-AXL antibodies 2A1, 11D7, 11D5, 11B7, 6E7, and 10D12 for 1 h at 37° C. and then treated with or without 400 ng/ml Gas6 (R&D Systems) for 10 min at 37° C. Medium was then flicked out and cells were lysed in lysis buffer (50 mM HEPES, pH 7.5, 150 mM NaCl, 1 mM EDTA, 10% glycerine, and 1% Triton X-100) supplemented with phosphatase and protease inhibitors (10 mM $Na_4P_2O_7$, 1 mM phenylmethylsulfonyl fluoride, 1 mM orthovanadate, 1 mM NaF, and 0.5% aprotinin) for 30 min on ice. Meanwhile, blocking buffer was removed and Maxi-Sorp plates were washed 6× with wash buffer (PBS, 0.05% Tween 20), before lysates were transferred and incubated over night at 4° C. After plates were washed 6× with wash buffer on day 4, wells were incubated with biotinylated rat anti-AXL antibody 12B7 at 0.5 μg/ml PBS for 2 h at room temperature. Plates were washed 6× with wash buffer and AP-conjugated streptavidin (Chemicon #SA110) diluted 1:4,000 in PBS was added to each well and incubated for 30 min at room temperature. Afterwards, wells were washed 6× with wash buffer and AttoPhos substrate solution (Roche #11681982) was added. Using a Victor plate reader (Perkin Elmer), the fluorescence of each well was collected at an excitation wavelength of 430 nm and an emission wavelength of 580 nm.

FIG. 4 shows representative results of this experiment for NIH3T3-AXL cl.7 fibroblasts (A) and NCI-H292 lung cancer cells (B). The rat anti-AXL antibodies 11B7, 11D5, 6E7, and 10D12 of the invention were able to block or reduce ligand-mediated AXL activation as indicated by decreased phosphorylation, and are thus considered antagonistic anti-AXL antibodies. In contrast, the rat anti-AXL antibodies 2A1 and 11D7 of the invention stimulate basal AXL activation as indicated by increased phosphorylation, do not significantly reduce ligand-mediated AXL activation, and are therefore considered agonistic anti-AXL antibodies. Similar effects with the same panel of antibodies were observed in the lung cancer cell lines CaLu-1 and CaLu-6, the breast cancer cell lines Hs578T and MDA-MB-231, the prostate cancer cell line PC-3, the pancreas cancer cell line PANC-1, the melanoma cell line C-8161, the ovarian cancer cell lines SkOV-3 and SkOV-8, the glioblastoma cell line SF-126, the cervical cancer cell line CaSki, as well as the gastric cancer cell lines Hs746T and MKN-1.

Example 5

Rat Anti-AXL Antibodies of the Invention Inhibit Ligand-Induced p42/p44 MAP-Kinase Phosphorylation In Vitro Next, ELISA experiments were performed in order to investigate whether the rat anti-AXL antibodies of the invention are able to block ligand Gas6-mediated activation of p42/p44 MAP-Kinase. Gas6-mediated p42/p44 MAP-Kinase activation was detected by increased protein (Thr202/Tyr204) phosphorylation. In brief, on the first day, $2\times10^4$ cells per well were seeded in flat-bottom 96 well plates. The next day, normal growth medium was replaced by serum-free medium to starve cells for 36 h. Thereafter, cells were pre-incubated with 10 μg/ml of the isotypic control antibody 1 D5 as well as the rat anti-AXL antibodies 11D5, 11B7, and 2A1 for 1 hr at 37° C. and then treated with or without 400 ng/ml Gas6 (R&D Systems) for 10 min at 37° C. Medium was flicked out and cells were fixed with 4% formaldehyde in PBS (pH 7.5) for 30 min at room temperature. Formaldehyde solution was removed and cells were washed twice with wash buffer (PBS, 0.1% Tween 20). Cells were quenched with 1% $H_2O_2$, 0.1% $NaN_3$ in wash buffer and incubated for 20 min at room temperature. Afterwards, the quenching solution was removed, and cells were washed twice with wash buffer and blocked with PBS, 0.5% BSA for 4 h at 4° C. Anti-phospho-p42/p44 MAP Kinase (Thr202/Tyr204) primary antibody (polyclonal rabbit; Cell Signaling #9101) diluted 1:500 in PBS, 0.5% BSA, 5 mM EDTA was added over night at 4° C. On day 4, the antibody solution was removed and the plate was washed 3× with wash buffer. HRP-conjugated anti-rabbit secondary antibody (Dianova #111-036-045) diluted 1:2,500 in PBS, 0.5% BSA was then added to each well and incubated for 1.5 h at room temperature. The plate was washed 3× with wash buffer and twice with PBS for 5 min each. Tetramethylbenzidine (TMB, Calbiochem) was added and monitored at 620 nm. The reaction was stopped by addition of 100 μl of 250 nM HCl and the absorbance was read at 450 nm with a reference wavelength of 620 nm using a Vmax plate reader (Thermo Lab Systems).

FIG. 5 shows representative results of this experiment for the cervical cancer cell line CaSki. The rat anti-AXL antibodies 11B7 and 11D5 of the invention were able to reduce ligand-mediated p42/p44 MAP-Kinase activation as indicated by decreased phosphorylation, and are thus considered antagonistic anti-AXL antibodies. In contrast, the rat anti-AXL antibody 2A1 of the invention stimulates basal p42/p44 MAP-Kinase activation as indicated by increased phosphorylation, does not reduce ligand-mediated p42/p44 MAP-Kinase activation, and is therefore considered an agonistic anti-AXL antibody. Similar effects with the same panel of antibodies were observed in the breast cancer cell line Hs578T and the lung cancer cell line NCI-H292.

Example 6

Rat Anti-AXL Antibodies of the Invention Inhibit Ligand-Induced Akt Phosphorylation In Vitro Furthermore, ELISA experiments were performed in order to investigate whether the rat anti-AXL antibodies of the invention are able to block ligand Gas6-mediated activation of Akt-Kinase. Gas6-mediated Akt-Kinase activation was detected by increased protein (Ser473) phosphorylation. In brief, on day 1. $2\times10^4$ cells per well were seeded in flat-bottom 96 well plates. The next day, normal growth medium was replaced by serum-reduced (DMEM, 0.5% FCS for NIH3T3-AXL cl.7 fibroblasts) or serum-free (for cancer cell lines) medium to starve cells for 36 h. Thereafter, cells were pre-incubated with 10 μg/ml of the isotypic control antibody 1D5 as well as the rat anti-AXL antibodies 11D5, 11B7, and 2A1 for 1 h at 37° C. and then treated with or without 400 ng/ml Gas6 (R&D Systems) for 10 min at 37° C. Medium was flicked out and cells were fixed with 4% formaldehyde in PBS (pH 7.5) for 30 min at room temperature. Formaldehyde solution was removed and cells were washed twice with wash buffer (PBS, 0.1% Tween 20). Cells were quenched with 1% $H_2O_2$, 0.1% $NaN_3$ in wash buffer and incubated for 20 min at room temperature. Afterwards, the quenching solution was removed, and cells were washed twice with wash buffer and blocked with PBS, 0.5% BSA for 4 h at 4° C. Anti-phospho-Akt (Ser473) primary antibody (polyclonal rabbit; Cell Signaling #9271) diluted 1:500 in PBS, 0.5% BSA, 5 mM EDTA was added over night at 4° C. On day 4, the antibody solution was removed and the plate was washed 3× with wash buffer. HRP-conjugated anti-rabbit secondary antibody (Dianova #111-036-045) diluted 1:2,500 in PBS, 0.5% BSA was then added to each well and incubated for 1.5 h at room temperature. The plate was washed 3× with wash buffer and twice with PBS for 5 min each. Tetramethylbenzidine (TMB, Calbiochem) was added and monitored at 620 nm. The reaction was stopped by addition of 100 μl of 250 nM HCl and the absorbance was read at 450 nm with a reference wavelength of 620 nm using a Vmax plate reader (Thermo Lab Systems).

FIG. 6 shows representative results of this experiment for NIH3T3-AXL cl.7 fibroblasts (A) and CaLa-1 lung cancer cells (B). The rat anti-AXL antibodies 11B7 and 11D5 of the invention were able to block or reduce ligand-mediated Akt-Kinase activation as indicated by decreased phosphorylation, and are thus considered antagonistic anti-AXL antibodies. In contrast, the rat anti-AXL antibody 2A1 of the invention stimulates basal Akt-Kinase activation as indicated by increased phosphorylation, does not reduce ligand-mediated Akt-Kinase activation, and is therefore considered an agonistic anti-AXL antibody. Similar effects with the same panel of antibodies were observed in the lung cancer cell line NCI-H292, the breast cancer cell lines Hs578T and MDA-MB-231, the prostate cancer cell line PC-3, the pancreas cancer cell line PANC-1, the melanoma cell line C-8161, the ovarian cancer cell lines SkOV-3 and SkOV-8, the bladder cancer cell line TCC-Sup, as well as the fibrosarcoma cell line HT1080.

Example 7

Rat and Chimeric Anti-AXL Antibodies of the Invention Inhibit Ligand-Induced AKT Phosphorylation In Vitro to Similar Extent Chimeric derivatives of the rat anti-AXL antibodies 11B7 and 11D5 were generated as part of this invention (see below). In order to investigate whether the rat anti-AXL antibodies of the invention and the corresponding chimeric anti-AXL antibodies of the invention were able to block ligand Gas6-mediated activation of the Akt-Kinase in NIH3T3-AXL cl.7 fibroblasts to similar extent, ELISA experiments were performed. Antibody-mediated Akt-Kinase inhibition was detected by decreased protein (Ser473) phosphorylation. In brief, on day 1. $2\times10^4$ cells per well were seeded in flat-bottom 96 well plates. The next day, normal growth medium was replaced by serum-reduced medium (DMEM, 0.5% FCS) to starve cells for 36 h. Thereafter, cells were pre-incubated with 50 ng/ml, 100 ng/ml, 300 ng/ml, 500 ng/ml, and 1 µg/ml of rat anti-AXL antibody 11B7 or chimeric anti-AXL antibody ch11B7, as well as 50 ng/ml, 100 ng/ml, 300 ng/ml, 500 ng/ml, 1 µg/ml, 5 µg/ml, and 10 µg/ml of rat anti-AXL antibody 11D5 or chimeric anti-AXL antibody ch11D5 for 1 h at 37° C. and then treated with or without 400 ng/ml Gas6 (R&D Systems) for 10 min at 37° C. Medium was flicked out and cells were fixed with 4% formaldehyde in PBS (pH 7.5) for 30 min at room temperature. Formaldehyde solution was removed and cells were washed twice with wash buffer (PBS, 0.1% Tween 20). Cells were quenched with 1% $H_2O_2$, 0.1% $NaN_3$ in wash buffer and incubated for 20 min at room temperature. Afterwards, the quenching solution was removed, and cells were washed twice with wash buffer and blocked with PBS, 0.5% BSA for 4 h at 4° C. Anti-phospho-Akt (Ser473) primary antibody (polyclonal rabbit; Cell Signaling #9271) diluted 1:500 in PBS, 0.5% BSA, 5 mM EDTA was added over night at 4° C. On day 4, the antibody solution was removed and the plate was washed 3× with wash buffer. HRP-conjugated anti-rabbit secondary antibody (Dianova #111-036-045) diluted 1:2,500 in PBS, 0.5% BSA was then added to each well and incubated for 1.5 h at room temperature. The plate was washed 3× with wash buffer and twice with PBS for 5 min each. Tetramethylbenzidine (TMB, Calbiochem) was added and monitored at 620 nm. The reaction was stopped by addition of 100 µl of 250 nM HCl and the absorbance was read at 450 nm with a reference wavelength of 620 nm using a Vmax plate reader (Thermo Lab Systems).

FIG. 7 demonstrated that rat anti-AXL antibody 11B7 and chimeric anti-AXL antibody ch11B7 of the invention as well as rat anti-AXL antibody 11D5 and chimeric anti-AXL antibody ch11D5 of the invention were able to inhibit ligand-mediated Akt-Kinase activation to similar extent as indicated by decreased phosphorylation. Thus, as compared to their respective rat counterparts, the chimeric anti-AXL antibodies ch11B7 and ch11D5 maintained activity.

Example 8

Antagonistic Rat-Anti AXL Antibodies of the Invention Compete with Each Other for the Same or Structurally Related Epitopes and do not Share Binding Sites with Agonistic Rat-Anti AXL Antibodies of the Invention Anti-AXL antibodies of the invention were examined whether they compete with each other for similar binding epitopes on the AXL-ECD domain. Therefore binding of biotinylated anti-AXL antibodies to AXL-ECD domain-coated plates preincubated with anti-AXL antibodies was determined in a competition ELISA. In brief, 30 µg of iso-typic control antibody 1D5 as well as rat anti-AXL antibodies 11B7, 11D5, 6E7, 10D12, 11D7, and 2A1 were biotinylated with Sulfo-NHS-Biotin (Pierce #21217) according to the manufacturers' instructions and purified utilizing Micro-Bio-Spin P6 columns SSC (BIO-RAD #732-6200). On day 1, black 96 well Maxi-Sorp plates (Nunc) were coated with 100 µl/well of 1 µg/ml human AXL-ECD (R&D Systems #154-AL) in PBS over night at 4° C. On day 2, coated Maxi-Sorp plates were blocked with blocking buffer (PBS, 1% BSA, 0.05% TWEEN-20) for 2 h at room temperature (250 µl/well), and subsequently incubated with PBS or unbiotinylated isotypic control antibody 1D5 as well as unbiotinylated rat anti-AXL antibodies 11B7, 11D5, 6E7, 10D12, 11D7, or 2A1 at 10 µg/ml in blocking buffer (100 µl/well) for 1 h at room temperature. Antibody solutions were flicked out without washing and 100 µl/well PBS or biotinylated isotypic control antibody 1 D5 as well as biotinylated rat anti-AXL antibodies 11B7, 11D5, 6E7, 10D12, 11D7, or 2A1 at 0.5 µg/ml in blocking buffer were added and incubated for 15 min at room temperature. After washing 6× with wash buffer (PBS, 0.1% TWEEN-20), 80 µl/well AP-conjugated Strepta-vidin (Chemicon #SA110) diluted 1:4,000 in blocking buffer were added, incubated for 20 min at room temperature washed again 6× with wash buffer and finally washed once with PBS. For detection, 100 µl/well Attophos substrate solution (Roche #11681982) were added. Using a Victor plate reader (Perkin Elmer), the fluorescence of each well was collected at an excitation wavelength of 430 nm an emission wavelength of 580 nm.

FIG. 8 shows representative results of this analysis. The antagonistic anti-AXL antibodies 11B7, 11D5, 6E7, and 10D12 of the invention compete with each other for the same or structurally adjacent epitopes. The two agonistic antibodies 11D7 and 2A1 of the invention recognize individually different epitopes and therefore are not mutually exclusive. Moreover, 11D7 and 2A1 do not compete with the antagonistic antibodies for binding to the AXL-ECD. The control antibody 1D5 did not bind to AXL-ECD.

Example 9

Rat and Chimeric Anti-AXL Antibodies of the Invention Inhibit Lung Cancer Cell Migration and Proliferation In Vitro To examine the migration and proliferation rates of different cells and culture conditions, in vitro wound healing/ scratch assays are being employed for many years. These assays generally involve growing a confluent cell monolayer first. A small area is then disrupted and a group of cells are being destroyed or displaced by scratching a line through the layer with, for example, a pipette tip. The open gap is then inspected microscopically over time as the cells move in and fill the damaged area ("healing"). In brief, 1.5×10$^6$ NCI-H292 lung cancer cells were seeded per well of a 12 well dish and cultured in normal growth medium (RPMI, 10% FCS). After 8 h, cells were rinsed with PBS and starved in low serum medium (RPMI, 0.5% FCS) over night for 24 h. Using a sterile 200 µl pipette tip, three separate uniform wounds per well were scratched through the confluent NCI-H292 cell monolayers. Cells were gently rinsed with PBS and incubated with low serum medium (RPMI, 0.5% FCS) containing no additive, 10 µg/ml of the isotypic control antibody 1D5, the antagonistic rat anti-AXL antibodies 11D5, 11B7, 6E7, or 10D12, the chimeric anti-AXL antibodies chn11D5 IgG2 and chn11B7 IgG2, the agonistic rat anti-AXL antibodies 2A1 and 11D7 as well as 10 µg/ml of Erbitux or 5 µM Sutent for comparison. Cells were permitted to migrate into the area of clearing for 24 h, washed once with PBS and fixed with ice cold Methanol (100%) at −20° C. After cells were stained with crystal violet (0.5% in 20% Methanol), rinsed with water and dried over night, photos of the wounds were taken.

FIG. 9 shows representative results of this experiment for NCI-H292 lung cancer cells. Compared to the isotypic control antibody, the antagonistic rat anti-AXL antibodies 11D5, 11B7, 6E7, and 10D12 of the invention, as well as the chimeric anti-AXL antibodies chn11D5 IgG2 and chn11B7 IgG2 of the invention reduced the re-population of the cleared area, whereas the agonistic rat anti-AXL antibodies 2A1 and 11D7 of the invention led to a complete closure of the wound. Similar results with the same panel of antibodies were observed with the ovarian cancer cell line SkOv-3 or the gastric cancer cell line MKN-1.

Example 10

Rat Anti-AXL Antibodies of the Invention Inhibit Ligand-Induced Migration of NIH3T3-AXL cl.7 Fibroblasts In Vitro Transmigration experiments were performed in order to investigate whether the antibodies of the invention block cell migration. For this purpose, in the morning of day 1, NIH3T3-AXL cl.7 cells were seeded on 15 cm dished in normal growth medium, which in the evening was replaced by serum-reduced medium (DMEM, 0.5% FCS) in order to starve cells for 36 h. The next day, a FluoroBlock 96 well plate (Becton Dickinson #351164, 8 µm pore size) was coated with 10 µg collagen 1/ml 0.1 M acetic acid over night at 37° C. On day 3, the serum-reduced medium (DMEM, 0.5% FCS) was replaced by serum-free medium (DMEM, 0% FCS, 0.1% BSA) for another 4 h. Cells were harvested with 10 mM EDTA in PBS and pre-incubated with rat anti-AXL antibodies 4A6, 11B7 or 2A1 at a cell density of 4×10$^5$ cells/ml and an antibody concentration of 10 µg/ml for 45 min. 50 µl cell suspension (20,000 cells) per well were then placed in the top chamber of the FluoroBlock 96-well plate, 225 µl medium (DMEM, 0% FCS, 0.1% BSA) with or without 400 ng/ml mouse Gas6 (R&D Systems) were used per well in the bottom chamber. Cells were left to migrate for 7 h at 37° C. and stained afterwards with 4.2 µM calcein-AM (Molecular Probes #C3099) in PBS, 1 mM CaCl$_2$, 1 mM MgCl$_2$ for 1 h at 37° C. Using a Victor plate reader (Perkin Elmer), the fluorescence of each well was measured at a wavelength of 530 nm.

FIG. 10 shows that the antagonistic anti-AXL antibody 11B7 of the invention reduced both basal and Gas6-induced migration of NIH3T3-AXL cl. 7 fibroblasts, whereas the agonistic rat anti-AXL antibody 2A1 of the invention increased ligand-induced and, in particular, basal migration of NIH3T3-AXL cl.7 cells. The antibody 4A6 did not affect cell migration.

Example 11

Rat Anti-AXL Antibodies of the Invention Inhibit Ligand-Induced Proliferation of NIH3T3-AXL cl.7 Fibroblasts In Vitro In vitro experiments were conducted in order to determine the ability of the rat anti-AXL antibodies of the invention to inhibit Gas6-induced cell proliferation. For this purpose, 2,500 NIH3T3-AXL cl.7 fibroblasts per well were seeded in FCS-containing medium on 96 well plates over night. The next day, cells were starved in serum-reduced medium (DMEM, 0.5% FCS) for 10 h and subsequently pre-incubated with 20 µg/ml of the mouse control antibody 72A1, the antagonistic rat anti-AXL antibodies 11D5 and 11B7, as well as the agonistic antibody 2A1 in DMEM, 0.5% FCS for 1 h at 37° C. Cells were treated with or without 400 ng/ml mouse Gas6 (R&D Systems) by adding ligand directly to the antibody solution, and were then left to grow for 96 h. Alamar-Blue™ (BIOSOURCE #DAL1100) was added and incubated at 37° C. in the dark. Absorbance was measured at 590 nm every 30 min. The data were taken 4 h after addition of AlamarBlue™.

FIG. 11 shows representative results of this experiment. The antagonistic anti-AXL antibodies 11D5 and 11B7 of the invention blocked Gas6-induced proliferation of NIH3T3-AXL cl.7 fibroblasts, whereas the agonistic rat anti-AXL antibody 2A1 of the invention increased ligand-induced and, in particular, basal proliferation of NIH3T3-AXL cl.7 cells.

Example 12

Rat Anti-AXL Antibodies of the Invention Inhibit Ligand-Mediated Anti-Apoptosis of Serum-Starved NIH3T3-AXL cl.7 Fibroblasts In Vitro Induction of apoptosis and activation of caspases can result from a variety of stimuli including growth factor withdrawal, exposure to chemotherapeutic agents or radiation, or initiation of the Fas/Apo-1 receptor-mediated cell death process. Gas6-AXL interaction has been shown to be implicated in the protection of a range of cell types from apoptosis, including serum-starved NIH3T3 fibroblasts (Goruppi et al., 1996, Oncogene 12, 471-480) or pulmonary endothelial cells (Healy et al., 2001, Am. J. Physiol., 280, 1273-1281). In the present example we examined whether rat anti-AXL antibodies of the invention interfere with Gas6-mediated anti-apoptosis of serum-starved NIH3T3-AXL cl.7 fibroblasts, and thus induce apoptosis. Apoptosis rates were thereby determined by measurement of the cellular caspase-3/7 activity. For this purpose, NIH3T3-AXL cl.7 cells were seeded at a density of 1.5×10$^3$ cells per well in black clear-bottom 96 well plates (100 µl/well). The day after, normal growth medium was replaced by serum-reduced medium (DMEM, 0.5% FCS) to starve cells over night for 24 h. The next day, antibody solutions of the isotypic control antibody 1D5, the antagonistic rat anti-AXL antibodies 11B7 and 11D5, as well as the agonistic rat anti-AXL antibodies 11D7 and 2A1 at 80 µg/ml in DMEM, 0% FCS, 0.01% BSA were prepared. The cells were washed with PBS, covered with 60 µl of DMEM, 0% FCS, 0.01% BSA, and 10 µl of the respective antibody solution were added. After 1 h incubation at 37° C., 10 µl of DMEM, 0% FCS, 0.01% BSA with or without 3.2 µg/ml mouse Gas6 (R&D Systems) were added (the final concentrations of antibody and Gas6 were 10 µg/ml and 400 ng/ml, respectively), and cells were incubated at 37° C. for another 5 h. The following steps refer to the technical bulletin to the Apo-ONE Homogenous Caspase-3/7 Assay (Promega, G7791). In brief, culture plates were removed from the incubator and allowed to equilibrate at room temperature for 20 min. 60 µl of Apo-ONE substrate and 6 ml buffer were thawed, combined, and added to the samples (75 µl/well). The contents of wells was gently shaken for 30 sec, and, protected from light, incubated at room temperature for 1 h. Using a Victor plate reader (Perkin Elmer), the fluorescence of each well was measured at an excitation wavelength of 485 nm and an emission wavelength of 530 nm.

FIG. 12 shows representative results of this experiment. Compared to the isotypic control antibody, the antagonistic rat anti-AXL antibodies 11B7 and 11D5 of the invention reduced Gas6-mediated anti-apoptosis of serum-starved NIH3T3-AXL cl.7 fibroblasts, and thus induced apoptosis. In contrast, the agonistic rat anti-AXL antibodies 2A1 and 11D7 of the invention strongly induced anti-apoptosis of serum-starved NIH3T3-AXL cl.7 cells regardless of the absence or presence of Gas6, and therefore inhibited apoptosis.

Example 13

Rat Anti-AXL Antibodies of the Invention Inhibit Spheroid-Based Cellular Angiogenesis In Vitro AXL is a key regulator of multiple angiogenic behaviors including endothelial cell migration, proliferation, and tube formation in vitro (Holland et al., Cancer Res: 65, 9294-9303, 2005). Therefore, the rat anti-AXL monoclonal antibodies 11B7 and 11D5 of the invention were tested for inhibitory effects on VEGF-A-induced vessel sprouting of HUVEC-spheroids. The experiments were pursued in modification of the originally published protocol (Korff and Augustin: J Cell Sci 112: 3249-58, 1999). In brief, spheroids were prepared as described (Korff and Augustin: J Cell Biol 143: 1341-52, 1998) by pipetting 500 human umbilical vein endothelial cells (HUVEC) in a hanging drop on plastic dishes to allow over night spheroid aggregation. 50 HUVEC spheroids were then seeded in 0.9 ml of a collagen solution (2 mg/ml) and pipetted into individual wells of a 24 well plate to allow polymerization. Decreasing concentrations of the rat anti-AXL antibodies 11B7 and 11D5 ($1\times10^6$ M, $1\times10^{-7}$ M, $1\times10^{-8}$ M, $1\times10^{-9}$ M, $1\times10^{-10}$ M) were directly mixed in the collagen solution before polymerization, whereas the growth factor VEGF-A (final concentration 25 ng/ml) was added after 30 min by pipetting 100 µl of a 10-fold concentrated working dilution on top of the polymerized gel. Plates were incubated at 37° C. for 24 hours and fixed by adding 4% paraformaldehyde. Sprouting intensity of HUVEC spheroids was quantified by an image analysis system that determines the cumulative sprout length per spheroid using an inverted microscope and the digital imaging software Analysis 3.2 (Soft imaging system, Munster, Germany). The mean of the cumulative sprout length of 10 randomly selected spheroids was analyzed as an individual data point.

FIG. 13 shows the results of this experiment. The antagonistic rat anti-AXL antibodies 11B7 (A) and 11D5 (B) of the invention inhibited VEGF-A-stimulated HUVEC sprouting in the spheroid-based angiogenesis assay in a dose-dependent manner. Whereas treatment with the highest concentration of 11B7 reduced HUVEC sprouting to basal levels, inhibition with the highest concentration of 11D5 was not as effective (left panel). HUVEC sprouting was inhibited with $IC_{50}$ values of $9.8\times10^{-8}$ M and $7.0\times10^{-7}$ M for 11B7 and 11D5, respectively (right panel).

Example 14

Rat Anti-AXL Antibodies of the Invention Reduce Human Prostate Carcinoma Growth in Nude Mice The anti-tumor efficacy of therapeutic antibodies is often evaluated in human xenograft tumor studies. In these model systems, human tumors grow as xenografts in immunocompromised mice and therapeutic efficacy is measured by the degree of tumor growth inhibition. The aim of this study was to evaluate whether the antagonistic rat anti-AXL antibody 11B7 of the invention interferes with tumor growth of human prostate cancer cells in nude mice. In brief, on day 0, 7-8 weeks old male $NMRI^{-nu/nu}$ mice (approximate weight: 30 g after acclimatization) were anesthesized with 1.5-2.0 volume percent isoflurane at an oxygen flow rate of 2 l/min, and $1\times10^6$ PC-3-LN cells in 25 µl PBS were orthotopically implanted into the prostate. PC-3-LN cells are derived from the PC-3 prostate carcinoma cell line which was infected with a retrovirus coding for a luciferase-neomycin fusion protein. The onset of tumor growth and tumor growth progression was therefore measurable via in vivo bioluminescence imaging. For this purpose, luciferin was injected intraperitoneally (i.p.) into the mice and light emission was measured 10 min post injection using a NightOWL LB 981 bioluminescence imaging system (Berthold Technologies, Germany). Prior to first treatment, mice were randomized and statistical tests performed to assure uniformity in starting tumor volumes (mean, median and standard deviation) across the treatment groups of 10 animals each. On day 8, all treatments started and were continued until day 34, followed by necropsy on day 35. 25 mg/kg of the isotypic control antibody 1D5 and the antagonistic rat anti-AXL antibody 11B7 were intraperitoneally (i.p.) administered 3× a week (Mo, Wed, Fr) into animals of group 1 and 2, respectively. Animals of group 3 orally (p.o.) received 40 mg/kg of Sutent once a day. Animals of Group 4 received three intraveneous (i.v.) injections with 12.5 mg/kg of Taxotere 4 days apart of each other. An overview of the treatment groups is given below.

| Group | Treatment | Route | Application Scheme | Animal Number |
|---|---|---|---|---|
| 1 | 1D5 | i.p. | 3 times per week (Mo, Wed, Fr) starting one day after randomization[2)] | 10 |

-continued

| Group | Treatment | Route | Application Scheme | Animal Number |
|---|---|---|---|---|
| 2 | 11B7 | i.p. | 25 mg/kg | 3 times per week (Mo, Wed, Fr) starting one day after randomization[2)] | 10 |
| 5 | Sutent | 40 mg/kg | p.o. | daily starting one day after randomization[2)] | 10 |
| 6 | Taxotere | 12.5 mg/kg | i.v. | 3 doses 4 days apart starting one day after randomization | 10 |

<br/>

FIG. 14 shows the results of this experiment. Compared to the isotypic control antibody 1D5, the antagonistic rat anti-AXL antibody 11B7 of the invention reduced the overall growth of PC-3-LN prostate tumors in nude mice.

Example 15

Rat Anti-AXL Antibodies of the Invention Inhibit Metastasis of Human Prostate Carcinoma In the same experiment as described under "Rat anti-AXL antibodies of the invention reduce human prostate carcinoma growth in nude mice", relocalization of PC-3-LN tumor cells into other organs (metastasis) was analyzed post necropsy to evaluate anti-metastatic effects of the antagonistic rat anti-AXL antibody 11B7 of the invention. For this purpose, selected organs (liver, spleen, lungs, femur, part of the lumbar spine) were collected post necropsy, homogenized, and supplemented with luciferin. Subsequently, light emission was measured using a NightOWL LB 981 bioluminescence imaging system (Berthold Technologies, Germany).

FIG. 15 shows the results of this experiment for the analysis of spleens. Compared to the isotypic control antibody 1D5, the antagonistic rat anti-AXL antibody 11B7 of the invention reduced the occurrence of spleen metastases. Noteworthy, the anti-metastatic effect of 11B7 in this experiment was stronger than that of Sutent. Similar observations were obtained for liver, lung, femur, and lumbar spine metastasis.

Example 16

AXL is Predominantly Expressed in Tumor Rather than Adjacent Normal Tissue

In this study, the AXL expression in 17 different human malignancies was immunohistochemically analysed on formalin-fixed paraffin-embedded tissues in tissue multiarray format. For each tumor type, pairs of tumor tissue and matching non-malignant tissue were examined. In brief, tissue was fixed for 16 to 20 h in 4% neutral buffered formalin and embedded in paraffin. For construction of a 60-core tissue microarray (TMA), one punch of healthy tissue and one punch of corresponding tumor tissue of each case was chosen by a pathologist. A 96-core TMA with normal control tissue punches (three of each tissue type) was generated regarding to FDA guidelines. Each punch was 1.5 mm in diameter.

With a microtome, 2-4 μm sections of selected tissue blocks were cut, mounted on silanized glass slides (Sigma) and dried at 60° C. for 30 min and 38° C. over night. Sections were deparaffinized by incubation in a xylene bath for 5 min twice, in acetone for 5 min twice and finally in distilled water for 5 min. Heat pre-treatment of the sections was performed in 10 mM citrate buffer, pH 6.0 in a steamer for 30 min, followed by washing in distilled water. Endogenous peroxidase was blocked by incubation with a freshly prepared solution of 0.3% $H_2O_2$ in methanol for 20 min at room temperature, followed by washing with distilled water and PBS for 5 min each. Sections were incubated with polyclonal goat anti-human AXL antibody (Santa Cruz SC-1096) for 60 min (1:20 dilution in TBST) at room temperature. After three washes in TBST, the sections were incubated with biotinylated rabbit anti-goat secondary antibody (Dianova, 1:200 dilution in TBST) for 45 min at room temperature. After washing as before, the sections were incubated with Streptavidin/HRP (DAKO, 1:300 dilution in TBST) for 30 min at room temperature, followed by washing as before. Staining was achieved with DAB solution (DAKO; 1:50 dilution in substrate buffer) for 10 min at room temperature. Finally, the slides were rinsed with water, counterstained with Harris' hematoxylin, and covered with a glass slide. Control sections were incubated with goat IgG control antibody (R&D) instead of anti-AXL primary antibody.

FIG. 16 summarizes the results of this analysis on AXL expression in 17 different human solid tumors and corresponding non-malignant tissue (A). Among all cases screened for each indication, no marked expression was detected in follicular lymphoma, prostate cancer (except for single cells), and in kidney cancer. Melanoma and Merkel cell tumors showed very low expression of AXL. A weak expression was observed in a few tumors of the lung, mainly adenocarcinomas. Esophagus and Barrett tumors, ovarian, colon and pancreatic tumors as well as liver tumors (hepatocellular carcinoma) showed weak staining in about 30% of the cases. Head and neck tumors showed weak to moderate staining in about 40% of the tumors. Weak to moderate staining was detected in 60% to 100% of the analyzed tumors of the breast, cervix, bladder, thyroid and the stomach. Most intense staining was seen in mammary tumors and in a signet ring cell carcinoma of the stomach (B). Non-malignant tissues mainly showed no specific staining except from tubuli of the kidney which sometimes showed weak staining over background.

Example 17

Structure and Characteristics of Anti-AXL Antibodies

17 A. Nucleotide Sequences of Rat Antibody Variable Domains

Rat anti-AXL antibody variable domains were cloned from hybridoma cells. RNA was prepared utilizing the RNA-Extraction kit RNeasy (RNeasy midi-kit, Qiagen). cDNA encoding for the antibody genes was prepared using the 5 RACE kit (Invitrogen) according to manufacturer's instructions.

Briefly, first strand cDNA was synthesized from total or RNA using the gene-specific GSP1-primers and SuperScript™ II Reverse Transcriptase. After first strand cDNA synthesis, the original mRNA template is removed by treatment with the RNase Mix. A homopolymeric tail is then added to the 3'-end of the cDNA. PCR amplification is accomplished using Taq DNA polymerase, a nested, gene-specific primer (GSP2) that anneals to a site located within the cDNA molecule and an anchor primer provided with the kit. Following amplification 5' RACE products were cloned into the pLXSN-ESK vector for sequencing. To facilitate cloning the Anchor Primer (AP) included a recognition sequence for Sal I, GSP2 primers contained a XhoI site.

GSP1 Primer:

```
                                          (SEQ ID NO: 51)
    kappa_GSP1:      GATGGATGCATTGGTGCAGC (SEQ ID NO: 52)
    new_kappa_GSP1: ATAGATACAGTTGGTGCAGC (SEQ ID NO: 53)
    heavy_GSP1:      CAGGGTCACCATGGAGTTA
```

GSP2 Primer:

```
                                          (SEQ ID NO: 55)
    XhoI-hGSP2:  CCGCTCGAGCGGGCCAGTGGATAGACAGATGG (SEQ ID NO: 54)
    XhoI-kGSP2:  CCGCTCGAGCGGCCGTTTCAGCTCCAGCTTGG
```

Utilization of GSP Primers for Rat Anti-AXL Mab Cloning:
  11B7: kappa GSP1; XhoI-kGSP2
    heavy GSP1; XhoI-hGSP2
  10D12: kappa_GSP1, new_kappa_GSP1; XhoI-kGSP2
    heavy GSP1; XhoI-hGSP2
  11D5: new_kappa_GSP1; XhoI-kGSP2
    heavy GSP1; XhoI-hGSP2

17 B. Aminoacid Sequence Rat Anti-AXL Antibody Variable Domains

Rat antibody variable domain sequences were translated from sequenced genes cloned into the pLXSN-ESK vectors. The given amino acid sequences start at position one of the variable domain. The complementarity determining regions (CDRs) required for the specific binding of the antibody to its target are defined according to Kabat (Kabat et al. Sequences of Proteins of Immunological Interest, Fifth Edition. NIH Publication No. 91-3242, 1991). The Kabat definition is based on the sequence variability within the variable domains. Anti-AXL specific CDR regions of the antibodies are listed in SEQ ID NO: 13-30. The individual CDRs include the following positions:
CDR-L1: 24-34
CDR-L2: 50-56
CDR-L3: 89-97
CDR-H1: 31-35b
CDR-H2: 50-65
CDR-H3: 95-102

17 C Rat Antibody Expression and Purification:

Hybridomas were cultured in Celline CL 1000 bioreactors (Integra Biosciences) at 37° C., 5-7% $CO_2$ using DMEM including 4.5 g/L glucose; 1% Glutamine, 1% Pyruvate 1% Pen/Strep. FCS supplementation is 1% FCS for the nutrient compartment and 5% low IgG FCS for the cell compartment. Harvest and media exchange is performed twice a week. Cell splitting 1/1→→1/3 depending on cell growth. Productivity is tested once a week via SDS-PAGE analysis. Supernatants are stored at −20° C. until purification. Mycoplasma test of running cultures is done once a week.

Antibodies are purified using Protein A or G Sepharose FF (GE-Healthcare) via an Äkta Explorer 100 System (GE-Healthcare). Columns are individually packed for each purification. The column size is adjusted to the expected productivity and size of each batch (usually 50-500 mg). Protein containing solutions are kept on ice or at 4° C. wherever possible. Sterile buffers and double distilled water are used for the entire process.

Supernatants are thawed, buffered with 50 mM TRIS pH 8.5, centrifuged, filtered through a 0.22 µm membrane and loaded onto the column. After washing with 8 column volumes (CV) 50 mM $PO_4$, pH8.5 the antibody is eluted within 10 CV 100 mM Glycin, pH 3.3. Eluate fractions are rebuffered immediately to neutral pH by adding 1/5 µM Tris pH 8.0 (1 ml Tris per 4 ml eluate fraction) and analysed by rSDS-PAGE subsequently. Fractions containing pure antibody are pooled, dialysed against PBS at 4° C. and sterile filtered.

Buffer system requirements are adjusted according to the individual properties of each antibody. In particular, rat IgG2a antibody 11D5 was bound to ProteinG 4 FF matrix (GE-Healthcare) and washed under high salt conditions (2M NaCl). Rat antibody IgG1 11B7 was purified via rProteinA (GE-Healthcare) under high salt conditions according to 11D5. Antibody elution was performed at pH 5.5. Flow rate for rat antibody purification has to be kept low for increased binding efficiency.

As a second purification step either ion exchange chromatography (under individual, suitable conditions) or preparative size exclusion chromatography (PBS, pH 7.4) can be implemented.

The standard protocol for quality control of the purified antibodies includes:
  rSDS-PAGE gel analysis; Coommassie or silver stained
  BCA test (Pierce #23227 BCA Protein Assay Kit; rat IgG standard #31233)
  Analytical size exclusion (Superdex 200 Tricorn 10/300 GL, ~250 mg in 250 µl; 0.5 ml/min, Äkta Explorer 100)
  Endotoxin test (LAL, Cambrex QCL-1000® Chromogenic LAL Endpoint Assay #US50-648U)
  Cell based activity assays (FACS binding; pAkt; pAXL)

Purified antibodies are stored in PBS, pH 7.4 under sterile conditions at 4° C. or −20° C. depending on their stability.

17D. Antibody Affinity Determination by FACS Scatchard

Human AXL overexpression NIH3T3 cells were harvested by incubation with 10 mM EDTA in PBS and resuspended at 6 million cells per ml in FACS buffer (PBS pH 7.4, 3% FCS, 0.1% $NaN_3$). In a round-bottom microtiter plate, 100 µl of cell suspension were added to 100 µl of antibody solution containing antibodies 11B7, 11D5, ch11B7-IgG2 or ch11D5-IgG2 at concentrations between 40 and 0.002 µg/ml (266 and 0.01 nM) in FACS buffer. Antibody binding was allowed to proceed for 2 hours on ice. Then, cells were washed twice with 250 µl FACS buffer per well, and resuspended in 200 µl of secondary antibody (anti-rat-PE; Jackson) diluted 1:50 in FACS buffer. After 45 minutes of incubation, cells were again washed twice in FACS buffer and resuspended in 500 ml PBS for FACS analysis. Analysis was carried out on a Beckman-Coulter FACS FC500. To determine the apparent affinity constant $K_{Dapp}$, mean fluorescence values were plotted against the ratio of mean fluorescence and the corresponding antibody concentration ([M]). The calculated $K_{Dapp}$ resulted from the inverse slope of the straight line are listed below:

| Clone | $K_D$ value (nM) |
|---|---|
| 11B7 | 0.38 |
| ch11B7-IgG2 | 0.6 |
| 11D5 | 0.81 |
| Ch11D5-IgG2 | 0.9 |

18

Chimerization of Rat Anti-AXL Antibodies

Human kappa light chain and heavy chain IgG1/2 genes were cloned from peripheral blood mononuclear cells (PBMC) of a human volunteer as described below:

PBMCs were prepared from whole blood. Blood was diluted 1/2.5 in PBS/2 mM EDTA with 10 U/ml heparin at RT, layered over 15 ml Biocoll solution covered by a diaphragm (35 ml/tube) [Biocoll from Biochrom #L6115]. Samples were centrifuged at RT for 30 min at 400×g and serum (~15 ml) was discarded. Interface containing PBMCs was carefully recovered using a Pasteur pipette. PBMCs were washed 2× in PBS/2 mM EDTA (first wash 100 ml, second wash 50 ml) and spun down at 300×g for 10 min. Cell pellet was resuspended in RPMI/10% FCS (25 ml) and yielded $5.5 \times 10^7$ PBMCs.

RNA was prepared from PBMCs using RNeasy kit from Qiagen (#75142) according to manufacturer's instructions. Purified RNA (30 µg) was stored in aliquots at −80° C.

cDNA for antibody IgG gamma 1 and 2 as well as kappa chains were prepared from isolated RNA by RT-PCR using Superskript III Reverse Transkriptase (invitrogen #18080-93) according to manufacturers instructions using the following primers:

```
1) RT-gamma:
                                      (SEQ ID NO: 56)
GCG TGT AGT GGT TGT GCA GAG 2) RT-gamma2:
                                      (SEQ ID NO: 57)
GGG CTT GCC GGC CGT G 3) RT-kappa:
                                      (SEQ ID NO: 58)
TGG AAC TGA GGA GCA GGT GG 4) 5'Blp:
                                      (SEQ ID NO: 59)
AGA TAA GCT TTG CTC AGC GTC CAC CAA GGG CCC ATC
GGT 5) 3'Bam(GAG):
                                      (SEQ ID NO: 60)
AGA TGG ATC CTC ATT TAC CCG GAG ACA GGG AGA G 6) 5'Bsi:
                                      (SEQ ID NO: 61)
AGA TAA GCT TCG TAC GGT GGC TGC ACC ATC TGT CTT
CAT 7) 3'Bam(CTT):
                                      (SEQ ID NO: 62)
AGA TGG ATC CCT AAC ACT CTC CCC TGT TGA AGC TCT
```

Primers were dissolved at 100 µM. RT-PCR reactions were performed using 2 µmol oligo RTγ and RTκ respectively, adding 1 µg RNA, 10 mM dNTP mix and heat for 5 min to 65° C. 4 µl first strand buffer, 1 µl 0.1M DTT, 1 µl RNase inhibitor (40 U/µl Fermentas #EO0311) and 2 µl Superskript III RT were added, mixed and incubated at 50° C. for 1 h followed by a heat inactivation step for 15 min at 70° C.

2 µl of first strand reaction were used for second step PCR using Taq polymerase (Eurochrom #EME010001) to yield double stranded DNA of antibody constant domains. The primer 5'Blp and 3'Bam(GAG) were used to amplify γ-chain, and 5'Bsi and 3'Bam(CTT) were used to amplify κ-chain constant regions using the following PCR settings:

κ-chain amplification:

| 94° C. | 120 sec |
|---|---|
| 94° C. | 30 sec |
| 55° C. | 30 sec |
| 72° C. | 45 sec cycle 35 times |
| 72° C. | 10 min |

γ-chain amplification:

| 94° C. | 120 sec |
|---|---|
| 94° C. | 30 sec |
| 45° C. | 30 sec |
| 72° C. | 60 sec cycle 5 times |
| 94° C. | 30 sec |
| 50° C. | 30 sec |
| 72° C. | 60 sec cycle 35 times |
| 72° C. | 10 min |

The PCR products were analysed on a TAE buffered 2% agarose gel. A single band of ~350 bp for kappa light chain and a single band of ~1000 bp for the heavy chains γ1 and γ2 were found. The PCR products were purified by Qiagen gel extraction kit, (QIAGEN, #28784) according to the manufacturer's instructions. To clone the PCR fragments into the multiple cloning site of the pcDNA3 vector (Invitrogen), pcDNA3 vector and PCR fragments were digested with HindIII (5') and BamHI (3') restriction endonucleases. Restriction sites were encoded within the PCR primers. Digested fragments were purified using the Qiagen PCR purification kit (QIAGEN, 28104), and DNA encoding the γ1, γ2 and κ chains were ligated into the pcDNA3 vector facilitating T4 DNA ligase at 16° C. overnight. Ligase was inactivated for 10 min. at 65° C. Ligated DNA plasmids were directly transformed into $CaCl_2$ competent E. coli using standard protocol and plated onto Ampicillin containing LB-plates. After incubation at 37° C. overnight single colonies were picked, suspended in 10 µl $H_2O$ and proofed for containing the respective antibody chain carrying plasmid by PCR (5 µl suspended cells, Taq polymerase, primer 5Blp and 3Bam(GAG) γ1/γ2 and 5Bsi and 3Bam(CTT) for κ colonies:

| 94° C. | 120 sec |
|---|---|
| 94° C. | 30 sec |
| 55° C. | 30 sec |
| 72° C. | 60 sec cycle 35 times |
| 72° C. | 10 min |

Samples were analysed on 1.5% agarose gel for PCR products. Antibody gene containing colonies were selected to inoculate 5 ml LB/Ampicillin medium. After incubation at 37° C. overnight E. coli were harvested and DNA was prepared using Qiagen miniprep kit (QIAGEN, #12123). A control digest (HindIII, BamHI) showed all κ and γ chain gene inserts at the expected size; sequences were verified by DNA sequencing at Medigenomix.

Rat variable domains were amplified by PCR from pLXSN-ESK vector and cloned into g1/g2 and k pcDNA3 vectors to yield the chimeric full length antibodies. Variable VL domains were amplified with the following primers, containing a HindIII and BsmI site at the 5'end and a BsiWI site at the 3'end:

VL-11B7-5':
(SEQ ID NO: 63)
AGA TAA GCT TGT GCA TTC CGA CAT CCA GAT GAC CCA

GGC TCC

VL-11B7-3':
(SEQ ID NO: 64)
AGA TCG TAC GTT TCA GCT CCA GCT TGG TGC CTC

VL-11D5-5':
(SEQ ID NO: 65)
AGA TAA GCT TGT GCA TTC CGA CAT CCA GAT GAC CCA

GTC TCC ATC

VL-11D5-3':
(SEQ ID NO: 66)
AGA TCG TAC GTT TCA GCT TGG TCC CAG

Variable VH domains were amplified with the following primers, containing a HindIII and BsmI site at the 5'end and a BlpI site at the 3'end:

VH-11 B7/11 D5-5':
(SEQ ID NO: 67)
AGA TAA GCT TGT GCA TTC CGA GGT GCA GCT TCA GGA

GTC AGG

VH-11 B7/11 D5-3':
(SEQ ID NO: 68)
AGA TGC TGA GCT GAC AGT GAC CAT GAC TCC TTG GCC

BsiWI for the light chain and the BlpI for the heavy chain are single sites at the 5' end of the constant regions to enable the direct fusion with the 3' end of the variable domain genes.

Fused to the leader sequence SEQ ID No: 69 derived from pLNOH2 vector (Norderhaug et. al. J. Immunol. Methods 204, 1997; Neuberger EMBO J. 1983; 2 (8): 1373-8, 1983) genes encoding the chimeric antibody chains were cloned into pCEP vector system for recombinant expression. Light chain genes were cloned NheI (5') and XhoI (3') into pCEP4 (Invitrogen) heavy chain genes KpnI (5') and XhoI (3') into pCEP-Pu (Kohfeld FEBS Vol 414; (3) 557ff, 1997).

HEK 293 cells seeded on 20×20 cm plates were co-transfected with 1 μg/ml of each plasmid coding for light and heavy chain genes using standard $CaPO_4$ transfection method for transient expression. Culture conditions were 37° C., 5% $CO_2$ in DMEM/F12 high glucose medium containing 5% low IgG FCS, 1% pyrovate, 1% glutamine, 1% penicillin/streptomycin. 24 h after transfection medium was exchanged by fresh medium. Supernatants were collected every 2-3 days for approximately 3 weeks. Chimeric antibodies were purified from approximately 600 ml supernatant utilizing 1 ml Hitrap rProtein A columns (GE-Healthcare) under standard buffer conditions (loading: 50 mM Tris; pH=8.5, wash: 50 mM $PO_4$; pH=8.5, elution: 100 mM Glycin; pH 3.3) as described for rat antibody purification.

Example 19

Humanization of Rat Anti-AXL Antibody Variable Domains

The rat variable regions of the chimeric antibodies were compared to human antibody germline sequences at the protein level via a BLAST search for immunoglobulin domains The closest human counterpart within the V-genes, which in addition had identical CDR loop lengths was identified. The associated D and J segments were selected from the V-BASE database (http://vbase.mrc-cpe.cam.ac.uk/) according to their homology to the rat sequences in an analogous approach.

For the rat variable domains of the 11B7 and 11D5 antibodies the following bestfitting human germline sequences (V, D and J segments) were found and defined as human framework:
VL11B7hum: Vκ1–O12+Jk1
VH11B7hum: VH4–59+D4–4 (reading frame 3)+JH4
VL11D5hum: Vκ1–L1+JK4
VH11D5hum: VH4–59+D4–4 (reading frame 3)+JH4

Leader sequences for humanized variable domains were adopted from the associated germline V-gene sequences as selected. CDR residues of rat anti-AXL antibodies defined according to Kabat (Kabat et al., Sequences of Proteins of Immunological Interest, Fifth Edition. NIH Publication No. 91-3242, 1991) were grafted into human germline frameworks for anti-AXL specificity to obtain the final humanized version of anti-AXL antibodies hum11B7 and hum11D5.

The protein sequences of the humanized anti-AXL antibodies hum11B7 and hum11D5 are as follows:

Protein sequences were back translated into DNA sequences. DNA sequences were CODON optimized for recombinant expression in mammalian cells using the Kazusa-Codon-Usage Database. The resulting DNA sequences for the humanized anti-AXL antibodies are as follows:

The optimized DNA sequences encoding for the humanized anti-AXL antibodies were synthesized by a PCR-method based on overlapping oligonucleotides.

VL-genes were cloned into pCEP4 vector utilizing the plasmid of the chimeric antibody construct pCEP4_ch11B7k1. Cloning sites are NheI (5') and BsiWI (3') which were already included in the synthesized genes of the humanized antibodies. VH genes were cloned into the corresponding chimeric heavy chain vector pCEP-PU_ch11B7g1 utilizing KpnI (5') and BlpI (3') as restriction sites. DNA optimization, gene synthesis, cloning and sequence verification was conducted at Eurofins Medigenomix GmbH, Martinsried, Germany.

Example 20

Rat and Chimeric Anti-Axl Antibodies of the Invention Inhibit Ligand-Induced Axl Phosphorylation In Vitro to Similar Extent Chimeric derivatives of the rat anti-Axl antibodies 11B7 and 11D5 were generated as part of this invention (see below). In order to investigate whether the rat anti-Axl antibodies of the invention and the corresponding chimeric anti-Axl antibodies of the invention were able to inhibit ligand Gas6-mediated Axl activation in vitro to similar extent, ELISA experiments on CaSki cervical cancer cells were performed. Gas6-mediated Axl activation was thereby detected by increased receptor tyrosine phosphorylation. In brief, on day 1, $3 \times 10^4$ cells per well were seeded in normal growth medium in flat-bottom 96 well plates. The next day, growth medium was replaced by serum-free medium to starve cells over night for 24 h. Also over night, black Maxi-Sorp 96 well plates (Nunc) were coated with mouse anti-phospho-tyrosine antibody 4G10 at 2 μg/ml PBS and 4° C. On day 3, the 4G10 antibody solution was removed and Maxi-Sorp wells were blocked with PBS, 0.5% BSA for at lest 4 h at room temperature. In parallel, cells were pre-incubated with 50 ng/ml, 100 ng/ml, 300 ng/ml, 750 ng/ml, 1 µg/ml, and 10 µg/ml of rat anti-Axl antibody 11B7 or chimeric anti-Axl antibody ch11B7 for 1 h at 37° C. and subsequently treated with or without 400 ng/ml Gas6 (R&D Systems) for 10 min at 37° C. Medium was then flicked out and cells were lysed in lysis buffer (50 mM HEPES, pH 7.5, 150 mM NaCl, 1 mM EDTA, 10% glycerine, and 1% Triton X-100) supplemented with phosphatase and protease inhibitors (10 mM $Na_4P_2O_7$, 1 mM phenylmethylsulfonyl fluoride, 1 mM orthovanadate, 1 mM NaF, and 0.5% aprotinin) for 30 min on ice. Meanwhile, blocking buffer was removed and Maxi-Sorp plates were washed 6× with wash buffer (PBS, 0.05% Tween 20), before lysates were transferred and incubated over night at 4° C. After plates were washed 6× with wash buffer on day 4, wells were incubated with biotinylated rat anti-Axl antibody 12B7 at 0.5 µg/ml PBS for 2 h at room temperature. Plates were washed 6× with wash buffer and AP-conjugated streptavidin (Chemicon #SA110) diluted 1:4,000 in PBS was added to each well and incubated for 30 min at room temperature. Afterwards, wells were washed 6× with wash buffer and AttoPhos substrate solution (Roche #11681982) was added. Using a Victor plate reader (Perkin Elmer), the fluorescence of each well was collected at an excitation wavelength of 430 nm and an emission wavelength of 580 nm.

FIG. 17 shows representative results of this experiment for the cervical cancer cell line CaSki. As demonstrated by concentration-dependent decrease of the relative Axl phosphorylation, the rat anti-Axl antibody 11B7 (A) and the chimeric anti-Axl antibody ch11B7 (B) of the invention were able to block ligand-induced activation of the receptor tyrosine kinase Axl to similar extent. Comparable effects applying the same experimental settings were observed with the melanoma cell line C-8161.

Example 21

Rat and Chimeric Anti-Axl Antibodies of the Invention Inhibit Ligand-Induced p42/p44 MAP-Kinase Phosphorylation In Vitro to Similar Extent To additionally verify whether the rat anti-Axl antibodies of the invention and the corresponding chimeric anti-Axl antibodies of the invention were also able to inhibit Gash-induced activation of p42/p44 MAP-Kinase in CaSki cervical cancer cells to similar extent, ELISA experiments were performed. Here, Gas6-induced p42/p44 MAP-Kinase activation was detected by increased protein (Thr202/Tyr204) phosphorylation. In brief, on the first day, $2×10^4$ cells per well were seeded in flat-bottom 96 well plates. The next day, normal growth medium was replaced by serum-free medium to starve cells for 24 h. Thereafter, cells were pre-incubated with 50 ng/ml, 100 ng/ml, 300 ng/ml, 750 ng/ml, 1 µg/ml, and 10 µg/ml of rat anti-Axl antibody 11B7 or chimeric anti-Axl antibody ch11B7 for 1 h at 37° C. and then treated with or without 400 ng/ml Gas6 (R&D Systems) for 10 min at 37° C. Medium was flicked out and cells were fixed with 4% formaldehyde in PBS (pH 7.5) for 30 min at room temperature. Formaldehyde solution was removed and cells were washed twice with wash buffer (PBS, 0.1% Tween 20). Cells were quenched with 1% $H_2O_2$, 0.1% $NaN_3$ in wash buffer and incubated for 20 min at room temperature. Afterwards, the quenching solution was removed, and cells were washed twice with wash buffer and blocked with PBS, 0.5% BSA for 4 h at room temperature. Anti-phospho-p42/p44 MAP Kinase (Thr202/Tyr204) primary antibody (polyclonal rabbit; Cell Signaling #9101) diluted 1:1,000 in PBS, 0.5% BSA, 0.05% Tween 20, 5 mM EDTA was added over night at 4° C. On day 4, the antibody solution was removed and the plate was washed 3× with wash buffer. HRP-conjugated anti-rabbit secondary antibody (Dianova #111-036-045) diluted 1:2,500 in PBS, 0.5% BSA, 0.05% Tween 20, 5 mM EDTA was then added to each well and incubated for 1.5 h at room temperature. The plate was washed 3× with wash buffer for 5 min each. Tetramethylbenzidine (TMB, Calbiochem) was added and monitored at 620 nm. The reaction was stopped by addition of 100 µl of 250 nM HCl and the absorbance was read at 450 nm with a reference wavelength of 620 nm using a Vmax plate reader (Thermo Lab Systems).

FIG. 18 shows representative results of this experiment. The rat anti-Axl antibody 11B7 (A) and the chimeric anti-Axl antibody ch11B7 (B) of the invention were able to block Gas6-induced activation of p42/p44 MAP-Kinase in CaSki cervical cancer cells to similar extent as indicated by concentration-dependent decrease of the relative p42/p44 MAP-Kinase phosphorylation.

Example 22

Rat Anti-Axl Antibodies of the Invention Synergize with Chemotherapeutic Agents to Overcome Drug Resistance In Vitro As rat anti-Axl antibodies of the invention turned out to interfere with Gas6-mediated anti-apoptosis of serum-starved NIH3T3-Axl cl.7 fibroblasts, the question arose, whether antagonistic anti-Axl antibodies would synergize with chemotherapeutic agents in inducing apoptosis, thereby contributing to overcome drug resistance. In this example, NCI/ADR-RES (originally named MCF-7/AdrR) cells—a ovarian cancer cell line (Liscovitch and Ravid, 2007, Cancer Letters, 245, 350-352) displaying a high level of resistance to several agents including doxorubicin (Fairchild et al., 1987, Cancer Research, 47, 5141-5148; Xu et al., 2002, The Journal of Pharmacology and Experimental Therapeutics, 302, 963-971)—were incubated with the antagonistic anti-Axl antibody 11B7 and/or doxorubicin, and apoptosis rates were determined by TUNEL staining. In brief, $3×10^4$ NCI/ADR-RES cells in normal growth medium were seeded per well of an 8-chamber culture slide (BD Falcon, cat#354118) which were pre-incubated with the same medium for 1 h at 37° C. The next morning, normal growth medium was removed and cells were washed with and cultured in serum-reduced (0.5% FCS) medium. In the evening, isotypic control antibody 1D5 or the antagonistic anti-Axl antibody 11B7 were added at final concentrations of 10 µg/ml each. In the morning of day 3, doxorubicin at final concentrations of 100 µM, 150 µM, or 200 µM was added, and cells were incubated at 37° C. After 24 h, cells were rinsed once with PBS, fixed with 4% formaldehyde in PBS (pH 7.5) for 20 min at room temperature, air-dried for 5 min, and stored at −20° C. Using the commercially available Fluorescein-FragEL™ kit (Oncogene, cat#QIA39, presently being distributed through Merck-Calbiochem), TUNEL staining was performed according to the supplier's manual instructions (chapter 'Fluorescein-FragEL™ of cell preparations fixed on slides', page 10). Applying fluorescence microscopy, cells were analyzed and photos were taken.

FIG. 19 shows representative results of this experiment. No TUNEL staining, and hence no apoptosis, was observed with NCI/ADR-RES ovarian cancer cells that were treated with 100 µM of doxorubicin, regardless of whether cells have been co-incubated with control antibody or the antagonistic anti-Axl antibody 11B7 (top). However, at a concentration of 150 µM of doxorubicin, only very week apoptosis could be detected in cells co-treated with control antibody, whereas co-incubation with the antagonistic anti-Axl antibody 11B7 resulted in a substantial induction of apoptosis (middle). Also in the presence of 200 µM of doxorubicin, co-incubation of cells with 11B7 significantly increased apoptosis rates as compared to cells being incubated with control IgG antibody (bottom), indicating that co-treatment of even multi drug-resistant cells with both chemotherapeutic agents and antagonistic anti-Axl antibodies of the invention may be suitable to overcome drug resistance.

Example 23

Rat Anti-Axl Antibodies of the Invention Synergize with Chemotherapeutic Agents in Reducing Anchorage-Independent Colony Growth In Vitro Soft agar assays were conducted in order to investigate the ability of anti-Axl antibodies of the invention to inhibit anchorage-independent cell growth either alone or in combination with chemotherapeutic agents. The soft agar colony formation assay is a standard in vitro assay to test for transformed cells, as only transformed cells are able to grow in soft agar.

In brief, 750 C-8161 melanoma cells either remained untreated or were pre-incubated with the antagonistic rat anti-Axl antibody 11B7 at 15 µg/ml in IMDM medium (Gibco) for 30 min at 37° C. Subsequently, cells were combined with Difco noble agar solution resulting in 50 µl of top agar cell suspension at concentrations of Agar, FCS, and 11B7 of 0.35%, 0.2%, and 7.5 µg/ml, respectively. This cell suspension was plated on top of 50 µl of a 0.7% agarose bottom layer containing 20% FCS, and was finally covered with another 50 µl of a feeding layer solution that contains 0.2% FCS as well as cisplatin in according concentrations. In the whole of 150 µl per sample, the final concentrations of 11B7 and cisplatin were 2.5 µg/ml and 1.5 µM, 1.0 µM, 0.75 µM, 0.5 µM, or 0.25 µM, respectively. Colonies were allowed to form for 5 days and were then stained with 50 µl MTT (Sigma, 1 mg/ml in PBS) for 3 hours at 37° C. Using a Scanalyzer HTS camera system in conjunction with the HTS Bonit colony formation software (Lemnatec, Wuerselen), the effect of the antagonistic rat anti-Axl antibody 11B7 in the absence or presence of cisplatin were analyzed in triplicates.

FIG. 20 shows representative results of this experiment. The presented data refer to the overall area of colonies and reflect both the absolute numbers being measured (A) and the relative growth inhibition (B) exerted by cisplatin and/or the antagonistic rat anti-Axl antibodies 11B7. As compared to untreated control cells, incubation with cisplatin led to colony growth retardation in a dose-dependent manner. In line with the inhibitory effect of 11B7 alone in the range of 30%, combination with the antagonistic anti-Axl antibody 11B7 resulted in a significantly potentiated inhibitory effect of cisplatin on soft agar growth of C-8161 melanoma cells, particularly at lower concentrations of cisplatin.

Example 24

Rat Anti-Axl Antibodies of the Invention Synergize with Anti-Neoplastic Agents in Reducing Tumor-Related Phenomena In the previous examples, synergistic effects of antagonistic anti-Axl antibodies of the invention co-administered with doxorubicin have been observed with regard to inducing apoptosis and overcoming drug resistance in multi drug-resistant cancer cells such as the ovarian cancer cell line NCI/ADR-RES. Moreover, combination effects of antagonistic anti-Axl antibodies of the invention and cisplatin in reducing anchorage-independent colony growth were detected with the melanoma cell line C-8161. Therefore, synergistic effects in inducing apoptosis in and/or overcoming drug resistance of tumor cells, suppressing tumor cell survival, inhibiting tumor cell growth and/or proliferation, reducing tumor cell migration, spreading and metastasis, or impairing tumor angiogenesis are to be expected when cancer cells or patients suffering from cancer diseases are treated with antagonistic anti-Axl antibodies in combination with irradiation and/or one or more further anti-neoplastic agent. In particular, synergistic effects in inducing apoptosis in and/or overcoming drug resistance of tumor cells, suppressing tumor cell survival, inhibiting tumor cell growth and/or proliferation, reducing tumor cell migration, spreading and metastasis, or impairing tumor angiogenesis are to be expected when melanoma cells or patients suffering from melanoma are treated with antagonistic anti-Axl antibodies in combination with irradiation and/or any further anti-neoplastic agent which is preferably but not limited to cisplatin, dacarbazine, temozolomide/temodal, muphoran/fotemustine, paclitaxel, or docetaxel. Furthermore, synergistic effects in inducing apoptosis in and/or overcoming drug resistance of tumor cells, suppressing tumor cell survival, inhibiting tumor cell growth and/or proliferation, reducing tumor cell migration, spreading and metastasis, or impairing tumor angiogenesis are to be expected when ovarian cancer cells or patients suffering from ovarian cancer are treated with antagonistic anti-Axl antibodies in combination with irradiation and/or any further anti-neoplastic agent which is preferably but not limited to doxorubicin, cisplatin, carboplatin, paclitaxel, docetaxel, melphalan, altretamine, topotecan, ifosfamide, etoposide, or 5-fluorouracil. Additionally, synergistic effects in inducing apoptosis in and/or overcoming drug resistance of tumor cells, suppressing tumor cell survival, inhibiting tumor cell growth and/or proliferation, reducing tumor cell migration, spreading and metastasis, or impairing tumor angiogenesis are to be expected when prostate cancer cells or patients suffering from prostate cancer are treated with antagonistic anti-Axl antibodies in combination with irradiation and/or any further anti-neoplastic agent which is preferably but not limited to mitozantrone, doxorubicin, paclitaxel, docetaxel, or vinblastine. Moreover, synergistic effects in inducing apoptosis in and/or overcoming drug resistance of tumor cells, suppressing tumor cell survival, inhibiting tumor cell growth and/or proliferation, reducing tumor cell migration, spreading and metastasis, or impairing tumor angiogenesis are to be expected when gastric/stomach cancer cells or patients suffering from gastric/stomach cancer are treated with antagonistic anti-Axl antibodies in combination with irradiation and/or any further anti-neoplastic agent which is preferably but not limited to 5-fluorouracil, mitomycin C, cisplatin, doxorubicin, methotrexate, etoposide, leucovorin, epirubicin, paclitaxel, docetaxel, or irinotecan. Also, synergistic effects in inducing apoptosis in and/or overcoming drug resistance of tumor cells, suppressing tumor cell survival, inhibiting tumor cell growth and/or proliferation, reducing tumor cell migration, spreading and metastasis, or impairing tumor angiogenesis are to be expected when breast cancer cells or patients suffering from breast cancer are treated with antagonistic anti-Axl antibodies in combination with irradiation and/or any further anti-neoplastic agent which is preferably but not limited to doxorubicin, epirubicin, paclitaxel, docetaxel, cyclophosphamide, 5-fluorouracil, gemcitabine, capecitabine, vinorelbine, or trastuzumab. Furthermore, synergistic effects in inducing apoptosis in and/or overcoming drug resistance of tumor cells, suppressing tumor cell survival, inhibiting tumor cell growth and/or proliferation, reducing tumor cell migration, spreading and metastasis, or impairing tumor angiogenesis are to be expected when cervical cancer cells or patients suffering from cervical cancer are treated with antagonistic anti-Axl antibodies in combination with irradiation and/or any further anti-neoplastic agent which is preferably but not limited to cisplatin, ifosfamide, irinotecan, 5-fluorouracil, paclitaxel, docetaxel, gemcitabine, or topotecan. Moreover, synergistic effects in inducing apoptosis in and/or overcoming drug resistance of tumor cells, suppressing tumor cell survival, inhibiting tumor cell growth and/or proliferation, reducing tumor cell migration, spreading and metastasis, or impairing tumor angiogenesis are to be expected when pancreatic cancer cells or patients suffering from pancreatic cancer are treated with antagonistic anti-Axl antibodies in combination with irradiation and/or any further anti-neoplastic agent which is preferably but not limited to gemcitabine, capecitabine, or 5-fluorouracil. Finally, but not excluding other cancer types, synergistic effects in inducing apoptosis in and/or overcoming drug resistance of tumor cells, suppressing tumor cell survival, inhibiting tumor cell growth and/or proliferation, reducing tumor cell migration, spreading and metastasis, or impairing tumor angiogenesis are to be expected when lung cancer cells or patients suffering from lung cancer are treated with antagonistic anti-Axl antibodies in combination with irradiation and/or any further anti-neoplastic agent which is preferably but not limited to cisplatin, carboplatin, doxorubicin, paclitaxel, docetaxel, etoposide, vinorelbine, vincristine, ifosfamide, gemcitabine, methotrexate, cyclophosphamide, lomustine, or topotecan.

The invention claimed is:

1. A monoclonal antibody that binds to the extracellular domain of AXL and at least partially inhibits AXL activity, wherein the antibody comprises a heavy chain comprising
   (a) a CDRH1 as shown in SEQ ID NO: 22,
   (b) a CDRH2 as shown in SEQ ID NO: 23, and
   (c) a CDRH3 as shown in SEQ ID NO: 24,
   and a light chain comprising
   (d) a CDRL1 as shown in SEQ ID NO: 19,
   (e) a CDRL2 as shown in SEQ ID NO: 20, and
   (f) a CDRL3 as shown in SEQ ID NO: 21,
or an monoclonal antibody recognizing the same epitope on the extracellular domain of AXL.

2. The monoclonal antibody of claim 1, which reduces and/or blocks AXL-mediated signal transduction.

3. The monoclonal antibody according to claim 1, which reduces and/or blocks AXL phosphorylation.

4. The monoclonal antibody according to claim 1, which reduces and/or blocks cell proliferation.

5. The monoclonal antibody according to claim 1, which reduces and/or blocks angiogenesis.

6. The monoclonal antibody according to claim 1, which reduces and/or blocks cell migration.

7. The monoclonal antibody according to claim 1, which reduces and/or blocks tumor metastasis.

8. The monoclonal antibody according to claim 1, which reduces and/or blocks the AXL mediated anti-apoptosis.

9. The monoclonal antibody according to claim 1, which reduces and/or blocks AXL mediated PI3K signaling.

10. The monoclonal antibody according to claim 1, which is a recombinant antibody, a humanized antibody, a chimeric antibody, a multispecific antibody, or a fragment thereof.

11. The monoclonal antibody of claim 10, which is a chimeric antibody and comprises a heavy chain amino acid sequence selected from the group consisting of SEQ ID NOs: 38, 39, 41, 42, or at least the variable domain thereof and/or a light chain amino acid sequence selected from the group consisting of SEQ ID NOs 37, 40, or at least the variable domain thereof or an antibody recognizing the same epitope on the extracellular domain of AXL.

12. The monoclonal antibody according to claim 1, which is a Fab fragment, a Fab' fragment, a F(ab'), fragment, a Fv fragment, a diabody, or a single chain antibody molecule.

13. The monoclonal antibody according to claim 1, which is of the IgG1-, IgG2-, IgG3- or IgG4-type.

14. The monoclonal antibody according to claim 1, which is coupled to a labelling group.

15. The monoclonal antibody according to claim 1, which is coupled to an effector-group.

16. The monoclonal antibody according to claim 1, which is a scaffold protein.

17. The monoclonal antibody according to claim 1, which comprises a heavy chain amino acid sequence selected from the group consisting of SEQ ID NOs: 8, 10, 12, or at least the variable domain thereof or an amino acid having a sequence identity of at least 90% thereto and/or a light chain amino acid sequence selected from the group consisting of SEQ ID NOs 7, 9, 11, or at least the variable domain thereof or an amino acid sequence having a sequence identity of at least 90% thereto or an antibody recognizing the same epitope on the extracellular domain of AXL.

18. A pharmaceutical composition comprising an anti-AXL-antibody, which is the monoclonal antibody of claim 1.

19. The pharmaceutical composition of claim 18 comprising pharmaceutically acceptable carriers, diluents and/or adjuvants.

20. The pharmaceutical composition according to claim 18, comprising a further active agent.

21. The pharmaceutical composition according to claim 19, wherein said carriers, diluents and/or adjuvant are suitable for use in a diagnostic or therapeutic composition.

22. The pharmaceutical composition according to claim 20, wherein said further active agent is suitable for screening for or treating a hyperproliferative disease associated with AXL expression, overexpression and/or hyperactivity.

23. The pharmaceutical composition of claim 22, wherein said further active agent is suitable for screening for or treating a hyperproliferative disease selected from the group consisting of breast cancer, lung cancer and other AXL expressing or overexpressing cancers, and formation of tumor metastases.

24. The monoclonal antibody according to claim 1, in combination with a carrier, diluent and/or adjuvant suitable for use in a diagnostic or therapeutic composition.

25. A kit comprising an anti-AXL-antibody, which is a monoclonal antibody according to claim 1.

26. The kit according to claim 25, further comprising a further antineoplastic agent.

27. A pharmaceutical composition comprising a polypeptide wherein said polypeptide is obtained using a vector comprising an isolated nucleic acid molecule selected from the group consisting of:
   (a) a nucleic acid sequence encoding an monoclonal antibody, antibody fragment or a derivative thereof of claim 1,
   (b) a nucleic acid sequence as shown in SEQ ID NOs: 1-6, 31-36, and
   (c) a nucleic acid complementary to any of the sequences in (a) or (b).

28. The composition according to claim 27, wherein said further active agent is selected from the group consisting of an antineoplastic agent, a small molecule inhibitor, an anti-tumor agent and a chemotherapeutic agent.

* * * * *

```
                          SEQUENCE LISTING

<160> NUMBER OF SEQ ID NOS: 84

<210> SEQ ID NO 1
<211> LENGTH: 324
<212> TYPE: DNA
<213> ORGANISM: Artificial
<220> FEATURE:
<223> OTHER INFORMATION: Rat-11B7-VLkappa-clone 33

<400> SEQUENCE: 1
gacatccaga tgacccaggc tccatcttcc ctgcctgcat ctctgggaga cagagtcact      60
attacttgcc gggcaagcca agacattgga aattatttaa gatggttcca gcagaaaccg     120
gggaaatctc ctaggcttat gatttctggt gcaaccaact tggcagctgg ggtcccatca     180
aggttcagtg gcagtaggtc tgggtcagat tattctctga ccatcagcag cctggagtct     240
gaagatatgg cagactatta ctgtctacag tctaaagagt ccccttggac gttcggtgga     300
ggcaccaagc tggagctgaa acgg                                            324

<210> SEQ ID NO 2
<211> LENGTH: 338
<212> TYPE: DNA
<213> ORGANISM: Artificial
<220> FEATURE:
<223> OTHER INFORMATION: Rat-11B7-VH-clone 20

<400> SEQUENCE: 2
gaggtgcagc ttcaggagtc aggacctggc cttgtgaaac cctcacagtc actctccctc      60
actgttctgt cactggttac tccatcacta gtaattactg gggctggatc cggaagttcc     120
caggagataa aatggagtgg atgggataca taacctacag tggtagcact agctacaacc     180
catctctcaa aagtcgaatc tccattacta gagacacatc gaagaatcag ttcttcctgc     240
agttgaactc tgtaacttct gaggacacag ccacatatta ctgtgctata caaacctttt     300
attactgggg ccaaggagtc atggtcactg tctcctca                             338

<210> SEQ ID NO 3
<211> LENGTH: 324
<212> TYPE: DNA
<213> ORGANISM: Artificial
<220> FEATURE:
<223> OTHER INFORMATION: Rat-11D5-VLkappa-clone 10

<400> SEQUENCE: 3
gacatccaga tgacccagtc tccatcctcc atgtctacat ctctgggaga cagagtcact      60
```

```
attacttgcc gggcaagtca agacattgga aattatttaa gctggttcca acagaaagta    120
gggaaatctc ctaggcgtat gatttatggt gcaatcaagt tggcagttgg ggtcccatca    180
aggttcagtg gaagtaggtc tggatcagat tattctctga ccatcagcag cctggagtct    240
gaagatatgg cgatctatta ctgtctacag tatatacagt ttccgctcac gttcggttct    300
gggaccaagc tggagctgaa acgg                                           324
```

<210> SEQ ID NO 4
<211> LENGTH: 339
<212> TYPE: DNA
<213> ORGANISM: Artificial
<220> FEATURE:
<223> OTHER INFORMATION: Rat-11D5-VH-clone 66

<400> SEQUENCE: 4

```
gaggtgcaac ttcaggagtc aggacctggc cttgtgaaac cctcacagtc actctccctc    60
acctgttctg tcactggtta ttccatcact agtaattact ggggctggat ccggaagttc    120
ccaggaaata aaatggagtg gattggacac ataaccaaca gtggtaacac tacctacaat    180
ccatctctca aaagtcgaat ctccattagt agagacacat cgaggaatca gttcttcctg    240
cagttgaact ctgtgactac tgaggacaca gccacatatt actgtgcaaa aggagcgttt    300
gattactggg gccaaggagt catggtcaca gtctcgtca                           339
```

<210> SEQ ID NO 5
<211> LENGTH: 324
<212> TYPE: DNA
<213> ORGANISM: Artificial
<220> FEATURE:
<223> OTHER INFORMATION: Rat-10D12-VLkappa-clone 8

<400> SEQUENCE: 5

```
gacatccaga tgacccaggc tccatcttcc ctgcctgcat ctctgggaga cagagtcact    60
attgcttgcc gggcaagcca agacattgga aattatttaa gatggttcca gcagaaaccg    120
gggaaatctc ctaggcttat gatttctggt gcaaccaact tggcagctgg ggtcccatca    180
aggttcagtg gcagtaggtc tgggtcagat tattctcgga ccatcagcag cctggagtct    240
gaagatatgg cagactatta ctgtctacag tctaaagagt ccccttggac gttcggtgga    300
ggcaccaagc tggagctgaa acgg                                           324
```

<210> SEQ ID NO 6
<211> LENGTH: 336
<212> TYPE: DNA
<213> ORGANISM: Artificial
<220> FEATURE:
<223> OTHER INFORMATION: Rat-10D12-VH-clone 5

<400> SEQUENCE: 6

```
gaggtgcagc ttcaggagtc aggacctggc cttgtgaagc cctcacagtc actctccctc    60
acctgctctg tcaccggtta ctccatcact agtaattact ggggctggat ccggaagttc    120
ccaggaaata aaatggagtg gatgggatac ataaccaaca gtggtggcac tgcctacaac    180
ccatctctca aaagtcgaat ctccattact agagacacat cgaagaatca gttcttcctg    240
caattgaact ctgtaattcc tgaggactca gccacatact tctgttcaag aaccccctgg    300
gactggggcc aaggagtcat ggtcacagtc tcctca                              336
```

<210> SEQ ID NO 7

```
<211> LENGTH: 108
<212> TYPE: PRT
<213> ORGANISM: Artificial
<220> FEATURE:
<223> OTHER INFORMATION: AXL antibody amino acid sequence
      Rat-11B7-VLkappa-clone 33

<400> SEQUENCE: 7

Asp Ile Gln Met Thr Gln Ala Pro Ser Ser Leu Pro Ala Ser Leu Gly
1               5                   10                  15

Asp Arg Val Thr Ile Thr Cys Arg Ala Ser Gln Asp Ile Gly Asn Tyr
            20                  25                  30

Leu Arg Trp Phe Gln Gln Lys Pro Gly Lys Ser Pro Arg Leu Met Ile
        35                  40                  45

Ser Gly Ala Thr Asn Leu Ala Ala Gly Val Pro Ser Arg Phe Ser Gly
50                  55                  60

Ser Arg Ser Gly Ser Asp Tyr Ser Leu Thr Ile Ser Ser Leu Glu Ser
65                  70                  75                  80

Glu Asp Met Ala Asp Tyr Tyr Cys Leu Gln Ser Lys Glu Ser Pro Trp
                85                  90                  95

Thr Phe Gly Gly Gly Thr Lys Leu Glu Leu Lys Arg
            100                 105

<210> SEQ ID NO 8
<211> LENGTH: 113
<212> TYPE: PRT
<213> ORGANISM: Artificial
<220> FEATURE:
<223> OTHER INFORMATION: AXL amino acid sequence     Rat-11B7-VH-clone 20

<400> SEQUENCE: 8

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Asn
            20                  25                  30

Tyr Trp Gly Trp Ile Arg Lys Phe Pro Gly Asp Lys Met Glu Trp Met
        35                  40                  45

Gly Tyr Ile Thr Tyr Ser Gly Ser Thr Ser Tyr Asn Pro Ser Leu Lys
50                  55                  60

Ser Arg Ile Ser Ile Thr Arg Asp Thr Ser Lys Asn Gln Phe Phe Leu
65                  70                  75                  80

Gln Leu Asn Ser Val Thr Ser Glu Asp Thr Ala Thr Tyr Tyr Cys Ala
                85                  90                  95

Ile Thr Thr Phe Tyr Tyr Trp Gly Gln Gly Val Met Val Thr Val Ser
            100                 105                 110

Ser

<210> SEQ ID NO 9
<211> LENGTH: 108
<212> TYPE: PRT
<213> ORGANISM: Artificial
<220> FEATURE:
<223> OTHER INFORMATION: AXL antibody amino acid sequence
      Rat-11D5-VLkappa-clone 10

<400> SEQUENCE: 9

Asp Ile Gln Met Thr Gln Ser Pro Ser Ser Met Ser Thr Ser Leu Gly
1               5                   10                  15

Asp Arg Val Thr Ile Thr Cys Arg Ala Ser Gln Asp Ile Gly Asn Tyr
            20                  25                  30
```

```
Leu Ser Trp Phe Gln Gln Lys Val Gly Lys Ser Pro Arg Arg Met Ile
            35                  40                  45

Tyr Gly Ala Ile Lys Leu Ala Val Gly Val Pro Ser Arg Phe Ser Gly
        50                  55                  60

Ser Arg Ser Gly Ser Asp Tyr Ser Leu Thr Ile Ser Ser Leu Glu Ser
65                  70                  75                  80

Glu Asp Met Ala Ile Tyr Tyr Cys Leu Gln Tyr Ile Gln Phe Pro Leu
                85                  90                  95

Thr Phe Gly Ser Gly Thr Lys Leu Glu Leu Lys Arg
            100                 105
```

<210> SEQ ID NO 10
<211> LENGTH: 113
<212> TYPE: PRT
<213> ORGANISM: Artificial
<220> FEATURE:
<223> OTHER INFORMATION: AXL antibody amino acid sequence
      Rat-11D5-VH-clone 66

<400> SEQUENCE: 10

```
Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Asn
            20                  25                  30

Tyr Trp Gly Trp Ile Arg Lys Phe Pro Gly Asn Lys Met Glu Trp Ile
            35                  40                  45

Gly His Ile Thr Asn Ser Gly Asn Thr Thr Tyr Asn Pro Ser Leu Lys
        50                  55                  60

Ser Arg Ile Ser Ile Ser Arg Asp Thr Ser Arg Asn Gln Phe Phe Leu
65                  70                  75                  80

Gln Leu Asn Ser Val Thr Thr Glu Asp Thr Ala Thr Tyr Tyr Cys Ala
                85                  90                  95

Lys Gly Ala Phe Asp Tyr Trp Gly Gln Gly Val Met Val Thr Val Ser
            100                 105                 110

Ser
```

<210> SEQ ID NO 11
<211> LENGTH: 108
<212> TYPE: PRT
<213> ORGANISM: Artificial
<220> FEATURE:
<223> OTHER INFORMATION: AXL antibody amino acid sequence
      Rat-10D12-VLkappa-clone 8

<400> SEQUENCE: 11

```
Asp Ile Gln Met Thr Gln Ala Pro Ser Ser Leu Pro Ala Ser Leu Gly
1               5                   10                  15

Asp Arg Val Thr Ile Ala Cys Arg Ala Ser Gln Asp Ile Gly Asn Tyr
            20                  25                  30

Leu Arg Trp Phe Gln Gln Lys Pro Gly Lys Ser Pro Arg Leu Met Ile
            35                  40                  45

Ser Gly Ala Thr Asn Leu Ala Ala Gly Val Pro Ser Arg Phe Ser Gly
        50                  55                  60

Ser Arg Ser Gly Ser Asp Tyr Ser Arg Thr Ile Ser Ser Leu Glu Ser
65                  70                  75                  80

Glu Asp Met Ala Asp Tyr Tyr Cys Leu Gln Ser Lys Glu Ser Pro Trp
                85                  90                  95
```

```
Thr Phe Gly Gly Gly Thr Lys Leu Glu Leu Lys Arg
            100                 105

<210> SEQ ID NO 12
<211> LENGTH: 112
<212> TYPE: PRT
<213> ORGANISM: Artificial
<220> FEATURE:
<223> OTHER INFORMATION: AXL antibody amino acid sequence
      Rat-10D12-VH-clone 5

<400> SEQUENCE: 12

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Asn
            20                  25                  30

Tyr Trp Gly Trp Ile Arg Lys Phe Pro Gly Asn Lys Met Glu Trp Met
        35                  40                  45

Gly Tyr Ile Thr Asn Ser Gly Gly Thr Ala Tyr Asn Pro Ser Leu Lys
    50                  55                  60

Ser Arg Ile Ser Ile Thr Arg Asp Thr Ser Lys Asn Gln Phe Phe Leu
65                  70                  75                  80

Gln Leu Asn Ser Val Ile Pro Glu Asp Ser Ala Thr Tyr Phe Cys Ser
                85                  90                  95

Arg Thr Pro Trp Asp Trp Gly Gln Gly Val Met Val Thr Val Ser Ser
            100                 105                 110

<210> SEQ ID NO 13
<211> LENGTH: 11
<212> TYPE: PRT
<213> ORGANISM: Artificial
<220> FEATURE:
<223> OTHER INFORMATION: 11B7 light chain   CDR 1

<400> SEQUENCE: 13

Arg Ala Ser Gln Asp Ile Gly Asn Tyr Leu Arg
1               5                   10

<210> SEQ ID NO 14
<211> LENGTH: 7
<212> TYPE: PRT
<213> ORGANISM: Artificial
<220> FEATURE:
<223> OTHER INFORMATION: 11B7 light chain   CDR 2

<400> SEQUENCE: 14

Gly Ala Thr Asn Leu Ala Ala
1               5

<210> SEQ ID NO 15
<211> LENGTH: 9
<212> TYPE: PRT
<213> ORGANISM: Artificial
<220> FEATURE:
<223> OTHER INFORMATION: 11B7 light chain   CDR 3

<400> SEQUENCE: 15

Leu Gln Ser Lys Glu Ser Pro Trp Thr
1               5

<210> SEQ ID NO 16
<211> LENGTH: 5
<212> TYPE: PRT
<213> ORGANISM: Artificial
```

```
<220> FEATURE:
<223> OTHER INFORMATION: 11B7 heavy chain    CDR 1

<400> SEQUENCE: 16

Ser Asn Tyr Trp Gly
1               5

<210> SEQ ID NO 17
<211> LENGTH: 16
<212> TYPE: PRT
<213> ORGANISM: Artificial
<220> FEATURE:
<223> OTHER INFORMATION: 11B7 heavy chain    CDR 2

<400> SEQUENCE: 17

Tyr Ile Thr Tyr Ser Gly Ser Thr Ser Tyr Asn Pro Ser Leu Lys Ser
1               5                   10                  15

<210> SEQ ID NO 18
<211> LENGTH: 5
<212> TYPE: PRT
<213> ORGANISM: Artificial
<220> FEATURE:
<223> OTHER INFORMATION: 11B7 heavy chain    CDR 3

<400> SEQUENCE: 18

Thr Thr Phe Tyr Tyr
1               5

<210> SEQ ID NO 19
<211> LENGTH: 11
<212> TYPE: PRT
<213> ORGANISM: Artificial
<220> FEATURE:
<223> OTHER INFORMATION: 11D5 light chain    CDR 1

<400> SEQUENCE: 19

Arg Ala Ser Gln Asp Ile Gly Asn Tyr Leu Ser
1               5                   10

<210> SEQ ID NO 20
<211> LENGTH: 7
<212> TYPE: PRT
<213> ORGANISM: Artificial
<220> FEATURE:
<223> OTHER INFORMATION: 11D5 light chain    CDR 2

<400> SEQUENCE: 20

Gly Ala Ile Lys Leu Ala Val
1               5

<210> SEQ ID NO 21
<211> LENGTH: 9
<212> TYPE: PRT
<213> ORGANISM: Artificial
<220> FEATURE:
<223> OTHER INFORMATION: 11D5 light chain    CDR 3

<400> SEQUENCE: 21

Leu Gln Tyr Ile Gln Phe Pro Leu Thr
1               5

<210> SEQ ID NO 22
<211> LENGTH: 5
<212> TYPE: PRT
<213> ORGANISM: Artificial
<220> FEATURE:
```

<223> OTHER INFORMATION: 11D5 heavy chain   CDR 1

<400> SEQUENCE: 22

Ser Asn Tyr Trp Gly
1               5

<210> SEQ ID NO 23
<211> LENGTH: 16
<212> TYPE: PRT
<213> ORGANISM: Artificial
<220> FEATURE:
<223> OTHER INFORMATION: 11D5 heavy chain   CDR 2

<400> SEQUENCE: 23

His Ile Thr Asn Ser Gly Asn Thr Thr Tyr Asn Pro Ser Leu Lys Ser
1               5                   10                  15

<210> SEQ ID NO 24
<211> LENGTH: 5
<212> TYPE: PRT
<213> ORGANISM: Artificial
<220> FEATURE:
<223> OTHER INFORMATION: 11D5 heavy chain   CDR 3

<400> SEQUENCE: 24

Gly Ala Phe Asp Tyr
1               5

<210> SEQ ID NO 25
<211> LENGTH: 11
<212> TYPE: PRT
<213> ORGANISM: Artificial
<220> FEATURE:
<223> OTHER INFORMATION: 10D12 light chain   CDR 1

<400> SEQUENCE: 25

Arg Ala Ser Gln Asp Ile Gly Asn Tyr Leu Arg
1               5                   10

<210> SEQ ID NO 26
<211> LENGTH: 7
<212> TYPE: PRT
<213> ORGANISM: Artificial
<220> FEATURE:
<223> OTHER INFORMATION: 10D12 light chain   CDR2

<400> SEQUENCE: 26

Gly Ala Thr Asn Leu Ala Ala
1               5

<210> SEQ ID NO 27
<211> LENGTH: 9
<212> TYPE: PRT
<213> ORGANISM: Artificial
<220> FEATURE:
<223> OTHER INFORMATION: 10D12 light chain   CDR3

<400> SEQUENCE: 27

Leu Gln Ser Lys Glu Ser Pro Trp Thr
1               5

<210> SEQ ID NO 28
<211> LENGTH: 5
<212> TYPE: PRT
<213> ORGANISM: Artificial
<220> FEATURE:
<223> OTHER INFORMATION: 10D12 heavy chain   CDR1

<400> SEQUENCE: 28

Ser Asn Tyr Trp Gly
1               5

<210> SEQ ID NO 29
<211> LENGTH: 16
<212> TYPE: PRT
<213> ORGANISM: Artificial
<220> FEATURE:
<223> OTHER INFORMATION: 10D12 heavy chain   CDR2

<400> SEQUENCE: 29

Tyr Ile Thr Asn Ser Gly Gly Thr Ala Tyr Asn Pro Ser Leu Lys Ser
1               5                   10                  15

<210> SEQ ID NO 30
<211> LENGTH: 4
<212> TYPE: PRT
<213> ORGANISM: Artificial
<220> FEATURE:
<223> OTHER INFORMATION: 10D12 heavy chain   CDR3

<400> SEQUENCE: 30

Thr Pro Trp Asp
1

<210> SEQ ID NO 31
<211> LENGTH: 645
<212> TYPE: DNA
<213> ORGANISM: Artificial
<220> FEATURE:
<223> OTHER INFORMATION: ch11B7k

<400> SEQUENCE: 31
gacatccaga tgacccaggc tccatcttcc ctgcctgcat ctctgggaga cagagtcact    60
attacttgcc gggcaagcca agacattgga aattatttaa atggttccag cagaaaccg    120 gggaaatctc ctaggcttat gatttctggt gcaaccaact ggcagctggg gtcccatca    180 aggttcagtg gcagtaggtc tgggtcagat tattctctga ccatcagcag cctggagtct    240
gaagatatgg cagactatta ctgtctacag tctaaagagt cccccttgga cgttcggtgga    300 ggcaccaagc tggagctgaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                   645

<210> SEQ ID NO 32
<211> LENGTH: 1332
<212> TYPE: DNA
<213> ORGANISM: Artificial
<220> FEATURE:
<223> OTHER INFORMATION: ch11B7g1

<400> SEQUENCE: 32
gaggtgcagc ttcaggagtc aggacctggc cttgtgaaac cctcacagtc actctccctc    60
acctgttctg tcactggtta ctccatcact agtaattact ggggctggat ccggaagttc    120
ccaggagata aaatggagtg gatgggatac ataacctaca gtggtagcac tagctacaac    180

```
ccatctctca aaagtcgaat ctccattact agagacacat cgaagaatca gttcttcctg      240
cagttgaact ctgtaacttc tgaggacaca gccacatatt actgtgctat aacaaccttt      300
tattactggg gccaaggagt catggtcact gtcagctcag cgtccaccaa gggcccatcg      360
gtcttccccc tggcaccctc ctccaagagc acctctgggg cacagcggc cctgggctgc       420 ctggtcaagg actacttccc cgaaccggtg acggtgtcgt ggaactcagg cgccctgacc      480
agcggcgtgc acaccttccc ggctgtccta cagtcctcag gactctactc cctcagcagc      540
gtggtgaccg tgcccccag cagcttgggc acccagacct acatctgcaa cgtgaatcac       600
aagcccagca caccaaggt ggacaagaaa gttgagccca atcttgtga caaaactcac        660 acatgcccac cgtgcccagc acctgaactc ctggggggac cgtcagtctt cctcttcccc      720
ccaaaaccca aggacaccct catgatctcc cggacccctg aggtcacatg cgtggtggtg      780
gacgtgagcc acgaagaccc tgaggtcaag ttcaactggt acgtggacgg cgtggaggtg      840
cataatgcca agacaaagcc gcgggaggag cagtacaaca gcacgtaccg ggtggtcagt      900
cgtcctcacc gtcctgcacc aggactggct gaatggcaag gagtacaagg caaggtctcc      960
aacaaagccc tcccagcccc catcgagaaa accatctcca agccaaagg gcagccccga      1020 gaaccacagg tgtacaccct gcccccatcc cgggatgagc tgaccaagaa ccaggtcagc     1080
ctgacctgcc tggtcaaagg cttctatccc agcgacatcg ccgtggagtg ggagagcaat     1140
gggcagccgg agaacaacta caagaccacg cctcccgtgc tggactccga cggctccttc     1200
ttcctctaca gcaagctcac cgtggacaag agcaggtggc agcaggggaa cgtcttctca     1260
tgctccgtga tgcatgaggc tctgcacaac cactacacgc agaagagcct ctccctgtct     1320
ccgggtaaat ga                                                         1332
```

<210> SEQ ID NO 33
<211> LENGTH: 1320
<212> TYPE: DNA
<213> ORGANISM: Artificial
<220> FEATURE:
<223> OTHER INFORMATION: ch11B7g2

<400> SEQUENCE: 33

```
gaggtgcagc ttcaggagtc aggacctggc cttgtgaaac cctcacagtc actctccctc       60
acctgttctg tcactggtta ctccatcact agtaattact ggggctggat ccggaagttc      120
ccaggagata aaatggagtg gatgggatac ataacctaca gtggtagcac tagctacaac      180
ccatctctca aaagtcgaat ctccattact agagacacat cgaagaatca gttcttcctg      240
cagttgaact ctgtaacttc tgaggacaca gccacatatt actgtgctat aacaaccttt      300
tattactggg gccaaggagt catggtcact gtcagctcag cgtccaccaa gggcccatcg      360
gtcttccccc tggcgccctg ctccaggagc acctccgaga gcacagccgc cctgggctgc      420
ctggtcaagg actacttccc cgaaccggtg acggtgtcgt ggaactcagg cgctctgacc      480
agcggcgtgc acaccttccc agctgtccta cagtcctcag gactctactc cctcagcagc      540
gtggtgaccg tgcccccag caacttcggc acccagacct acacctgcaa cgtagatcac       600
aagcccagca caccaaggt ggacaagaca gttgagcgca atgttgtgt cgagtgccca        660 ccgtgcccag caccacctgt ggcaggaccg tcagtcttcc tcttcccccc aaaacccaag      720
gacaccctca tgatctcccg gacccctgag gtcacgtgcg tggtggtgga cgtgagccac      780 gaagacccg aggtccagtt caactggtac gtggacggcg tggaggtgca taatgccaag      840
```

| | |
|---|---|
| acaaagccac gggaggagca gttcaacagc acgttccgtg tggtcagcgt cctcaccgtt | 900 |
| gtgcaccagg actggctgaa cggcaaggag tacaagtgca aggtctccaa caaaggcctc | 960 |
| ccagccccca tcgagaaaac catctccaaa accaaagggc agccccgaga ccacaggtg | 1020 |
| tacaccctgc ccccatcccg ggaggagatg accaagaacc aggtcagcct gacctgcctg | 1080 |
| gtcaaaggct tctaccccag cgacatcgcc gtggagtggg agagcaatgg gcagccggag | 1140 |
| aacaactaca agaccacacc tcccatgctg gactccgacg gctccttctt cctctacagc | 1200 |
| aagctcaccg tggacaagag caggtggcag caggggaacg tcttctcatg ctccgtgatg | 1260 |
| catgaggctc tgcacaacca ctacacgcag aagagcctct ccctgtctcc gggtaaatga | 1320 |

<210> SEQ ID NO 34
<211> LENGTH: 645
<212> TYPE: DNA
<213> ORGANISM: Artificial
<220> FEATURE:
<223> OTHER INFORMATION: ch11D5k

<400> SEQUENCE: 34

| | |
|---|---|
| gacatccaga tgacccagtc tccatcctcc atgtctacat ctctgggaga cagagtcacc | 60 |
| attacttgcc gggcaagtca agacattgga aattatttaa gctggttcca acagaaagta | 120 |
| gggaaatctc ctaggcgtat gatttatggt gcaatcaagt tggcagttgg ggtcccatca | 180 |
| aggttcagtg gaagtaggtc tggatcagat tattctctga ccatcagcag cctggagtct | 240 |
| gaagatatgg cgatctatta ctgtctacag tatatacagt ttccgctcac gttcggttct | 300 |
| gggaccaagc tggagctgaa acgtacggtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gttag | 645 |

<210> SEQ ID NO 35
<211> LENGTH: 1332
<212> TYPE: DNA
<213> ORGANISM: Artificial
<220> FEATURE:
<223> OTHER INFORMATION: ch11D5g1

<400> SEQUENCE: 35

| | |
|---|---|
| gaggtgcaac ttcaggagtc aggacctggc cttgtgaaac cctcacagtc actctccctc | 60 |
| acctgttctg tcactggtta ttccatcact agtaattact ggggctggat ccggaagttc | 120 |
| ccaggaaata aaatggagtg gattggacac ataaccaaca gtggtaacac tacctacaat | 180 |
| ccatctctca aaagtcgaat ctccattagt agagacacat cgaggaatca gttcttcctg | 240 |
| cagttgaact ctgtgactac tgaggacaca gccacatatt actgtgcaaa aggagcgttt | 300 |
| gattactggg gccaaggagt catggtcact gtcagctcag cgtccaccaa gggcccatcg | 360 |
| gtcttccccc tggcaccctc ctccaagagc acctctgggg cacagcggc cctgggctgc | 420 |
| ctggtcaagg actacttccc cgaaccggtg acggtgtcgt ggaactcagg cgccctgacc | 480 |
| agcggcgtgc acaccttccc ggctgtccta cagtcctcag gactctactc cctcagcagc | 540 |
| gtggtgaccg tgcctccag cagcttgggc acccagacct acatctgcaa cgtgaatcac | 600 |
| aagcccagca acaccaaggt ggacaagaaa gttgagccca atcttgtga caaaactcac | 660 |

```
acatgcccac cgtgcccagc acctgaactc ctgggggac cgtcagtctt cctcttcccc      720
ccaaaaccca aggacaccct catgatctcc cggacccctg aggtcacatg cgtggtggtg      780
gacgtgagcc acgaagaccc tgaggtcaag ttcaactggt acgtggacgg cgtggaggtg      840
cataatgcca agacaaagcc gcgggaggag cagtacaaca gcacgtaccg ggtggtcagc      900
gtcctcaccg tcctgcacca ggactggctg aatggcaagg agtacaagtg caaggtctcc      960
aacaaagccc tcccagcccc catcgagaaa accatctcca aagccaaagg gcagccccga     1020
gaaccacagg tgtacaccct gcccccatcc cgggatgagc tgaccaagaa ccaggtcagc     1080
ctgacctgcc tggtcaaagg cttctatccc agcgacatcg ccgtggagtg ggagagcaat     1140
gggcagccgg agaacaacta caagaccacg cctcccgtgc tggactccga cggctccttc     1200
ttcctctaca gcaagctcac cgtggacaag agcaggtggc agcaggggaa cgtcttctca     1260
tgctccgtga tgcatgaggc tctgcacaac cactacacgc agaagagcct ctccctgtct     1320
ccgggtaaat ga                                                         1332

<210> SEQ ID NO 36
<211> LENGTH: 1320
<212> TYPE: DNA
<213> ORGANISM: Artificial
<220> FEATURE:
<223> OTHER INFORMATION: ch11D5g2

<400> SEQUENCE: 36
gaggtgcaac ttcaggagtc aggacctggc cttgtgaaac cctcacagtc actctccctc       60
acctgttctg tcactggtta ttccatcact agtaattact ggggctggat ccggaagttc      120
ccaggaaata aaatggagtg gattggacac ataaccaaca gtggtaacac tacctacaat      180
ccatctctca aaagtcgaat ctccattagt agagacacat cgaggaatca gttcttcctg      240
cagttgaact ctgtgactac tgaggacaca gccacatatt actgtgcaaa aggagcgttt      300
gattactggg gccaaggagt catggtcact gtcagctcag cgtccaccaa gggcccatcg      360
gtcttccccc tggcgccctg ctccaggagc acctccgaga gcacagccgc cctgggctgc      420
ctggtcaagg actacttccc cgaaccggtg acggtgtcgt ggaactcagg cgctctgacc      480
agcggcgtgc acaccttccc agctgtccta cagtcctcag gactctactc cctcagcagc      540
gtggtgaccg tgcctccag caacttcggc acccagacct acacctgcaa cgtagatcac      600
aagcccagca acaccaaggt ggacaagaca gttgagcgca aatgttgtgt cgagtgccca      660
ccgtgcccag caccacctgt ggcaggaccg tcagtcttcc tcttcccccc aaaacccaag      720
gacaccctca tgatctcccg gacccctgag gtcacgtgcg tggtggtgga cgtgagccac      780
gaagaccccg aggtccagtt caactggtac gtggacggcg tggaggtgca taatgccaag      840
acaaagccac gggaggagca gttcaacagc acgttccgtg tggtcagcgt cctcaccgtt      900
gtgcaccagg actggctgaa cggcaaggag tacaagtgca aggtctccaa caaaggcctc      960
ccagccccca tcgagaaaac catctccaaa accaaagggc agccccgaga accacaggtg     1020
tacaccctgc cccatcccg ggaggagatg accaagaacc aggtcagcct gacctgcctg     1080
gtcaaaggct tctaccccag cgacatcgcc gtggagtggg agcaatggg gcagccggag     1140 aacaactaca agaccacacc tcccatgctg gactccgacg gctccttctt cctctacagc     1200
aagctcaccg tggacaagag caggtggcag caggggaacg tcttctcatg ctccgtgatg     1260
catgaggctc tgcacaacca ctacacgcag aagagcctct ccctgtctcc gggtaaatga     1320
```

<210> SEQ ID NO 37
<211> LENGTH: 214
<212> TYPE: PRT
<213> ORGANISM: Artificial
<220> FEATURE:
<223> OTHER INFORMATION: 11B7 LC kappa

<400> SEQUENCE: 37

Asp Ile Gln Met Thr Gln Ala Pro Ser Ser Leu Pro Ala Ser Leu Gly
1               5                   10                  15

Asp Arg Val Thr Ile Thr Cys Arg Ala Ser Gln Asp Ile Gly Asn Tyr
            20                  25                  30

Leu Arg Trp Phe Gln Gln Lys Pro Gly Lys Ser Pro Arg Leu Met Ile
        35                  40                  45

Ser Gly Ala Thr Asn Leu Ala Ala Gly Val Pro Ser Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Met Ala Asp Tyr Tyr Cys Leu Gln Ser Lys Glu Ser Pro Trp
                85                  90                  95

Thr Phe Gly Gly Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 38
<211> LENGTH: 443
<212> TYPE: PRT
<213> ORGANISM: Artificial
<220> FEATURE:
<223> OTHER INFORMATION: 11B7-HCgamma1

<400> SEQUENCE: 38

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Asn
            20                  25                  30

Tyr Trp Gly Trp Ile Arg Lys Phe Pro Gly Asp Lys Met Glu Trp Met
        35                  40                  45

Gly Tyr Ile Thr Tyr Ser Gly Ser Thr Ser Tyr Asn Pro Ser Leu Lys
    50                  55                  60

Ser Arg Ile Ser Ile Thr Arg Asp Thr Ser Lys Asn Gln Phe Phe Leu
65                  70                  75                  80

Gln Leu Asn Ser Val Thr Ser Glu Asp Thr Ala Thr Tyr Tyr Cys Ala
                85                  90                  95

Ile Thr Thr Phe Tyr Tyr Trp Gly Gln Gly Val Met Val Thr Val Ser
            100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 39
<211> LENGTH: 439
<212> TYPE: PRT
<213> ORGANISM: Artificial
<220> FEATURE:
<223> OTHER INFORMATION: 11B7 HC gamma2

<400> SEQUENCE: 39

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Asn
            20                  25                  30

Tyr Trp Gly Trp Ile Arg Lys Phe Pro Gly Asp Lys Met Glu Trp Met
        35                  40                  45

Gly Tyr Ile Thr Tyr Ser Gly Ser Thr Ser Tyr Asn Pro Ser Leu Lys
    50                  55                  60

Ser Arg Ile Ser Ile Thr Arg Asp Thr Ser Lys Asn Gln Phe Phe Leu
65                  70                  75                  80

Gln Leu Asn Ser Val Thr Ser Glu Asp Thr Ala Thr Tyr Tyr Cys Ala
                85                  90                  95

Ile Thr Thr Phe Tyr Tyr Trp Gly Gln Gly Val Met Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Asn Phe Gly Thr Gln
            180                 185                 190

Thr Tyr Thr Cys Asn Val Asp His Lys Pro Ser Asn Thr Lys Val Asp
        195                 200                 205

Lys Thr Val Glu Arg Lys Cys Cys Val Glu Cys Pro Pro Cys Pro Ala
    210                 215                 220

Pro Pro Val Ala Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
        275                 280                 285

Asn Ser Thr Phe Arg Val Val Ser Val Leu Thr Val Val His Gln Asp
290                 295                 300

Trp Leu Asn Gly Lys Glu Tyr Lys Cys Lys Val Ser Asn Lys Gly Leu
305                 310                 315                 320

Pro Ala Pro Ile Glu Lys Thr Ile Ser Lys Thr Lys Gly Gln Pro Arg
                325                 330                 335

Glu Pro Gln Val Tyr Thr Leu Pro Pro Ser Arg Glu Glu Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

Thr Thr Pro Pro Met Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
            420                 425                 430

```
Leu Ser Leu Ser Pro Gly Lys
        435

<210> SEQ ID NO 40
<211> LENGTH: 214
<212> TYPE: PRT
<213> ORGANISM: Artificial
<220> FEATURE:
<223> OTHER INFORMATION: 11D5 LC kappa

<400> SEQUENCE: 40

Asp Ile Gln Met Thr Gln Ser Pro Ser Ser Met Ser Thr Ser Leu Gly
1               5                   10                  15

Asp Arg Val Thr Ile Thr Cys Arg Ala Ser Gln Asp Ile Gly Asn Tyr
            20                  25                  30

Leu Ser Trp Phe Gln Gln Lys Val Gly Lys Ser Pro Arg Arg Met Ile
        35                  40                  45

Tyr Gly Ala Ile Lys Leu Ala Val Gly Val Pro Ser Arg Phe Ser Gly
50                  55                  60

Ser Arg Ser Gly Ser Asp Tyr Ser Leu Thr Ile Ser Ser Leu Glu Ser
65                  70                  75                  80

Glu Asp Met Ala Ile Tyr Tyr Cys Leu Gln Tyr Ile Gln Phe Pro Leu
                85                  90                  95

Thr Phe Gly Ser Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 41
<211> LENGTH: 443
<212> TYPE: PRT
<213> ORGANISM: Artificial
<220> FEATURE:
<223> OTHER INFORMATION: 11D5 HC gamma1

<400> SEQUENCE: 41

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Asn
            20                  25                  30

Tyr Trp Gly Trp Ile Arg Lys Phe Pro Gly Asn Lys Met Glu Trp Ile
        35                  40                  45

Gly His Ile Thr Asn Ser Gly Asn Thr Thr Tyr Asn Pro Ser Leu Lys
50                  55                  60

Ser Arg Ile Ser Ile Ser Arg Asp Thr Ser Arg Asn Gln Phe Phe Leu
65                  70                  75                  80
```

```
Gln Leu Asn Ser Val Thr Thr Glu Asp Thr Ala Thr Tyr Tyr Cys Ala
                85                  90                  95

Lys Gly Ala Phe Asp Tyr Trp Gly Gln Gly Val Met Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
                180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
                260                 265                 270

Trp Tyr Val Asp Gly Val Glu Val His Asn Ala Lys Thr Lys Pro Arg
            275                 280                 285

Glu Glu Gln Tyr Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly Lys
                435                 440

<210> SEQ ID NO 42
<211> LENGTH: 439
<212> TYPE: PRT
<213> ORGANISM: Artificial
<220> FEATURE:
<223> OTHER INFORMATION: 11D5 HC gamma2

<400> SEQUENCE: 42
```

-continued

```
Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Asn
            20                  25                  30

Tyr Trp Gly Trp Ile Arg Lys Phe Pro Gly Asn Lys Met Glu Trp Ile
        35                  40                  45

Gly His Ile Thr Asn Ser Gly Asn Thr Tyr Asn Pro Ser Leu Lys
    50                  55                  60

Ser Arg Ile Ser Ile Ser Arg Asp Thr Ser Arg Asn Gln Phe Phe Leu
65                  70                  75                  80

Gln Leu Asn Ser Val Thr Thr Glu Asp Thr Ala Thr Tyr Tyr Cys Ala
                85                  90                  95

Lys Gly Ala Phe Asp Tyr Trp Gly Gln Gly Val Met Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Asn Phe Gly Thr Gln
            180                 185                 190

Thr Tyr Thr Cys Asn Val Asp His Lys Pro Ser Asn Thr Lys Val Asp
        195                 200                 205

Lys Thr Val Glu Arg Lys Cys Cys Val Glu Cys Pro Pro Cys Pro Ala
    210                 215                 220

Pro Pro Val Ala Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
        275                 280                 285

Asn Ser Thr Phe Arg Val Val Ser Val Leu Thr Val Val His Gln Asp
    290                 295                 300

Trp Leu Asn Gly Lys Glu Tyr Lys Cys Lys Val Ser Asn Lys Gly Leu
305                 310                 315                 320

Pro Ala Pro Ile Glu Lys Thr Ile Ser Lys Thr Lys Gly Gln Pro Arg
                325                 330                 335

Glu Pro Gln Val Tyr Thr Leu Pro Pro Ser Arg Glu Glu Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

Thr Thr Pro Pro Met Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415
```

```
Cys Ser Val Met His Glu Ala Leu His Asn His Tyr Thr Gln Lys Ser
            420                 425                 430
Leu Ser Leu Ser Pro Gly Lys
        435

<210> SEQ ID NO 43
<211> LENGTH: 128
<212> TYPE: PRT
<213> ORGANISM: Artificial
<220> FEATURE:
<223> OTHER INFORMATION: Hum11B7-VLk

<400> SEQUENCE: 43

Met Asp Met Arg Val Pro Ala Gln Leu Leu Gly Leu Leu Leu Leu Trp
1               5                   10                  15
Leu Arg Gly Ala Arg Cys Asp Ile Gln Met Thr Gln Ser Pro Ser Ser
            20                  25                  30
Leu Ser Ala Ser Val Gly Asp Arg Val Thr Ile Thr Cys Arg Ala Ser
        35                  40                  45
Gln Asp Ile Gly Asn Leu Arg Trp Tyr Gln Gln Lys Pro Gly Lys Ala
    50                  55                  60
Pro Lys Leu Leu Ile Tyr Gly Ala Thr Asn Leu Ala Ala Gly Val Pro
65                  70                  75                  80
Ser Arg Phe Ser Gly Ser Gly Ser Gly Thr Asp Phe Thr Leu Thr Ile
                85                  90                  95
Ser Ser Leu Gln Pro Glu Asp Phe Ala Thr Tyr Tyr Cys Leu Gln Ser
            100                 105                 110
Lys Glu Ser Pro Trp Thr Phe Gly Gln Gly Thr Lys Val Glu Ile Lys
        115                 120                 125

<210> SEQ ID NO 44
<211> LENGTH: 132
<212> TYPE: PRT
<213> ORGANISM: Artificial
<220> FEATURE:
<223> OTHER INFORMATION: Hum11B7-VH

<400> SEQUENCE: 44

Met Lys His Leu Trp Phe Phe Leu Leu Leu Val Ala Ala Pro Arg Trp
1               5                   10                  15
Val Leu Ser Gln Val Gln Leu Gln Glu Ser Gly Pro Gly Leu Val Lys
            20                  25                  30
Pro Ser Glu Thr Leu Ser Leu Thr Cys Thr Val Ser Gly Gly Ser Ile
        35                  40                  45
Ser Ser Asn Tyr Trp Gly Trp Ile Arg Gln Pro Pro Gly Lys Gly Leu
    50                  55                  60
Glu Trp Ile Gly Tyr Ile Thr Tyr Ser Gly Thr Ser Tyr Asn Pro
65                  70                  75                  80
Ser Leu Lys Ser Arg Val Thr Ile Ser Val Asp Thr Ser Lys Asn Gln
                85                  90                  95
Phe Ser Leu Lys Leu Ser Ser Val Thr Ala Ala Asp Thr Ala Val Tyr
            100                 105                 110
Tyr Cys Ala Arg Thr Thr Phe Tyr Tyr Trp Gly Gln Gly Thr Leu Val
        115                 120                 125
Thr Val Ser Ser
    130

<210> SEQ ID NO 45
```

```
<211> LENGTH: 132
<212> TYPE: PRT
<213> ORGANISM: Artificial
<220> FEATURE:
<223> OTHER INFORMATION: Hum11D5-VH

<400> SEQUENCE: 45

Met Lys His Leu Trp Phe Phe Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
                35                  40                  45

Ser Ser Asn Tyr Trp Gly Trp Ile Arg Gln Pro Pro Gly Lys Gly Leu
    50                  55                  60

Glu Trp Ile Gly His Ile Thr Asn Ser Gly Asn Thr Thr Tyr Asn Pro
65                  70                  75                  80

Ser Leu Lys Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Gly Ala Phe Asp Tyr Trp Gly Gln Gly Thr Leu Val
        115                 120                 125

Thr Val Ser Ser
    130

<210> SEQ ID NO 46
<211> LENGTH: 129
<212> TYPE: PRT
<213> ORGANISM: Artificial
<220> FEATURE:
<223> OTHER INFORMATION: Hum11D5-VLk

<400> SEQUENCE: 46

Met Asp Met Arg Val Leu Ala Gln Leu Leu Gly Leu Leu Leu Leu Cys
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
                35                  40                  45

Gln Asp Ile Gly Asn Tyr Leu Ser Trp Phe Gln Gln Lys Pro Gly Lys
    50                  55                  60

Ala Pro Lys Ser Leu Ile Tyr Gly Ala Ile Lys Leu Ala Val Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Leu Gln
            100                 105                 110

Tyr Ile Gln Phe Pro Leu Thr Phe Gly Gly Thr Lys Val Glu Ile
        115                 120                 125

Lys

<210> SEQ ID NO 47
<211> LENGTH: 427
<212> TYPE: DNA
<213> ORGANISM: Artificial
<220> FEATURE:
<223> OTHER INFORMATION: Hum11B7-VLk
```

<400> SEQUENCE: 47

```
aattaaaagc tagcaagctt gccaccatgg atatgcgtgt acctgcacag ctgttaggac    60
tgcttctgct ctggcttagg ggagcaagat gcgacatcca gatgactcag agcccaagct   120
ccttgtctgc cagtgtgggt gatagggtca ccataacctg tcgagcttca caggatatcg   180
gcaactacct acgctggtat cagcagaaac cgggcaaagc cccaaagctg ctgatctatg   240
gcgccaccaa tctggctgct ggtgttccct ctcggttcag tgggtctgga tcaggcacag   300
acttcacact caccatttcc agcctccaac ccgaggactt tgcgacgtac tactgcttgc   360
agtccaagga atcccttgg acatttgggc aagggactaa ggtggagatt aagcgtacga   420
attaaaa                                                              427
```

<210> SEQ ID NO 48
<211> LENGTH: 429
<212> TYPE: DNA
<213> ORGANISM: Artificial
<220> FEATURE:
<223> OTHER INFORMATION: Hum11B7-VH

<400> SEQUENCE: 48

```
aattaaggta ccaagcttgc caccatgaag cacctctggt tctttctcct gctagtggct    60
gctcctcgct gggtgttgag ccaggttcag ttgcaggaat ctggaccagg actggtcaaa   120
ccctctgaga cactgtcact gacatgcact gtgtcaggtg ctccatttc ctccaactat    180
tggggctgga ttcggcaacc tccgggaaaa gggcttgagt ggataggcta catcacctat   240
tctgggagta cctcctacaa tcccagtctt aagagcaggg tgactatcag cgtagacacc   300
tccaagaacc agtttagcct caagctgagt tctgtgactg cagcggatac agccgtctac   360
tattgtgcca gaaccacgtt ctactattgg ggtcagggca cattagtcac cgttagctca   420
gcgaattaa                                                           429
```

<210> SEQ ID NO 49
<211> LENGTH: 427
<212> TYPE: DNA
<213> ORGANISM: Artificial
<220> FEATURE:
<223> OTHER INFORMATION: Hum11D5-VLk

<400> SEQUENCE: 49

```
aattaaaagc tagcaagctt gccaccatgg atatgcgcgt cttagcccaa ctactcggtc    60
tgcttctgtt gtgctttcca ggagccaggt gtgacatcca gatgacacag tcccctagta   120
gcctgtctgc gtctgtaggc gatcgagtga ccattacctg cagagcttcc caggatattg   180
gcaactatct gagctggttt cagcagaaac caggcaaagc acccaagagt ctcatctatg   240
gggccatcaa gctcgctgtt ggtgtgcctt cacggttttc cggatctggg tcaggcacag   300
acttcactct gaccatttcc agccttcaac cggaagactt cgcaacgtac tactgtctgc   360
agtacatcca gttccccttg actttcggtg gagggacaaa ggtggagata aagcgtacga   420
attaaaa                                                              427
```

<210> SEQ ID NO 50
<211> LENGTH: 429
<212> TYPE: DNA
<213> ORGANISM: Artificial
<220> FEATURE:
<223> OTHER INFORMATION: Hum11D5-VH

<400> SEQUENCE: 50

```
aattaaggta ccaagcttgc caccatgaag catctgtggt tctttctgct gcttgtggct    60
gctcctaggt gggtgttaag ccaggttcag ctccaggaat ctggtcccgg attggtgaaa   120
ccgagtgaga ctctatccct gacatgcacc gttagtggag gcagtatctc tagcaactat   180
tggggctgga ttcggcaacc acctggtaag ggccttgagt ggattgggca catcaccaac   240
tctgggaata ccacctacaa tccctccctg aaatcacgcg tcacgataag cgtggacact   300
tccaagaacc agttctccct caagctctca agcgtcacag cagcggatac agccgtatac   360
tactgtgcaa gagggccctt tgactattgg ggacagggca cattggtgac tgtcagctca   420
gcgaattaa                                                            429
```

```
<210> SEQ ID NO 51
<211> LENGTH: 20
<212> TYPE: DNA
<213> ORGANISM: Artificial
<220> FEATURE:
<223> OTHER INFORMATION: primer kappa_GSP1

<400> SEQUENCE: 51
gatggatgca ttggtgcagc                                                 20

<210> SEQ ID NO 52
<211> LENGTH: 20
<212> TYPE: DNA
<213> ORGANISM: Artificial
<220> FEATURE:
<223> OTHER INFORMATION: primer new_kappa_GSP1

<400> SEQUENCE: 52
atagatacag ttggtgcagc                                                 20

<210> SEQ ID NO 53
<211> LENGTH: 19
<212> TYPE: DNA
<213> ORGANISM: Artificial
<220> FEATURE:
<223> OTHER INFORMATION: primer heavy_GSP1

<400> SEQUENCE: 53
cagggtcacc atggagtta                                                  19

<210> SEQ ID NO 54
<211> LENGTH: 32
<212> TYPE: DNA
<213> ORGANISM: Artificial
<220> FEATURE:
<223> OTHER INFORMATION: primer XhoI-kGSP2

<400> SEQUENCE: 54
ccgctcgagc ggccgtttca gctccagctt gg                                   32

<210> SEQ ID NO 55
<211> LENGTH: 32
<212> TYPE: DNA
<213> ORGANISM: Artificial
<220> FEATURE:
<223> OTHER INFORMATION: primer XhoI-hGSP2

<400> SEQUENCE: 55
ccgctcgagc gggccagtgg atagacagat gg                                   32

<210> SEQ ID NO 56
```

```
<211> LENGTH: 21
<212> TYPE: DNA
<213> ORGANISM: Artificial
<220> FEATURE:
<223> OTHER INFORMATION: primer RT-gamma

<400> SEQUENCE: 56
gcgtgtagtg gttgtgcaga g                                        21

<210> SEQ ID NO 57
<211> LENGTH: 16
<212> TYPE: DNA
<213> ORGANISM: Artificial
<220> FEATURE:
<223> OTHER INFORMATION: primer RT-gamma2

<400> SEQUENCE: 57
gggcttgccg gccgtg                                              16

<210> SEQ ID NO 58
<211> LENGTH: 20
<212> TYPE: DNA
<213> ORGANISM: Artificial
<220> FEATURE:
<223> OTHER INFORMATION: primer RT-kappa

<400> SEQUENCE: 58
tggaactgag gagcaggtgg                                          20

<210> SEQ ID NO 59
<211> LENGTH: 39
<212> TYPE: DNA
<213> ORGANISM: Artificial
<220> FEATURE:
<223> OTHER INFORMATION: primer 5' Blp

<400> SEQUENCE: 59
agataagctt tgctcagcgt ccaccaaggg cccatcggt                     39

<210> SEQ ID NO 60
<211> LENGTH: 34
<212> TYPE: DNA
<213> ORGANISM: Artificial
<220> FEATURE:
<223> OTHER INFORMATION: primer 3' Bam(GAG)

<400> SEQUENCE: 60
agatggatcc tcatttaccc ggagacaggg agag                          34

<210> SEQ ID NO 61
<211> LENGTH: 39
<212> TYPE: DNA
<213> ORGANISM: Artificial
<220> FEATURE:
<223> OTHER INFORMATION: primer 5' Bsi:

<400> SEQUENCE: 61
agataagctt cgtacggtgg ctgcaccatc tgtcttcat                     39

<210> SEQ ID NO 62
<211> LENGTH: 36
<212> TYPE: DNA
<213> ORGANISM: Artificial
<220> FEATURE:
<223> OTHER INFORMATION: primer 3' Bam(CTT)

<400> SEQUENCE: 62
```

-continued agatggatcc ctaacactct cccctgttga agctct          36

<210> SEQ ID NO 63
<211> LENGTH: 42
<212> TYPE: DNA
<213> ORGANISM: Artificial
<220> FEATURE:
<223> OTHER INFORMATION: primer VL-11B7-5'

<400> SEQUENCE: 63
agataagctt gtgcattccg acatccagat gacccaggct cc          42

<210> SEQ ID NO 64
<211> LENGTH: 33
<212> TYPE: DNA
<213> ORGANISM: Artificial
<220> FEATURE:
<223> OTHER INFORMATION: primer VL-11B7-3'

<400> SEQUENCE: 64
agatcgtacg tttcagctcc agcttggtgc ctc          33

<210> SEQ ID NO 65
<211> LENGTH: 45
<212> TYPE: DNA
<213> ORGANISM: Artificial
<220> FEATURE:
<223> OTHER INFORMATION: primer VL-11D5-5'

<400> SEQUENCE: 65
agataagctt gtgcattccg acatccagat gacccagtct ccatc          45

<210> SEQ ID NO 66
<211> LENGTH: 27
<212> TYPE: DNA
<213> ORGANISM: Artificial
<220> FEATURE:
<223> OTHER INFORMATION: primer VL-11D5-3'

<400> SEQUENCE: 66
agatcgtacg tttcagcttg gtcccag          27

<210> SEQ ID NO 67
<211> LENGTH: 42
<212> TYPE: DNA
<213> ORGANISM: Artificial
<220> FEATURE:
<223> OTHER INFORMATION: primer VH-11B7/11D5-5'

<400> SEQUENCE: 67
agataagctt gtgcattccg aggtgcagct tcaggagtca gg          42

<210> SEQ ID NO 68
<211> LENGTH: 36
<212> TYPE: DNA
<213> ORGANISM: Artificial
<220> FEATURE:
<223> OTHER INFORMATION: primer VH-11B7/11D5-3'

<400> SEQUENCE: 68
agatgctgag ctgacagtga ccatgactcc ttggcc          36

<210> SEQ ID NO 69
<211> LENGTH: 37
<212> TYPE: DNA

```
<213> ORGANISM: Artificial
<220> FEATURE:
<223> OTHER INFORMATION: primer MOUSE1

<400> SEQUENCE: 69
gcgaattcgc caccatgggc agggtcccgc tggcctg                              37

<210> SEQ ID NO 70
<211> LENGTH: 34
<212> TYPE: DNA
<213> ORGANISM: Artificial
<220> FEATURE:
<223> OTHER INFORMATION: primer MOUSE2

<400> SEQUENCE: 70
cagccgaggt ataggctgtc acagacacag tcag                                34

<210> SEQ ID NO 71
<211> LENGTH: 30
<212> TYPE: DNA
<213> ORGANISM: Artificial
<220> FEATURE:
<223> OTHER INFORMATION: primer MOUSE3

<400> SEQUENCE: 71
gcaccctgtt agggtaccgg ctggcatatc                                     30

<210> SEQ ID NO 72
<211> LENGTH: 39
<212> TYPE: DNA
<213> ORGANISM: Artificial
<220> FEATURE:
<223> OTHER INFORMATION: primer MOUSE4

<400> SEQUENCE: 72
ataagaatgc ggccgctcag gctccgtcct cctgccctg                           39

<210> SEQ ID NO 73
<211> LENGTH: 34
<212> TYPE: DNA
<213> ORGANISM: Artificial
<220> FEATURE:
<223> OTHER INFORMATION: primer CYNO1

<400> SEQUENCE: 73
cggaattcgc caccatggcg tggcggtgcc ccag                                34

<210> SEQ ID NO 74
<211> LENGTH: 31
<212> TYPE: DNA
<213> ORGANISM: Artificial
<220> FEATURE:
<223> OTHER INFORMATION: primer CYNO2

<400> SEQUENCE: 74
ctctgacctc gtgcagatgg caatcttcat c                                   31

<210> SEQ ID NO 75
<211> LENGTH: 24
<212> TYPE: DNA
<213> ORGANISM: Artificial
<220> FEATURE:
<223> OTHER INFORMATION: primer CYNO3

<400> SEQUENCE: 75
gtggccgctg cctgtgtcct catc                                           24
```

<210> SEQ ID NO 76
<211> LENGTH: 39
<212> TYPE: DNA
<213> ORGANISM: Artificial
<220> FEATURE:
<223> OTHER INFORMATION: primer CYNO4

<400> SEQUENCE: 76
ataagaatgc ggccgctcag gcaccatcct cctgccctg                                      39

<210> SEQ ID NO 77
<211> LENGTH: 36
<212> TYPE: DNA
<213> ORGANISM: Artificial
<220> FEATURE:
<223> OTHER INFORMATION: primer MER1

<400> SEQUENCE: 77
cggaattcgc caccatgggg ccggccccgc tgccgc                                         36

<210> SEQ ID NO 78
<211> LENGTH: 25
<212> TYPE: DNA
<213> ORGANISM: Artificial
<220> FEATURE:
<223> OTHER INFORMATION: MER2

<400> SEQUENCE: 78
tcggctgcca ttctggccaa cttcc                                                     25

<210> SEQ ID NO 79
<211> LENGTH: 32
<212> TYPE: DNA
<213> ORGANISM: Artificial
<220> FEATURE:
<223> OTHER INFORMATION: primer SKY1

<400> SEQUENCE: 79
cggaattcgc caccatggcg ctgaggcgga gc                                             32

<210> SEQ ID NO 80
<211> LENGTH: 33
<212> TYPE: DNA
<213> ORGANISM: Artificial
<220> FEATURE:
<223> OTHER INFORMATION: primer SKY2

<400> SEQUENCE: 80
gccctcgagc taacagctac tgtgtggcag tag                                            33

<210> SEQ ID NO 81
<211> LENGTH: 51
<212> TYPE: DNA
<213> ORGANISM: Artificial
<220> FEATURE:
<223> OTHER INFORMATION: leader sequence

<400> SEQUENCE: 81
atgggtgaca atgacatcca ctttgccttt ctctccacag gtgtgcattc c                        51

<210> SEQ ID NO 82
<211> LENGTH: 17
<212> TYPE: PRT
<213> ORGANISM: Artificial
<220> FEATURE:

<223> OTHER INFORMATION: leader sequence

<400> SEQUENCE: 82

Met Gly Asp Asn Asp Ile His Phe Ala Phe Leu Ser Thr Gly Val His
1               5                   10                  15

Ser

<210> SEQ ID NO 83
<211> LENGTH: 2682
<212> TYPE: DNA
<213> ORGANISM: Macaca fascicularis

<400> SEQUENCE: 83

| | |
|---|---|
| atggcgtggc ggtgccccag gatgggcagg gtcccgctgg cctggtgctt ggcgctgtgc | 60 |
| ggctgggtgt gcatggcccc caggggcaca caggctgaag aaagtccttt cgtgggtaac | 120 |
| ccagggaata tcacaggtgc ccggggactc acgggcaccc ttcggtgtca gctccaggtt | 180 |
| cagggagagc cccccgaggt acactggctt cgggacggac agatcctgga gctcgcggac | 240 |
| agtacccaga cccaggtgcc cctgggtgaa gatgagcagg atgactggat agtggtcagc | 300 |
| cagctcagaa tcgcctccct acagctttcc gacgcgggac agtaccagtg tttggtgttt | 360 |
| ctgggacatc agaacttcgt gtcccagcct ggctacgtag ggctggaggg cttaccttac | 420 |
| ttcctggagg agcctgagga caggactgtg gccgccaaca ccccttcaa cctgagctgc | 480 |
| caagcccagg accccagac gccgtggac ctactctggc tccaggatgc tgtccccctg | 540 |
| gccacagctc caggtcatgg tccccagcgc aacctgcatg ttccagggct gaacaagaca | 600 |
| tcctctttct cctgcgaagc cataacgcc aagggagtca ccacatcccg cacggccacc | 660 |
| atcacagtgc tcccccagca gccccgtaac ctccatctgg tctcccgcca acccacggag | 720 |
| ctggaggtgg cttggactcc aggcctgagc ggcatctacc ccctgaccca ctgcacccg | 780 |
| caggctgtgc tgtcagacga tgggatgggc atccaggcgg gagaaccaga ccccccagag | 840 |
| gagcccctca ccttgcaagc atctgtgccc cccaccagc ttcggctggg cagcctccat | 900 |
| cctcacaccc cttatcacat ccgtgtggca tgcaccagca gccagggccc ctcatcctgg | 960 |
| acacactggc ttcctgtgga gacgccggag ggagtgcccc tgggcccccc tgagaacatt | 1020 |
| agtgccacgc ggaatgggag ccaggccttc gtgcattggc aggagccccg gcgcccctg | 1080 |
| cagggtaccc tgttaggta ccggctggcg tatcaaggcc aggacacccc agaggtgcta | 1140 |
| atggacatag gctaaggca agaggtgacc ctggagctgc aggggacgg gtctgtgtcc | 1200 |
| aatctgacag tgtgtgtggc agcctacact gctgctgggg atggaccctg gagcctccca | 1260 |
| gtaccctgg aggcctggcg cccagggcaa gcacagccag tccaccagct ggtgaaggaa | 1320 |
| acttcagctc ctgccttctc gtggccctgg tggtatatac tgctaggagc agtcgtggcc | 1380 |
| gctgcctgtg tcctcatctt ggctctcttc cttgtccacc ggcgaaagaa ggagacccgt | 1440 |
| tatggagaag tgttcgagcc aacagtggaa agaggtgaac tggtagtcag gtaccgcgtg | 1500 |
| cgcaagtcct acagtcgccg gaccactgaa gctaccttga cagcctgggg catcagtgaa | 1560 |
| gagctgaagg agaagctgcg ggatgtgatg gtggaccggc acaaggtggc cctggggaag | 1620 |
| actctgggag aaggagagtt tggagccgtg atggaaggcc agctcaacca ggacgactcc | 1680 |
| atcctcaagg tggctgtgaa gacaatgaag attgccatct gcacaaggtc agagctggag | 1740 |
| gatttcctga gtgaagcagt ctgcatgaag gaattcgacc atcccaatgt catgaggctc | 1800 |
| atcggtgtct gtttccaggg ttctgaacga gagagctttc cagcacctgt ggtcatctta | 1860 |

```
ccttctcatga agcatggaga cctacacagc ttcctcctct attcccggct tggggaccag    1920
ccagtgtacc tgcccactca gatgctagtg aagttcatgg cggacatcgc cagtggcatg    1980
gaatatctga gtaccaagag attcatacac cgggacctgg cggccaggaa ctgcatgctg    2040
aatgagaaca tgtccgtgtg tgtggcggac ttcgggctct ccaagaagat ctacaacggg    2100
gactactacc gccagggacg tatcgccaag atgccagtca agtggattgc cattgagagt    2160
ctagctgacc gtgtctacac gagcaagagt gatgtgtggt ccttcggggt gacaatgtgg    2220
gagattgcca caagaggcca accccatat ccaggcgtgg agaacagcga gatttatgac    2280
tatctgcgcc agggaaatcg cctgaagcag cctgcggact gtctggatgg actgtatgcc    2340
ttgatgtcgc ggtgctggga gctaaatccc caggaccggc caagttttac agagctgcgg    2400
gaagatttgg agaacacact gaaggccttg cctcctgccc aggagcctga cgaaatcctc    2460
tatgtcaaca tggatgaagg tggaggttat cctgaacctc ccggcgctgc tggaggagct    2520
gaccccccaa cccagctaga ccctaaggat tcctgtagct gcctcacttc ggctgaggtc    2580
catcctgctg gacgctatgt cctctgccct tccacagccc ctagccccgc tcagcctgct    2640 gatagggct ccccagcagc ccagggcag gaggatggtg cc                          2682
```

<210> SEQ ID NO 84
<211> LENGTH: 894
<212> TYPE: PRT
<213> ORGANISM: Macaca fascicularis

<400> SEQUENCE: 84

```
Met Ala Trp Arg Cys Pro Arg Met Gly Arg Val Pro Leu Ala Trp Cys
1               5                   10                  15

Leu Ala Leu Cys Gly Trp Val Cys Met Ala Pro Arg Gly Thr Gln Ala
            20                  25                  30

Glu Glu Ser Pro Phe Val Gly Asn Pro Gly Asn Ile Thr Gly Ala Arg
        35                  40                  45

Gly Leu Thr Gly Thr Leu Arg Cys Gln Leu Gln Val Gln Gly Glu Pro
    50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Ala Ser Leu Gln Leu Ser Asp Ala
            100                 105                 110

Gly Gln Tyr Gln Cys Leu Val Phe Leu Gly His Gln Asn Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Asn Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
    210                 215                 220

Pro Gln Gln Pro Arg Asn Leu His Leu Val Ser Arg Gln Pro Thr Glu
```

```
            225                 230                 235                 240
Leu Glu Val Ala Trp Thr Pro Gly Leu Ser Gly Ile Tyr Pro Leu Thr
                245                 250                 255

His Cys Thr Leu Gln Ala Val Leu Ser Asp Asp Gly Met Gly Ile Gln
                260                 265                 270

Ala Gly Glu Pro Asp Pro Pro Glu Pro Leu Thr Leu Gln Ala Ser
                275                 280                 285

Val Pro Pro His Gln Leu Arg Leu Gly Ser Leu His Pro His Thr Pro
            290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
                340                 345                 350

Trp Gln Glu Pro Arg Ala Pro Leu Gln Gly Thr Leu Leu Gly Tyr Arg
                355                 360                 365

Leu Ala Tyr Gln Gly Gln Asp Thr Pro Glu Val Leu Met Asp Ile Gly
            370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Gly Gln Ala Gln
                420                 425                 430

Pro Val His Gln Leu Val Lys Glu Thr Ser Ala Pro Ala Phe Ser Trp
                435                 440                 445

Pro Trp Trp Tyr Ile Leu Leu Gly Ala Val Val Ala Ala Ala Cys Val
            450                 455                 460

Leu Ile Leu Ala Leu Phe Leu Val His Arg Arg Lys Lys Glu Thr Arg
465                 470                 475                 480

Tyr Gly Glu Val Phe Glu Pro Thr Val Glu Arg Gly Glu Leu Val Val
                485                 490                 495

Arg Tyr Arg Val Arg Lys Ser Tyr Ser Arg Arg Thr Thr Glu Ala Thr
                500                 505                 510

Leu Asn Ser Leu Gly Ile Ser Glu Glu Leu Lys Glu Lys Leu Arg Asp
            515                 520                 525

Val Met Val Asp Arg His Lys Val Ala Leu Gly Lys Thr Leu Gly Glu
            530                 535                 540

Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                565                 570                 575

Ser Glu Leu Glu Asp Phe Leu Ser Glu Ala Val Cys Met Lys Glu Phe
                580                 585                 590

Asp His Pro Asn Val Met Arg Leu Ile Gly Val Cys Phe Gln Gly Ser
            595                 600                 605

Glu Arg Glu Ser Phe Pro Ala Pro Val Val Ile Leu Pro Phe Met Lys
            610                 615                 620

His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                645                 650                 655
```

```
Ala Ser Gly Met Glu Tyr Leu Ser Thr Lys Arg Phe Ile His Arg Asp
            660             665             670
Leu Ala Ala Arg Asn Cys Met Leu Asn Glu Asn Met Ser Val Cys Val
            675             680             685
Ala Asp Phe Gly Leu Ser Lys Lys Ile Tyr Asn Gly Asp Tyr Tyr Arg
            690             695             700
Gln Gly Arg Ile Ala Lys Met Pro Val Lys Trp Ile Ala Ile Glu Ser
705             710             715             720
Leu Ala Asp Arg Val Tyr Thr Ser Lys Ser Asp Val Trp Ser Phe Gly
                725             730             735
Val Thr Met Trp Glu Ile Ala Thr Arg Gly Gln Thr Pro Tyr Pro Gly
            740             745             750
Val Glu Asn Ser Glu Ile Tyr Asp Tyr Leu Arg Gln Gly Asn Arg Leu
            755             760             765
Lys Gln Pro Ala Asp Cys Leu Asp Gly Leu Tyr Ala Leu Met Ser Arg
    770             775             780
Cys Trp Glu Leu Asn Pro Gln Asp Arg Pro Ser Phe Thr Glu Leu Arg
785             790             795             800
Glu Asp Leu Glu Asn Thr Leu Lys Ala Leu Pro Pro Ala Gln Glu Pro
            805             810             815
Asp Glu Ile Leu Tyr Val Asn Met Asp Glu Gly Gly Gly Tyr Pro Glu
            820             825             830
Pro Pro Gly Ala Ala Gly Gly Ala Asp Pro Pro Thr Gln Leu Asp Pro
            835             840             845
Lys Asp Ser Cys Ser Cys Leu Thr Ser Ala Glu Val His Pro Ala Gly
    850             855             860
Arg Tyr Val Leu Cys Pro Ser Thr Ala Pro Ser Pro Ala Gln Pro Ala
865             870             875             880
Asp Arg Gly Ser Pro Ala Ala Pro Gly Gln Glu Asp Gly Ala
            885             890
```